(12) United States Patent
Okihara

(10) Patent No.: US 11,273,264 B2
(45) Date of Patent: Mar. 15, 2022

(54) CAP, SYRINGE ASSEMBLY, AND PREFILLED SYRINGE

(71) Applicant: TERUMO KABUSHIKI KAISHA, Tokyo (JP)

(72) Inventor: Hitoshi Okihara, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 415 days.

(21) Appl. No.: 16/367,035

(22) Filed: Mar. 27, 2019

(65) Prior Publication Data

US 2019/0217020 A1    Jul. 18, 2019

Related U.S. Application Data

(63) Continuation of application No. PCT/JP2017/033976, filed on Sep. 20, 2017.

(30) Foreign Application Priority Data

Sep. 30, 2016 (JP) .............................. JP2016-194256
Mar. 27, 2017 (JP) .............................. JP2017-060535

(51) Int. Cl.
   *A61M 5/32* (2006.01)
   *A61M 5/31* (2006.01)
   *A61M 5/50* (2006.01)

(52) U.S. Cl.
   CPC ............ *A61M 5/3202* (2013.01); *A61M 5/31* (2013.01); *A61M 5/32* (2013.01); *A61M 5/50* (2013.01);

(Continued)

(58) Field of Classification Search
   CPC .. A61M 2005/3104; A61M 2005/3109; A61M 2005/311; A61M 5/5086
   See application file for complete search history.

(56) References Cited

U.S. PATENT DOCUMENTS 5,328,474 A    7/1994  Raines
5,624,402 A *  4/1997  Imbert ................ A61M 5/3134
                                          604/111
2013/0237911 A1  9/2013  Von Schuckmann

FOREIGN PATENT DOCUMENTS

JP    H03-64251 U     6/1991
JP    2002-315827 A   10/2002

(Continued)

OTHER PUBLICATIONS

International Searching Authority, Written Opinion, issued in connection with International Patent Application No. PCT/JP2017/033976, dated Oct. 17, 2017.

(Continued)

*Primary Examiner* — William R Carpenter
(74) *Attorney, Agent, or Firm* — Foley & Lardner LLP

(57) ABSTRACT

A syringe assembly includes a prefilled syringe and a cap. A cap body is configured to be displaced from a first position where a viewing portion is positioned in a cylindrical main body to a second position where the viewing portion protrudes in a distal end direction from an opening of the cylindrical main body. When a mounting tube portion of the cap removed from a syringe body is brought close to a nozzle portion of the syringe body, the cap body is pressed in the distal end direction by the nozzle portion, thereby being displaced from the first position to the second position, and the appearance of an outer peripheral portion of the viewing portion changes.

19 Claims, 58 Drawing Sheets

(52) U.S. Cl.
CPC .............. *A61M 2005/3107* (2013.01); *A61M 2005/3125* (2013.01)

(56) References Cited

FOREIGN PATENT DOCUMENTS

| | | | | |
|---|---|---|---|---|
| JP | 2009-022641 A | | 2/2009 | |
| JP | 2009022641 A | * | 2/2009 | .......... A61M 5/3134 |
| JP | 2013-078442 A | | 5/2013 | |
| WO | WO-2013/047042 A1 | | 4/2013 | |
| WO | WO-2015/097067 A1 | | 7/2015 | |
| WO | WO-2015097067 A1 | * | 7/2015 | .............. A61M 5/50 |

OTHER PUBLICATIONS

Extended European Search Report dated Mar. 9, 2020 in corresponding European Patent Application No. 17855903.5.
International Searching Authority, "International Search Report," issued in connection with International Patent Application No. PCT/JP2017/033976, dated Oct. 17, 2017.

* cited by examiner

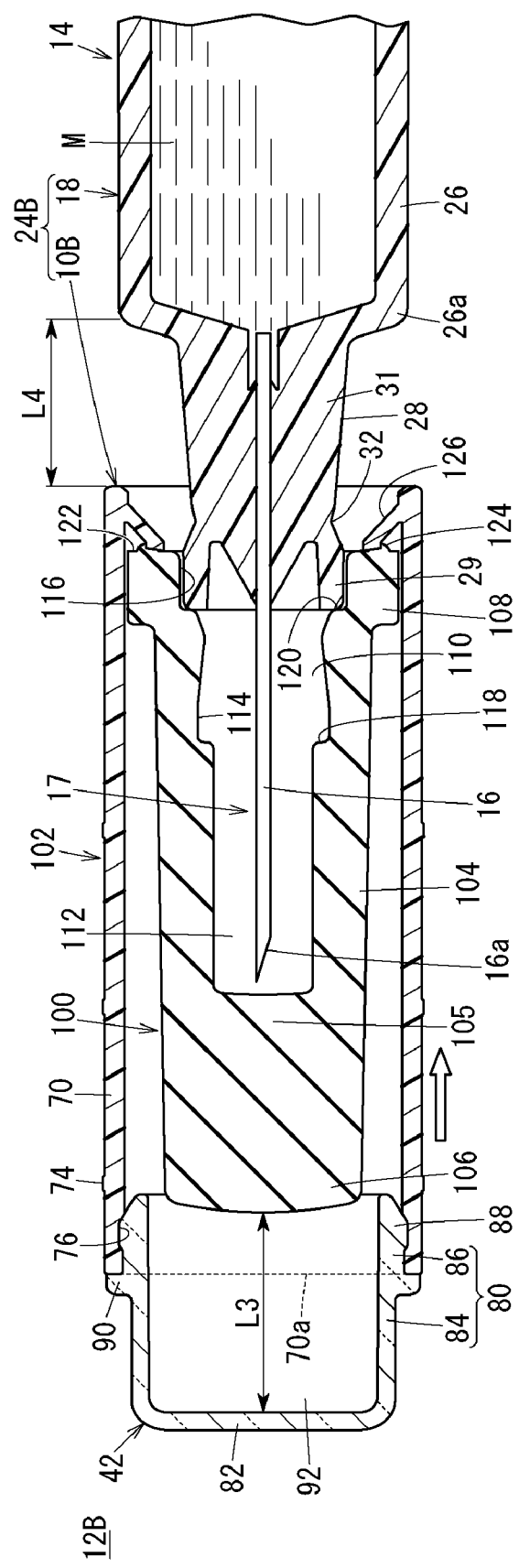

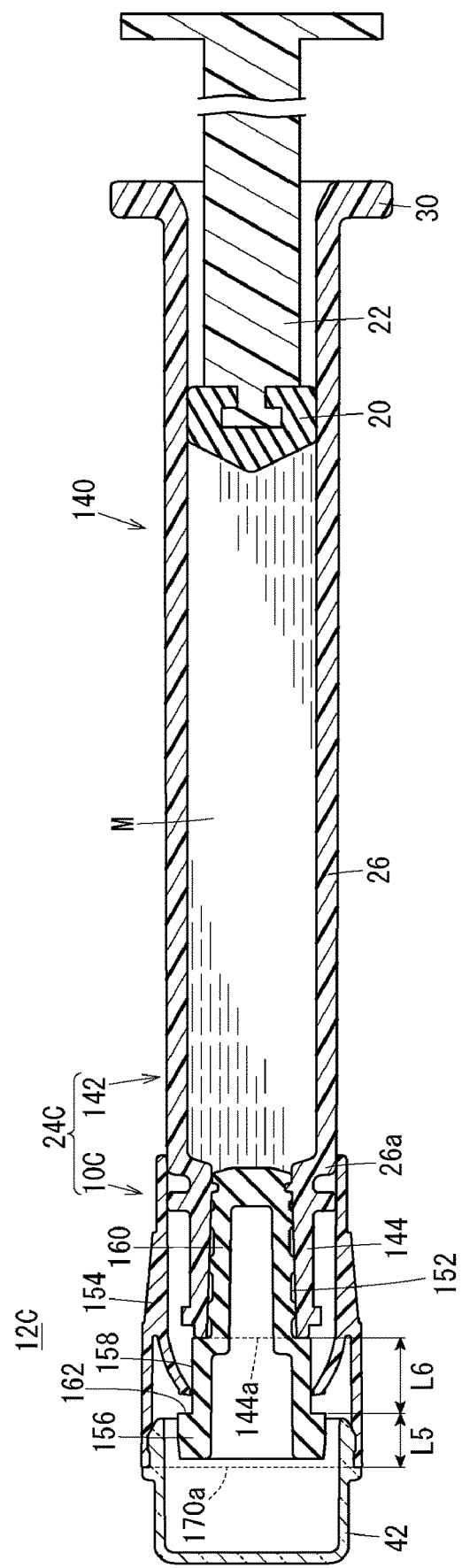

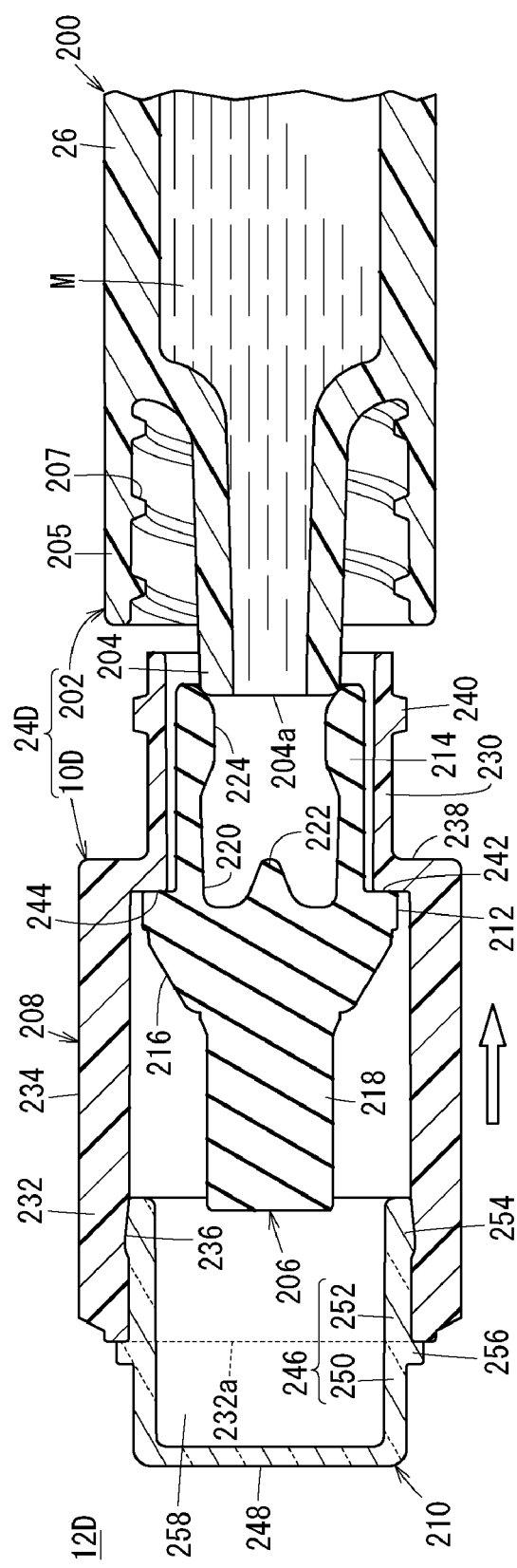

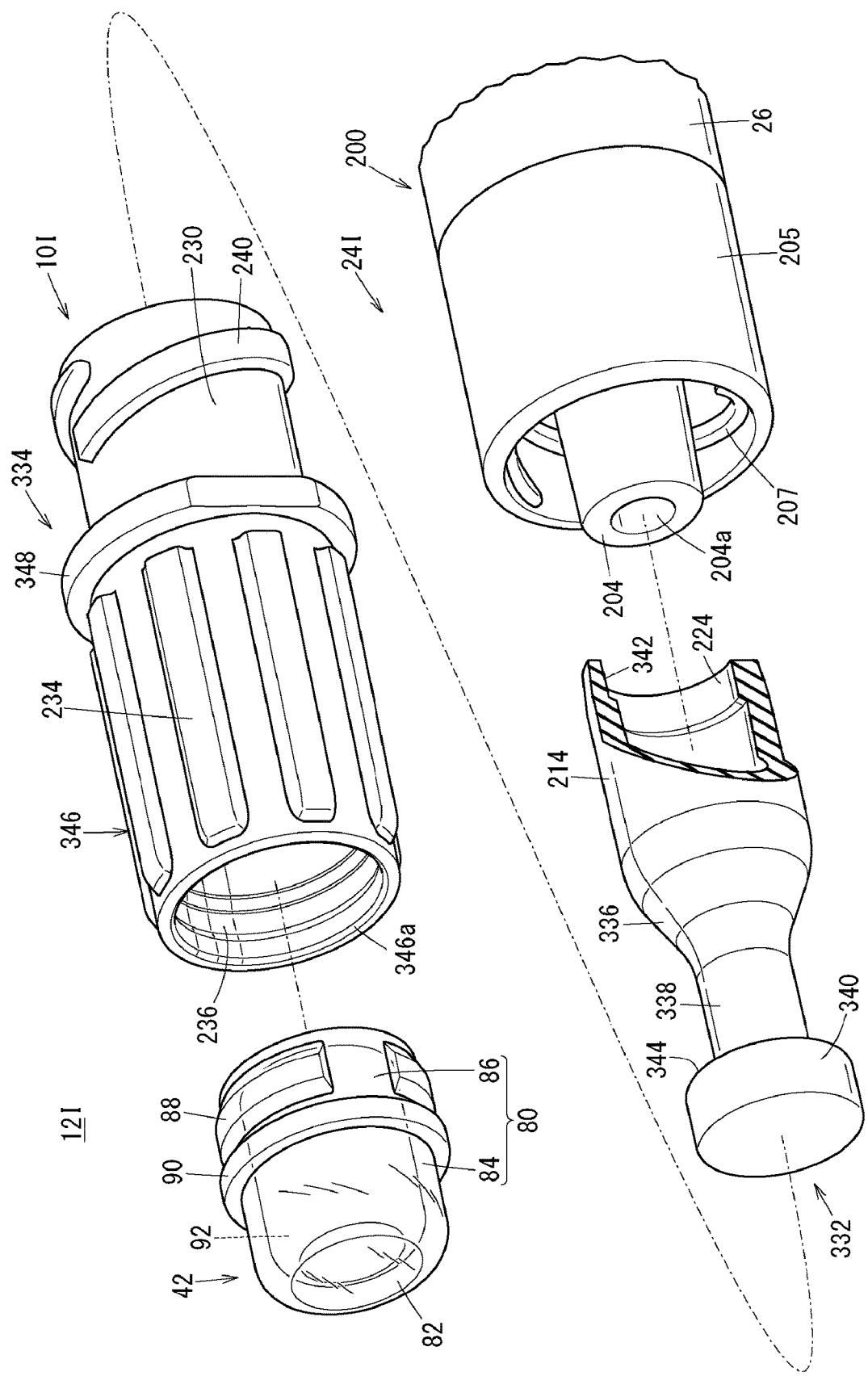

CAP, SYRINGE ASSEMBLY, AND PREFILLED SYRINGE

CROSS-REFERENCE TO RELATED APPLICATIONS

This is a bypass continuation of PCT Application No. PCT/JP2017/033976, filed on Sep. 20, 2017, which claims priority to Japanese Application No. 2016-194256, filed on Sep. 30, 2016, and Japanese Application No. 2017-060535, filed on Mar. 27, 2017. The contents of these applications are hereby incorporated by reference in their entireties.

BACKGROUND

The present disclosure relates to a cap that is detachable from a syringe body provided with a body portion configured to accommodate a drug and a nozzle portion protruding in a distal end direction from the distal end portion of the body portion and having a drug discharge port at the distal end of the nozzle portion, a syringe assembly, and a prefilled syringe.

Disclosed in, for example, JP 2002-315827 A is a configuration in which the outer surface of a luer lock adapter of a syringe body and the outer surface of a cap are covered with a heat-shrinkable resin film and the cap is opened by breaking of a perforation disposed in the heat-shrinkable resin film. With such a prefilled syringe, it is possible to discriminate between the unopened state and the recapped state of the cap, where the cap is remounted on the syringe body after removal from the syringe body, by viewing the perforation.

SUMMARY

In the related art as described above, however, broken portions of the heat-shrinkable resin film may be in contact with or close to each other, and the perforation may appear unbroken in the recapped state. In this case, it is not easy to discriminate between the unopened state of the cap and the opened state of the cap that follows cap opening.

Certain embodiments of the present disclosure have been made in view of such problems, and an object of certain embodiments is to provide a cap, a syringe assembly, and a prefilled syringe with which it is possible to discriminate between the unopened and opened states of the cap with ease and reliability.

According to one embodiment, a cap is detachable from a syringe body that includes a body portion that is configured to accommodate a drug and a nozzle portion that protrudes in a distal direction from a distal end portion of the body portion and includes a drug discharge port at a distal end of the nozzle portion. The cap includes a cap body and a tubular cap cover that covers the cap body. The cap body includes a mounting portion that is configured to be mounted on the nozzle portion and that includes a sealing portion that liquid-tightly seals the drug discharge port being disposed in the mounting portion, and a viewing portion that is positioned distal of the mounting portion. The cap cover includes a cylindrical main body that includes an opening at a distal end of the cylindrical main body and an engaging portion that inhibits detachment of the cap body in a proximal end direction with respect to the cap cover by engagement with the cap body. The cap body is configured to be displaced in the cap cover along an axial direction of the cap cover from a first position at which the viewing portion is positioned in the cylindrical main body to a second position at which the viewing portion protrudes in a distal direction from the opening of the cylindrical main body. The sealing portion is configured to liquid-tightly seal the nozzle portion in a state in which the cap body is positioned at the first position. The mounting portion is pressed in a distal direction by the nozzle portion of the syringe body so as to displace the cap body from the first position to the second position when the mounting portion of the cap removed from the syringe body is brought close to the nozzle portion of the syringe body in a state in which the cap body is disposed at the first position. At least an outer peripheral portion of the viewing portion changes in appearance by the viewing portion protruding from the opening due to displacement of the cap body is displaced from the first position to the second position.

According to this configuration, when the mounting portion of the cap removed from the syringe body is close to the nozzle portion of the syringe body, the mounting portion is pressed in the distal end direction by the nozzle portion of the syringe body such that the cap body is displaced from the first position to the second position and at least the outer peripheral portion of the viewing portion changes in appearance as the viewing portion protrudes from the opening as a result of the displacement of the cap body from the first position to the second position. As a result, a user can easily and reliably discriminate between the unopened and opened states of the cap even in a case where the cap is remounted on the syringe body after removal from the syringe body.

In the cap described above, the cap may include a distal end cover member that is mounted on a distal end portion of the cap cover. The distal end cover member may include an annular peripheral wall portion that extends in a distal direction from the opening of the cylindrical main body and a distal end wall that is disposed at a distal end of the annular peripheral wall portion. The annular peripheral wall portion and the distal end wall may form a receiving space in which the viewing portion, which has protruded in a distal direction from the opening of the cylindrical main body, is received. The cylindrical main body and the distal end cover member may cover the cap body such that a user operating the cap cannot touch the cap body in an abutting state in which the cap body is positioned at the second position and the mounting portion abuts against the nozzle portion of the syringe body.

According to this configuration, it is possible to inhibit a user from accidentally returning the cap body at the second position to the first position in the opened state.

In the cap described above, a distal end of the annular peripheral wall portion may be closed by the distal end wall.

According to this configuration, it is possible to more reliably inhibit a user from accidentally returning the cap body at the second position to the first position in the opened state.

In the cap described above, one of the distal end cover member and the cylindrical main body may be transparent and the other of the distal end cover member and the cylindrical main body may be substantially opaque.

According to this configuration, the change in the appearance of the outer peripheral portion of the viewing portion in a state in which the cap body has been displaced from the first position to the second position becomes clear.

In the cap described above, the distal end cover member may be transparent and the cylindrical main body may be substantially opaque.

According to this configuration, the outer peripheral portion of the viewing portion is hidden in the cylindrical main body and substantially invisible when the cap body is at the first position and the outer peripheral portion of the viewing portion becomes visible through the distal end cover member when the cap body is at the second position.

In the cap described above, the distal end cover member may include an engagement extending portion that extends from a proximal end of the annular peripheral wall portion into the cylindrical main body through the opening. The distal end cover member may be mounted on the cylindrical main body by engagement of the engagement extending portion with an inner peripheral surface of the cylindrical main body.

According to this configuration, the distal end cover member is engaged with the inner peripheral surface of the cylindrical main body in the structure described above. Accordingly, it is possible to inhibit a user from accidentally removing the distal end cover member from the cylindrical main body.

In the cap described above, the distal end cover member may include a positioning projection that protrudes from an outer peripheral surface of a proximal end portion of the annular peripheral wall portion. Movement of the distal end cover member in a proximal direction with respect to the cylindrical main body may be inhibited by the positioning projection abutting against a distal end surface of the cylindrical main body.

According to this configuration, the distal end cover member is not proximally moved with respect to the cap cover and it is possible to reliably form the receiving space, which receives the viewing portion protruding from the opening of the cylindrical main body.

In the cap described above, the distal end cover member may include an annular portion that includes the annular peripheral wall portion and the engagement extending portion. An inner diameter of the annular portion may be constant from a distal end of the annular portion to a proximal end of the annular portion and larger than an outer diameter of the viewing portion. At least a distal end of the viewing portion may be positioned in the annular portion when the cap body is at the first position.

According to this configuration, it is possible to smoothly displace the cap body from the first position to the second position. In other words, it is possible to suppress the cap body being caught on the inner surface of the distal end cover member during the displacement from the first position to the second position.

In the cap described above, an outer diameter of the viewing portion may be larger than an outer diameter of a part of the nozzle portion at which the mounting portion is fitted.

According to this configuration, the outer peripheral portion of the viewing portion can be easily viewed.

In the cap described above, a large-diameter portion that protrudes radially outward may be disposed in the cap body. The engaging portion may be positioned more proximal than the large-diameter portion and face an engagement surface of the large-diameter portion, the engagement surface facing a proximal direction, and detachment of the cap body in a proximal end direction with respect to the cap cover may be inhibited by engagement of the engaging portion with the engagement surface.

According to this configuration, detachment of the cap body in the proximal end direction with respect to the cap cover can be inhibited by the engaging portion being brought into contact with the engagement surface of the large-diameter portion.

In the cap described above, the cap is configured to displace the cap cover in a distal direction relative to the syringe body such that the engagement surface is pressed in a distal end direction by the engaging portion and the cap body is removed from a syringe body.

According to this configuration, the cap can be easily removed from the syringe body.

In the cap described above, the engaging portion may be an engaging claw portion that extends so as to be inclined radially inward from an inner peripheral surface of the cylindrical main body toward a distal end direction. An inner diameter of a portion of the cylindrical main body that is proximal of the engaging claw portion may be larger than an outer diameter of the large-diameter portion. The engaging claw portion may be formed so as to be elastically deformable outward in a radial direction of the cylindrical main body.

According to this configuration, when the cap is manufactured, the cap body is inserted from the proximal direction of the cap cover after the cap body is attached to the syringe body. As a result, the large-diameter portion climbs over the engaging claw portion while elastically deforming the engaging claw portion radially outward. Accordingly, assembly of the cap cover with respect to the cap body can be performed with ease.

In the cap described above, a plurality of the engaging claw portions may be disposed along a circumferential direction of the cylindrical main body. A predetermined gap may be formed between the engaging claw portions that are adjacent to each other.

According to this configuration, detachment of the cap body in the proximal end direction with respect to the cap cover can be effectively inhibited by the plurality of engaging claw portions. In addition, since a predetermined gap is formed between the engaging claw portions adjacent to each other, each engaging claw portion can be elastically deformed with reliability during manufacturing of the cap.

In the cap described above, a hole diameter of a central hole that is formed by inner ends of the plurality of engaging claw portions may be smaller than an outer diameter of the large-diameter portion.

According to this configuration, each engaging claw portion can be reliably brought into contact with the engagement surface of the large-diameter portion.

In the cap described above, the large-diameter portion may be a large-diameter distal end portion that is disposed in a distal end portion of the cap body and functions as the viewing portion. The cap body may include a small-diameter middle portion that is disposed at a proximal end of the large-diameter distal end portion. A proximal stepped surface that functions as the engagement surface may be disposed at a boundary between the large-diameter distal end portion and the small-diameter middle portion.

According to this configuration, the outer peripheral portion of the large-diameter distal end portion (viewing portion) can be easily viewed and an increase in the outer diameter of the proximal end side of the cap body can be suppressed.

In the cap described above, the distal end cover member may include an annular portion that includes the annular peripheral wall portion and the engagement extending portion. The cap body may include a large-diameter distal end portion that is disposed in a distal end portion of the cap body and functions as the viewing portion. An inner diameter of the annular portion may be set to a range of 101% to 150% of an outer diameter of the large-diameter distal end portion.

According to this configuration, it is possible to more smoothly displace the cap body from the first position to the second position while relatively increasing the outer diameter of the large-diameter distal end portion (viewing portion).

In the cap described above, an axial length of the small-diameter middle portion may be longer than a distance from the proximal stepped surface of the large-diameter distal end portion to the opening of the cylindrical main body in a state in which the cap body is at the first position.

According to this configuration, it is possible to inhibit the small-diameter middle portion from being caught by the engaging claw portion and inhibit the displacement from being hindered during the displacement of the cap body from the first position to the second position.

In the cap described above, the large-diameter portion may be an annular large-diameter proximal end portion that is disposed in a proximal end portion of the cap body. A proximal end surface of the large-diameter proximal end portion may function as the engagement surface.

According to this configuration, detachment of the cap body in the proximal end direction with respect to the cap cover can be inhibited by the engaging claw portion being brought into contact with the proximal end surface of the large-diameter proximal end portion.

In the cap described above, the nozzle portion may include a hollow needle body that includes the drug discharge port at a distal end thereof and a needle hub to which a proximal end side of the needle body is attached. The mounting portion may be a mounting tube portion that is configured to accommodate the needle body and the needle hub. The sealing portion may close a distal end of the mounting tube portion. The drug discharge port may be liquid-tightly sealed by a distal end portion of the needle body puncturing the sealing portion and the needle hub may be fitted in the mounting tube portion when the cap body is at the first position.

According to this configuration, it is possible to easily and reliably discriminate between the unopened state and the opened state of the cap with respect to the syringe body having the needle body.

In the cap described above, the mounting tube portion may include a first hole portion that is positioned in a distal end portion of the mounting tube portion and a second hole portion that is positioned proximal of the first hole portion. A distal end portion of the needle hub may be liquid-tightly fitted into the second hole portion in a state in which the needle body is inserted through the first hole portion when the cap body is at the first position.

According to this configuration, the drug can be reliably sealed in the syringe body in the unopened state of the cap.

In the cap described above, a diameter-reduced portion that is smaller in outer diameter than a distal end of the needle hub may be disposed on a distal end side of the needle hub. A wall surface that constitutes the second hole portion may abut against the diameter-reduced portion when the cap body is at the first position.

According to this configuration, it is possible to inhibit the mounting tube portion from accidentally coming out of the needle hub in the unopened state of the cap.

In the cap described above, the mounting tube portion may include a third hole portion that is positioned proximal of the second hole portion. The needle hub may be fitted into the second hole portion and the third hole portion when the cap body is at the first position. The drug discharge port may be liquid-tightly sealed by a distal end portion of the needle body puncturing the sealing portion and a distal end portion of the needle hub may be fitted into the third hole portion without being fitted into the second hole portion when the cap body is at the second position.

According to this configuration, the drug can be more reliably sealed in the syringe body in the unopened state of the cap. In addition, it is possible to inhibit needle tip exposure attributable to an accidental disengagement of the cap from the syringe body in the opened state.

In the cap described above, a distal end of the cap body may abut against the distal end wall when the cap body is at the second position.

According to this configuration, the distal end portion of the needle hub can be pushed into the third hole portion of the cap body in a state in which the distal end of the cap body abuts against the distal end wall.

In the cap described above, the mounting tube portion may include a third hole portion that is positioned proximal of the second hole portion. A hole diameter of the third hole portion may be larger than an outer diameter of a distal end portion of the needle hub. A distal end of the needle body may be positioned in the first hole portion and a distal end portion of the needle hub may be inserted into the third hole portion when the cap body is at the second position.

According to this configuration, it is possible to relatively reduce the force that is required when the cap in the opened state is removed from the syringe body. As a result, it is possible to reconfirm that the cap was in the opened state during removal of the cap from the syringe body.

In the cap described above, the nozzle portion may be formed in a hollow shape. The mounting portion may be fitted into the nozzle portion.

According to this configuration, it is possible to easily and reliably discriminate between the unopened and opened states of the cap with respect to the syringe body having the hollow nozzle portion.

In the cap described above, a first locking portion may be disposed on an inner peripheral surface of the nozzle portion. A second locking portion that is locked by the first locking portion in a state in which the cap body is at the first position may be disposed in an outer peripheral surface of the mounting portion.

According to this configuration, the cap body can be reliably locked with respect to the tube portion.

In the cap described above, one of the first locking portion and the second locking portion may be an annular projecting portion. The other of the first locking portion and the second locking portion may be an annular recess.

According to this configuration, the cap body can be locked in the tube portion by the fitting force between the annular projecting portion and the annular recess.

In the cap described above, an annular seal projection that comes into liquid-tight contact with an inner peripheral surface of the nozzle portion may be disposed on an outer peripheral surface of the mounting portion.

According to this configuration, the space between the tube portion and the mounting portion can be effectively sealed in a liquid-tight manner by the seal projection.

In the cap described above, a recessed portion that is open to a distal end surface of the cap body may be formed in the mounting portion.

According to this configuration, the mounting portion can be easily fitted into the tube portion during manufacturing of the cap.

In the cap described above, the mounting portion may include an abutting portion that abuts against the nozzle portion and a fitting portion that is disposed distal of the abutting portion and is configured to be fitted with the nozzle portion. The cap may be configured to be mounted on the syringe body by fitting of the fitting portion onto the nozzle portion. Movement of the cap cover in a proximal direction with respect to the syringe body may be restricted by a proximal end portion of the cap cover abutting against a distal end portion of the body portion of the syringe body. A distance from a distal end of the cap body to the distal end wall of the distal end cover member may be longer than a distance from a proximal end of the cap cover to a distal end of a body portion of the syringe body in a state in which the engaging portion of the cap cover is engaged with the cap body and the abutting portion of the mounting portion abuts against the nozzle portion.

According to this configuration, when the cap body is displaced from the first position to the second position by the mounting tube portion of the cap body being pressed in the distal end direction by the nozzle portion of the syringe body, the proximal end portion of the cap cover abuts against the distal end portion of the body portion of the syringe body, and a predetermined gap is formed between the distal end of the cap body and the distal end wall as a result. As a result, fitting of the mounting tube portion of the cap body onto the nozzle portion can be inhibited and remounting of the cap onto the syringe body can be inhibited when the cap removed from the syringe body is to be remounted on the syringe body.

In the cap described above, the syringe body may include a cylindrical lock adapter that includes a female screw portion on an inner peripheral surface of the lock adapter and covers an outer peripheral portion of the nozzle portion. The mounting portion may be a cylindrical mounting tube portion that is configured to accommodate the nozzle portion. The mounting tube portion may include the sealing portion that is positioned in a distal end portion of the mounting tube portion and an abutting portion that is positioned in a proximal end portion of the mounting tube portion and is configured to abut against a distal end portion of the nozzle portion. The cap cover may include a cylindrical connecting portion that is positioned in a proximal end portion of the cap cover and is detachable from the lock adapter by screwing. The cylindrical connecting portion may be tubular so as to be inserted between the lock adapter and the nozzle portion, and may include a male screw portion in an outer peripheral portion of the cylindrical connecting portion, the male screw portion being configured to be screwed with the female screw portion of the lock adapter. The mounting tube portion may be inserted between the cylindrical connecting portion and the nozzle portion and the sealing portion may liquid-tightly seal the drug discharge port in a state in which the cap is mounted on the syringe body by screwing of the male screw portion of the cylindrical connecting portion with the female screw portion of the lock adapter and the cap body is positioned at the first position. The cap body may be displaced from the first position to the second position and an outer peripheral portion of the viewing portion may change in appearance by the abutting portion of the cap body being pressed by the distal end portion of the nozzle portion when the male screw portion of the cylindrical connecting portion is screwed into the female screw portion of the lock adapter with the cap removed from the syringe body.

According to this configuration, the cap body is displaced from the first position to the second position and the outer peripheral portion of the viewing portion of the cap body changes in appearance when the male screw portion of the cap removed from the syringe body is screwed into the female screw portion of the lock adapter. Accordingly, a user can easily and reliably discriminate between the unopened state of the cap and the recapped state of the cap where the cap is remounted on the syringe body after removal from the syringe body by the screwing between the male screw portion of the cap cover and the female screw portion of the lock adapter.

In the cap described above, the cap cover may be substantially opaque. An outer peripheral portion of the viewing portion may be substantially invisible when the cap body is at the first position and an outer peripheral portion of the viewing portion may be visible when the cap body is at the second position.

According to this configuration, a change in the appearance of the viewing portion becomes clear and it is possible to discriminate between the unopened state and the recapped state of the cap with greater ease.

In the cap described above, the viewing portion may be disposed at a distal end of the cap body.

According to this configuration, a user can discriminate between the unopened state and the recapped state of the cap on the basis of whether or not the cap body protrudes from the opening of the cap cover.

In the cap described above, the mounting tube portion may include an abutting projecting portion that protrudes inward and functions as the abutting portion on an inner peripheral surface of the proximal end portion of the mounting tube portion.

According to this configuration, the abutting portion reliably abuts against the distal end portion of the nozzle portion, and thus the cap body can be reliably displaced from the first position to the second position.

In the cap described above, the abutting projecting portion may be annularly disposed on the inner peripheral surface of the proximal end portion of the mounting tube portion.

According to this configuration, the abutting projecting portion is capable of abutting against the distal end portion of the nozzle portion in a more reliable manner.

In the cap described above, the mounting tube portion may include a notch portion in which the abutting projecting portion is notched in an axial direction of the mounting tube portion. The inner peripheral surface of the mounting tube portion may be configured to form a circumferentially continuous airtight seal with an outer peripheral surface of the nozzle portion at least in a vicinity of a distal end of the abutting projecting portion when the sealing portion liquid-tightly seals the drug discharge port. The airtight seal may be released and an inside of the mounting tube portion, which is distal of the abutting projecting portion, may communicate with an outside via the notch portion when the sealing portion is separated by a predetermined distance from the drug discharge port and the abutting projecting portion abuts against an outer peripheral surface of the nozzle portion.

According to this configuration, the negative pressure in the cap body (mounting tube portion) is released during opening of the cap and it is possible to inhibit the drug in the nozzle portion from being pulled by the negative pressure in the cap and scattering when the cap is disengaged from the syringe outer tube.

In the cap described above, the abutting projecting portion may be sandwiched between the nozzle portion and the cylindrical connecting portion and compressed in a state in which the cap is mounted on the syringe body and the cap body is positioned at the first position.

According to this configuration, the cap body is unlikely to be disengaged from the nozzle portion, and thus a state in which the drug discharge port is sealed by the sealing portion can be reliably maintained.

In the cap described above, the distal end portion of the cap body may be a large-diameter distal end portion that functions as the viewing portion. The cap body may include a small-diameter middle portion that is smaller in outer diameter than the large-diameter distal end portion and the mounting tube portion between the large-diameter distal end portion and the mounting tube portion. The large-diameter distal end portion may include a proximal stepped surface at a boundary with the small-diameter middle portion. The cylindrical main body may include an engaging projection that protrudes from an inner peripheral surface of the cylindrical main body and functions as the engaging portion by engagement with the proximal stepped surface. The cap cover may have an inner diameter that is larger than an outer diameter of the large-diameter distal end portion from a proximal end of the cap cover to the engaging projection. The large-diameter distal end portion may be positioned more distal than the engaging projection in a state in which the cap body is positioned at the first position.

According to this configuration, the cap body is fitted onto the nozzle portion, and then the large-diameter distal end portion is inserted from the proximal end of the cap cover and allowed to climb over the engaging projection. As a result, the cap body is disposed at the first position and detachment of the cap body in the proximal end direction with respect to the cap cover is inhibited. As a result, the cap can be assembled with ease.

In the cap described above, the engaging projection may be an engaging claw portion that has elasticity and extends so as to be inclined in a distal direction from the inner peripheral surface of the cylindrical main body.

According to this configuration, when the large-diameter distal end portion climbs over the engaging claw portion (engaging projection) during assembly of the cap, the engaging claw portion is elastically deformed outward by the large-diameter distal end portion, and thus the large-diameter distal end portion climbs over the engaging claw portion with ease.

In the cap described above, a plurality of the engaging claw portions may be disposed at intervals along a circumferential direction of the cylindrical main body.

According to this configuration, the engaging claw portion is elastically deformed with ease. As a result, the large-diameter distal end portion climbs over the engaging claw portion with greater ease.

In the cap described above, an outer diameter of the small-diameter middle portion may be smaller than an inner diameter that is formed by an inner end portion of the engaging projection. An axial length of the small-diameter middle portion may be longer than a distance from the proximal stepped surface of the large-diameter distal end portion to the opening of the cap cover in a state in which the cap body is at the first position.

According to this configuration, it is possible to inhibit the small-diameter middle portion from being caught by the engaging projection and inhibit displacement from being hindered during the displacement of the cap body from the first position to the second position.

In the cap described above, an outer diameter of the cap may be equal to or smaller than an outer diameter of the lock adapter. The large-diameter distal end portion of the cap body may be larger than a distal end outer diameter of the nozzle portion.

According to this configuration, the outer peripheral portion of the cap does not protrude outward beyond the outer peripheral portion of the lock adapter. Accordingly, the cap is unlikely to be caught by a feeder or the like when the syringe outer tube is transported with the cap mounted. In addition, the large-diameter distal end portion as the viewing portion is larger than the distal end outer diameter of the nozzle portion, and thus a change in the appearance of the large-diameter distal end portion can be easily understood.

In the cap described above, the cap may include a distal end cover member that is attached to a distal end portion of the cap cover and forms a receiving space distal of the opening that receives the large-diameter distal end portion. The cap cover may be substantially opaque and the distal end cover member may be transparent. An inner diameter of the distal end cover member may be slightly larger than an outer diameter of the large-diameter distal end portion.

According to this configuration, the distal end cover member does not hinder a movement of the cap body from the first position to the second position and the large-diameter distal end portion (viewing portion) protruding from the opening is easily visible even in a state in which the distal end cover member is interposed.

In the cap described above, an inner diameter of the cylindrical connecting portion may be smaller than an inner diameter of the cylindrical main body. The cylindrical main body may include an engaging stepped surface that functions as the engaging portion at a boundary with the cylindrical connecting portion. The cap body may include a large-diameter portion that is positioned in the cap cover and has an outer diameter that is larger than an inner diameter of the cylindrical connecting portion and an outer diameter of the mounting tube portion. The large-diameter portion may include a proximal stepped surface at a boundary with the mounting tube portion. The engaging stepped surface may inhibit detachment of the cap body in a proximal end direction with respect to the cap cover by engagement with the proximal stepped surface.

According to this configuration, detachment of the cap body in the proximal end direction with respect to the cap cover can be reliably inhibited.

In the cap described above, the cap body may include a tapered portion that extends in a distal direction from a distal end of the large-diameter portion and decreases in outer diameter toward a distal end.

According to this configuration, the cap body is easily inserted from the proximal direction of the cap cover during assembly of the cap.

In the cap described above, the cap may include an inclination promoting portion that inclines an axis of the cap body with respect to an axis of the nozzle portion when the engaging stepped surface is engaged with the proximal stepped surface.

According to this configuration, the abutting portion of the cap body is capable of abutting against the distal end portion of the nozzle portion in a more reliable manner when the male screw portion of the cap removed from the syringe outer tube is screwed into the female screw portion of the lock adapter. Accordingly, it is possible to effectively suppress fitting of the cap body with respect to the nozzle portion in the recapped state.

In the cap described above, the inclination promoting portion may be a proximal end projection that proximally protrudes from a part of the proximal stepped surface of the large-diameter portion.

According to this configuration, the configuration of the inclination promoting portion can be simplified.

In the cap described above, the inclination promoting portion may be a distal end projection that protrudes in a distal direction from a part of the engaging stepped surface of the cylindrical connecting portion.

According to this configuration, the configuration of the inclination promoting portion can be simplified.

In the cap described above, the cap body may include a deformation-facilitated portion in the distal end portion of the cap body. The deformation-facilitated portion may be configured to be elastically deformed when the deformation-facilitated portion is axially pressed with a force that is weaker than a force that causes the abutting portion of the cap body to be pressed by the distal end portion of the nozzle portion.

According to this configuration, the distal end portion (deformation-facilitated portion) of the cap body is elastically deformed, and thus returning of the cap body from the second position to the first position can be suppressed even in a case where a user presses the distal end portion of the cap body to the syringe outer tube side in the recapped state.

In the cap described above, the cap may further include a displacement restricting portion that is configured to restrict displacement of the cap body from the second position to the first position by engagement with an outer peripheral surface of the cap body at the second position and such that the cap body is configured to climb over the displacement restricting portion from a proximal end side by means of a force that causes the abutting portion of the cap body to be pressed by a distal end portion of the nozzle portion.

According to this configuration, the cap body can be reliably displaced from the first position to the second position by the abutting portion of the cap body being pressed by the distal end portion of the nozzle portion. At the same time, returning of the cap body from the second position to the first position can be reliably suppressed by the displacement restricting portion.

In the cap described above, the cap body may include a first member that includes the mounting tube portion and a second member that is mounted on a distal end portion of the first member and includes the viewing portion. The first member may be comprised of a material that substantially contains no colorant. The second member may be comprised of a material that contains a colorant.

According to this configuration, the mounting tube portion, which comes into contact with the drug, contains no colorant. Accordingly, the drug is not adversely affected when the cap is mounted on the syringe outer tube filled with the drug. In addition, it is possible to easily discriminate between the unopened state and the recapped state of the cap since the viewing portion is colored.

In the cap described above, the cap cover may include an insertion restricting portion that is configured to abut against a distal end of the lock adapter at a proximal end of the cylindrical main body. The insertion restricting portion may restrict length of insertion of the cylindrical connecting portion between the lock adapter and the nozzle portion by abutting against a distal end of the lock adapter.

According to this configuration, the cylindrical connecting portion is inhibited from being excessively inserted. As a result, it is possible to inhibit the distal end portion (viewing portion) from protruding from the opening by the cap body being displaced relative to the cap cover with the nozzle portion sealed.

In the cap described above, an inner diameter of the annular portion may be slightly larger than an outer diameter of the distal end portion of the cap body.

According to this configuration, it is possible to more smoothly displace the cap body from the first position to the second position.

According to another embodiment, a syringe assembly includes the above-described cap and a syringe outer tube that constitutes the syringe body and is configured to accommodate a drug.

According to another embodiment, a syringe assembly includes the above-described cap and a syringe outer tube that constitutes the syringe body and is configured to accommodate a drug. The cap is mounted on the syringe outer tube by screwing of the male screw portion of the cylindrical connecting portion and the female screw portion of the lock adapter. The cylindrical connecting portion is inserted between the lock adapter and the nozzle portion. The cap body is positioned at the first position. The mounting tube portion is inserted between the cylindrical connecting portion and the nozzle portion. The sealing portion liquid-tightly seals the drug discharge port.

According to this configuration, it is possible to obtain a syringe assembly that is similar in action and effect to the above-described cap.

According to another embodiment, a prefilled syringe includes the above-described syringe assembly, a drug filled in the syringe outer tube, and a gasket that is configured to slide in the syringe outer tube in a liquid-tight manner and in an axial direction.

According to this configuration, it is possible to obtain a prefilled syringe that is similar in action and effect to the above-described syringe assembly (cap).

According to certain embodiments of the present disclosure, the cap body is displaced from the first position to the second position and at least the outer peripheral portion of the viewing portion of the cap body changes in appearance when the mounting portion of the cap removed from the syringe body is close to the nozzle portion of the syringe body. Accordingly, a user can easily and reliably discriminate between the unopened and opened states of the cap.

BRIEF DESCRIPTION OF THE DRAWINGS

FIG. 13A is a first explanatory diagram of a state in which the cap body illustrated in FIG. 9 is disposed at a first position.

FIG. 14 is a longitudinal cross-sectional view of a prefilled syringe according to a third embodiment of the present invention;

FIG. 24A is a longitudinal cross-sectional view illustrating a state in which a recap operation for the cap illustrated in FIG. 20 is in progress.

FIG. 34 is an exploded perspective view of the distal end part of a prefilled syringe according to a ninth embodiment of the present invention;

DETAILED DESCRIPTION

Hereinafter, preferred embodiments of a cap, a syringe assembly, and a prefilled syringe according to certain embodiments of the present invention will be described with reference to accompanying drawings. In the following description relating to the prefilled syringe and components of the prefilled syringe, the left side of FIG. 1 is referred to as "distal end" and the right side of FIG. 1 is referred to as "proximal end".

First Embodiment

Figure 1:
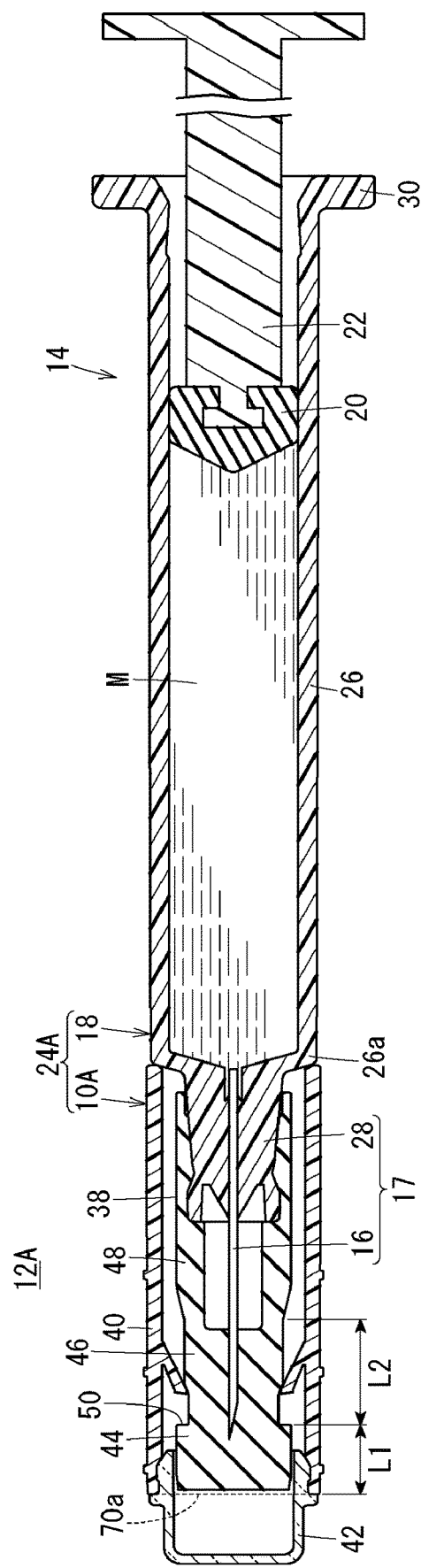
FIG. 1 is a longitudinal cross-sectional view of a prefilled syringe according to a first embodiment of the present invention.

As illustrated in FIG. 1, a prefilled syringe 12A is provided with a syringe body 14 and a cap 10A that is detachable from the syringe body 14. The syringe body 14 is provided with a needle body 16 configured to puncture the skin of a living body, a syringe outer tube 18 disposed proximal of the needle body 16, a gasket 20 slidably inserted in the syringe outer tube 18, and a pusher 22 connected to the gasket 20. In the present embodiment, the syringe outer tube 18, the needle body 16, and the cap 10A constitute a syringe assembly 24A (see FIG. 6), and the prefilled syringe 12A is assembled by the gasket 20 to which the pusher 22 is connected being inserted in a state in which the syringe outer tube 18 of the syringe assembly 24A is filled with a drug M.

Figure 2:
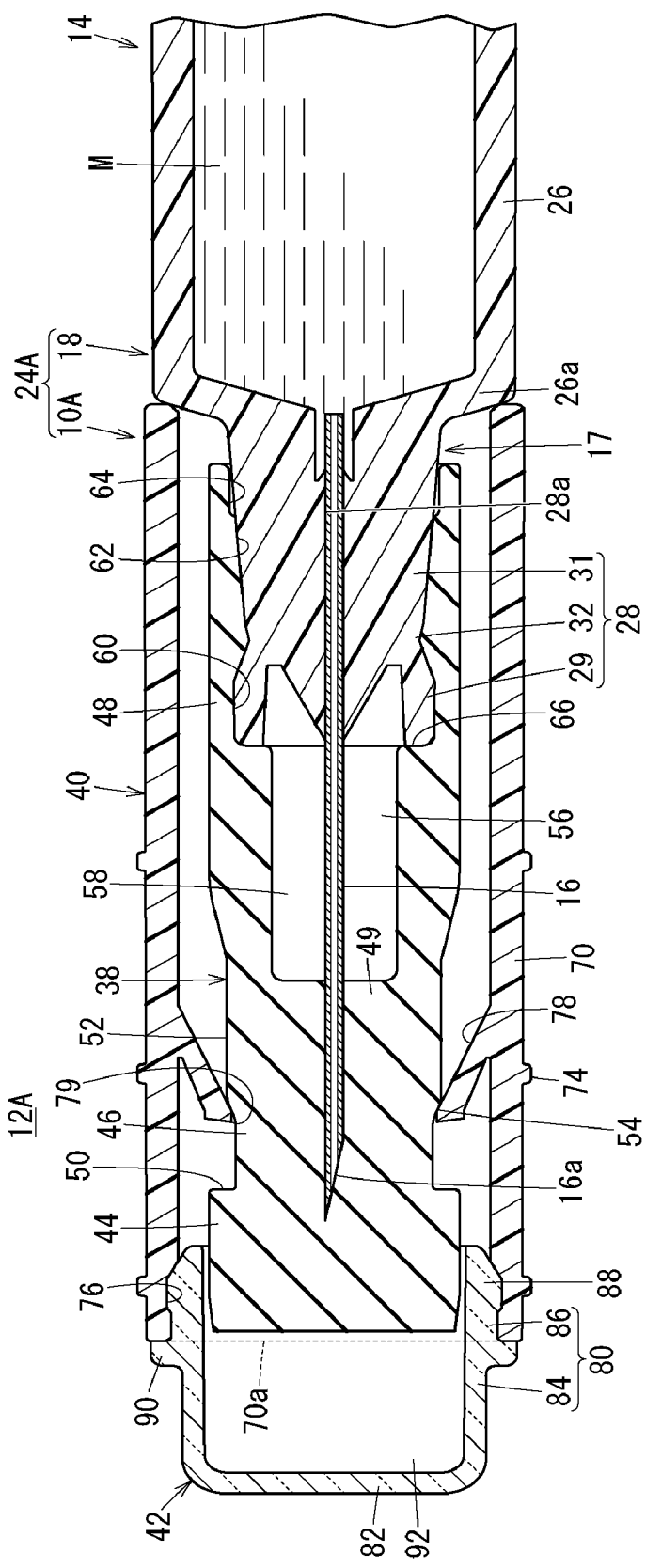
FIG. 2 is a partially-omitted and enlarged longitudinal cross-sectional view of the distal end side of the prefilled syringe illustrated in FIG. 1.

In FIG. 2, the needle body 16 is a hollow tubular member and has a sharp needle tip at the distal end of the needle body 16. A drug discharge port 16a for discharging the drug M in the syringe outer tube 18 is formed at the distal end of the needle body 16. The needle body 16 is made of, for example, a metal material such as stainless steel, aluminum or an aluminum alloy, and titanium or a titanium alloy or a hard resin material such as polyphenylene sulfide. The needle body 16 is protected by the cap 10A.

As illustrated in FIG. 1, the syringe outer tube 18 has a cylindrical body portion 26 extending in an axial direction, a needle hub 28 protruding in a distal end direction from the distal end portion of the body portion 26, and a flange portion 30 disposed in the proximal end portion of the body portion 26. The distal end portion of the body portion 26 constitutes a shoulder portion 26a, which is reduced in diameter toward the proximal end of the needle hub 28. The body portion 26, the needle hub 28, and the flange portion 30 are integrally formed.

Although the constituent material of the syringe outer tube 18 is not particularly limited, the syringe outer tube 18 may be formed of, for example, a polyolefin such as polypropylene, polyurethane, polyethylene, cyclic polyolefin, and polymethylpentene-1, a resinous material such as polyester, nylon, polycarbonate, polymethyl methacrylate (PMMA), polyetherimide (PEI), polyethersulfone, polyether ether ketone (PEEK), fluororesin, polyphenylene sulfide (PPS), and polyacetal resin (POM), a metallic material such as stainless steel, or glass.

In FIG. 2, a needle insertion hole 28a into which the proximal end side of the needle body 16 is inserted is formed in the needle hub 28. The proximal end side of the needle body 16 is fixed with respect to a wall surface constituting the needle insertion hole 28a. The needle body 16 is fixed by, for example, insert molding, high frequency-based or laser-based heat welding, or adhesion by means of an adhesive. Disposed in the needle hub 28 are a distal end head portion 29 having a constant outer diameter, a diameter-reduced portion 32 formed at the proximal end of the distal end head portion 29 and smaller in diameter than the distal end head portion 29, and a connecting portion 31 interconnecting the diameter-reduced portion 32 and the shoulder portion 26a of the body portion 26. The needle hub 28 and the needle body 16 constitute a nozzle portion 17, which has the drug discharge port 16a at the distal end of the nozzle portion 17.

In FIG. 1, the gasket 20 is configured to slide in the syringe outer tube 18 in a liquid-tight manner and in the axial direction and sends out the drug M with which the syringe outer tube 18 is filled. The distal end of the pusher 22 is connected to the gasket 20.

Figure 3:
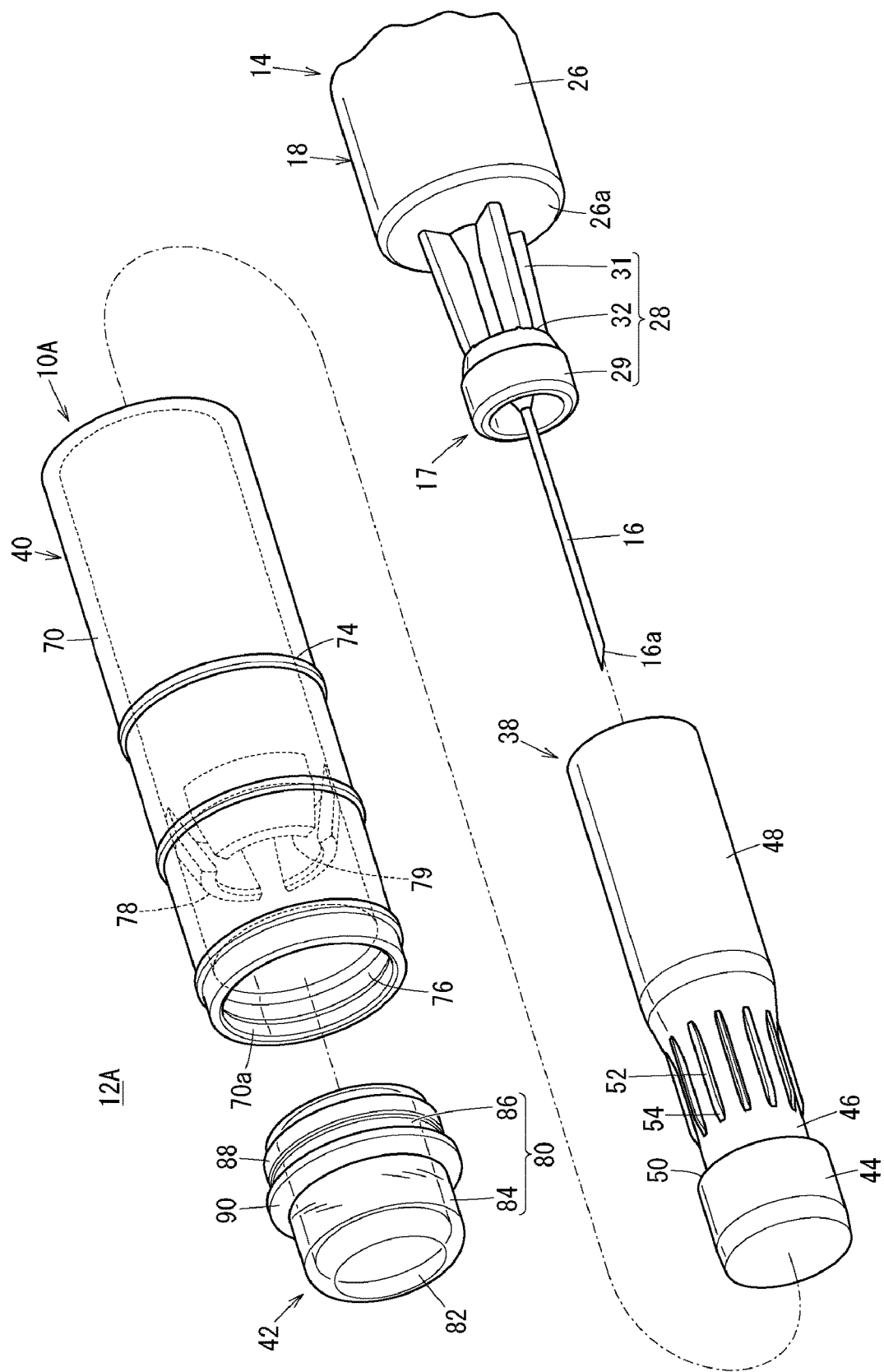
FIG. 3 is an exploded perspective view of FIG. 2.

As illustrated in FIGS. 2 and 3, the cap 10A is provided with a cap body 38 sealing the drug discharge port 16a of the nozzle portion 17 (needle body 16) in an unopened state, a cap cover 40 covering the cap body 38, and a distal end cover member 42 disposed distal of the cap cover 40.

Examples of the constituent material of the cap body 38 include rubber and a synthetic resin elastomer. Isoprene rubber, butyl rubber, latex rubber, silicone rubber, and the like can be used as the rubber. A styrene-based elastomer, an olefin-based elastomer, and the like can be used as the synthetic resin elastomer.

Figure 4:
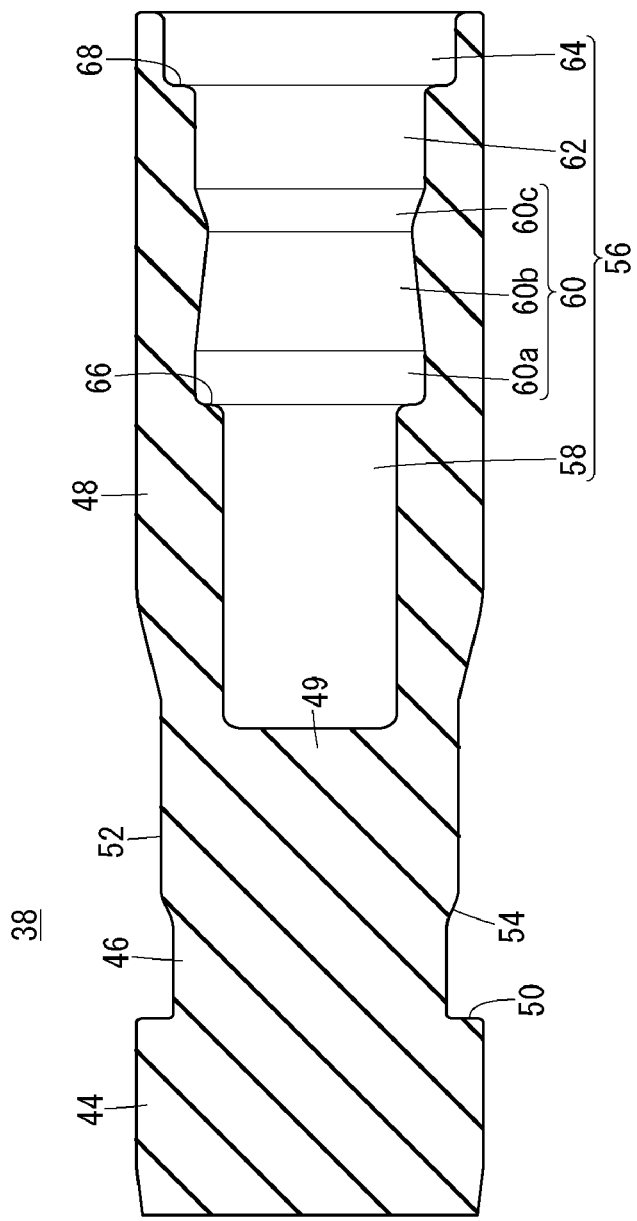
FIG. 4 is an enlarged longitudinal cross-sectional view of the cap body illustrated in FIG. 2.

As illustrated in FIGS. 2 to 4, the cap body 38 has a large-diameter distal end portion 44 (large-diameter portion) positioned in the distal end portion of the cap body 38, a small-diameter middle portion 46 disposed proximal of the large-diameter distal end portion 44, a mounting tube portion 48 (mounting portion) disposed proximal of the small-diameter middle portion 46, and a sealing portion 49 disposed in the distal end portion of the mounting tube portion 48. The large-diameter distal end portion 44 is formed in a columnar shape. The large-diameter distal end portion 44 functions as a viewing portion as described later. The outer diameter of the large-diameter distal end portion 44 is larger than the outer diameter of the distal end head portion 29 of the needle hub 28.

The small-diameter middle portion 46 has an outer diameter smaller than the outer diameter of the large-diameter distal end portion 44 over the entire length of the small-diameter middle portion 46. A proximal stepped surface 50 (locking surface) facing the proximal direction is formed in the boundary portion between the large-diameter distal end portion 44 and the small-diameter middle portion 46. A plurality of elongated ribs 52 are arranged at equal intervals in a circumferential direction on the outer peripheral surface of the small-diameter middle portion 46. The ribs 52 extend in the axial direction of the cap body 38 to the distal end of the mounting tube portion 48 from a position shifted to the proximal end side by a predetermined length from the distal end of the small-diameter middle portion 46. An inclined surface 54 is formed in the distal end portion of each rib 52. The inclined surface 54 is inclined radially inward toward the distal end direction. The height dimension of each rib 52 (length of radially outward protrusion from the small-diameter middle portion 46) is set to a height dimension at which the rib 52 does not protrude radially outward beyond the large-diameter distal end portion 44.

The mounting tube portion 48 is formed so as to be longer than the small-diameter middle portion 46. The distal end portion of the mounting tube portion 48 is a closed distal end wall portion and constitutes the sealing portion 49 configured to liquid-tightly seal the drug discharge port 16a of the nozzle portion 17 (needle body 16). The proximal end of the mounting tube portion 48 is open. An accommodating space 56 accommodating the needle body 16 and the needle hub 28 is formed in the mounting tube portion 48. The accommodating space 56 has a first hole portion 58 disposed in the distal end portion of the mounting tube portion 48, a second hole portion 60 disposed proximal of the first hole portion 58, a third hole portion 62 disposed proximal of the second hole portion 60, and a fourth hole portion 64 disposed proximal of the third hole portion 62. In other words, the first hole portion 58, the second hole portion 60, the third hole portion 62, and the fourth hole portion 64 are disposed so as to communicate with each other and in this order from the distal end of the mounting tube portion 48 toward the proximal end of the mounting tube portion 48, and the one accommodating space 56 is formed as a result.

The first hole portion 58 is formed so as to have a constant hole diameter (inner diameter) over the entire length of the first hole portion 58. The hole diameter of the first hole portion 58 is larger than the outer diameter of the needle body 16. The hole diameter of the second hole portion 60 is larger than the hole diameter of the first hole portion 58. The second hole portion 60 includes a distal end hole portion 60a formed so as to have a constant hole diameter (inner diameter), a middle hole portion 60b positioned proximal of the distal end hole portion 60a and reduced in diameter in a tapered shape toward the proximal direction, and a proximal hole portion 60c positioned proximal of the middle hole portion 60b and enlarged in diameter in a tapered shape toward the proximal direction.

The third hole portion 62 is formed so as to have a constant hole diameter (inner diameter) over the entire length of the third hole portion 62. The hole diameter of the third hole portion 62 is larger than the hole diameter of the boundary portion between the middle hole portion 60b and the proximal hole portion 60c (minimum hole diameter of the second hole portion 60). In the present embodiment, the hole diameter of the third hole portion 62 is substantially equal to the hole diameter of the distal end hole portion 60a of the second hole portion 60. The axial length of the third hole portion 62 is shorter than the axial length of the second hole portion 60. The fourth hole portion 64 is formed so as to have a constant hole diameter (inner diameter) over the entire length of the fourth hole portion 64. The hole diameter of the fourth hole portion 64 is larger than the hole diameter of the third hole portion 62 and the outer diameter of the distal end portion of the needle hub 28. The axial length of the fourth hole portion 64 is shorter than the axial length of the third hole portion 62.

In the cap body 38, a first stepped surface 66 facing the proximal direction is formed in the boundary portion between the first hole portion 58 and the second hole portion 60 and a second stepped surface 68 facing the proximal direction is formed in the boundary portion between the third hole portion 62 and the fourth hole portion 64. The distance from the distal end of the first hole portion 58 to the first stepped surface 66 is shorter than the distance from the distal end of the needle body 16 to the distal end of the needle hub 28.

The cap cover 40 is configured to have a cylindrical shape as illustrated in FIGS. 2 and 3. The cap cover 40 is made of a resin material having no transparency (substantially opaque resin material). Here, "substantially opaque" means a state in which it is difficult or impossible to view the cap body 38 in the cap cover 40 from the outside of the cap cover 40. The cap cover 40 has a cylindrical main body 70 longer than the entire length of the cap body 38. An opening 70a is formed at the distal end of the cylindrical main body 70 so that the large-diameter distal end portion 44 is exposed (protrudes) from the cylindrical main body 70.

The outer diameter of the cylindrical main body 70 is formed such that a user is allowed to easily grasp the cylindrical main body 70 with his or her fingers. A plurality of (three in FIGS. 2 and 3) non-slip portions 74 functioning as non-slip portions for a user's fingers are formed on the outer peripheral surface of the cylindrical main body 70. Each non-slip portion 74 is an annular projecting portion extending along the circumferential direction of the cylindrical main body 70. The plurality of non-slip portions 74 are disposed at equal intervals in the axial direction of the cylindrical main body 70. An annular locking groove 76 for locking the distal end cover member 42 is formed in the distal end portion of the inner peripheral surface of the cylindrical main body 70.

A plurality of (three in FIG. 3) engaging claw portions 78 (engaging portions) coming into contact with the proximal stepped surface 50 are disposed at equal intervals in the circumferential direction of the cylindrical main body 70 on the distal end side of the inner peripheral surface of the cylindrical main body 70. In other words, a predetermined gap is formed between the engaging claw portions 78 adjacent to each other in the circumferential direction. Each engaging claw portion 78 extends so as to be inclined in the distal end direction from the inner peripheral surface of the cylindrical main body 70 and is configured to be elastically deformable in the radial direction of the cylindrical main body 70. Each engaging claw portion 78 has a flat distal end surface facing the proximal stepped surface 50. Ina state in which none of the engaging claw portions 78 are elastically deformed, the hole diameter of a central hole 79 formed by the inner ends of the plurality of engaging claw portions 78 is smaller than the outer diameter of the large-diameter distal end portion 44 (see FIG. 2).

The distal end cover member 42 is formed in a substantially U-shape in longitudinal cross portion. The distal end cover member 42 covers the cap body 38 together with the cap cover 40 such that a user operating the cap 10A cannot touch the cap body 38. In other words, the distal end cover member 42 has a contact blocking function. In addition, the distal end cover member 42 functions as a detachment blocking portion blocking the cap body 38 from being detached from the opening 70a of the cap cover 40. The distal end cover member 42 has an annular portion 80 and a distal end wall 82 disposed in the distal end portion of the annular portion 80. The annular portion 80 has a proximal end portion fitted in the distal end portion of the cap cover 40 so as to protrude distally from the opening 70a of the cap cover 40.

The annular portion 80 includes an annular peripheral wall portion 84 on the distal end side and a cylindrical engagement extending portion 86 extending in the proximal direction from the proximal end of the annular peripheral wall portion 84. The inner diameter of the annular portion 80 is constant from the distal end of the annular portion 80 to the proximal end of the annular portion 80 and is slightly larger than the outer diameter of the large-diameter distal end portion 44 (see FIG. 2). Specifically, the inner diameter of the annular portion 80 is set to a range of 101% to 150% of the outer diameter of the large-diameter distal end portion 44. An annular locking claw 88 configured to be mounted on the locking groove 76 of the cap cover 40 is disposed on the outer peripheral surface of the engagement extending portion 86. An annular positioning projection 90 coming into contact with the distal end surface of the cylindrical main body 70 is disposed in the proximal end portion of the outer peripheral surface of the annular peripheral wall portion 84.

The distal end cover member 42 is integrally molded with a transparent resin material. The distal end cover member 42 may be colored although the distal end cover member 42 is colorless in the present embodiment. A receiving space 92 is disposed in the distal end cover member 42, and the large-diameter distal end portion 44 is received by the distal end wall 82 and the annular peripheral wall portion 84 in the receiving space 92 (see FIG. 2).

Basically, the prefilled syringe 12A according to the present embodiment is configured as described above. Next, a procedure for manufacturing the prefilled syringe 12A (cap 10A) will be described.

Figure 5A:
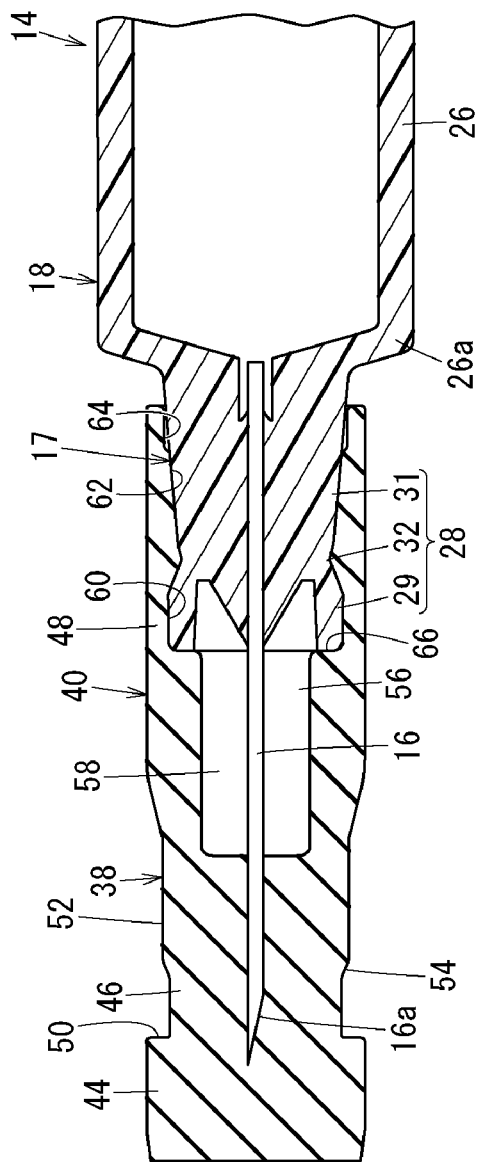
FIG. 5A is a first explanatory diagram of a procedure for manufacturing the cap.

First, the mounting tube portion 48 of the cap body 38 is fitted over the needle hub 28 as illustrated in FIG. 5A. At this time, the distal end surface of the needle hub 28 is allowed to abut against the first stepped surface 66. As a result, the inner wall surface that constitutes the second hole portion 60 of the mounting tube portion 48 is pushed out radially outward by the needle hub 28 and comes into liquid-tight contact with the outer surface of the distal end head portion 29 of the needle hub 28. In other words, the distal end head portion 29 of the needle hub 28 is fitted in a liquid-tight manner in the second hole portion 60. In other words, the second hole portion 60 functions as a fitting portion that is fitted in a liquid-tight manner with the nozzle portion 17. In addition, the needle body 16 is inserted through the first hole portion 58 and the distal end portion of the needle body 16 punctures the distal end wall portion of the mounting tube portion 48. As a result, the drug discharge port 16a is sealed by the distal end wall portion of the mounting tube portion 48 as the sealing portion 49. In other words, the nozzle portion 17 including the needle hub 28 and the needle body 16 is sealed by the distal end wall portion of the mounting tube portion 48, which is the sealing portion 49.

Subsequently, the distal end cover member 42 is mounted with respect to the cap cover 40 by the locking claw 88 of the distal end cover member 42 being fitted into the locking groove 76 of the cap cover 40. It should be noted that the mounting of the distal end cover member 42 with respect to the cap cover 40 may be performed after the cap cover 40 is completely mounted with respect to the cap body 38.

Figure 5B:
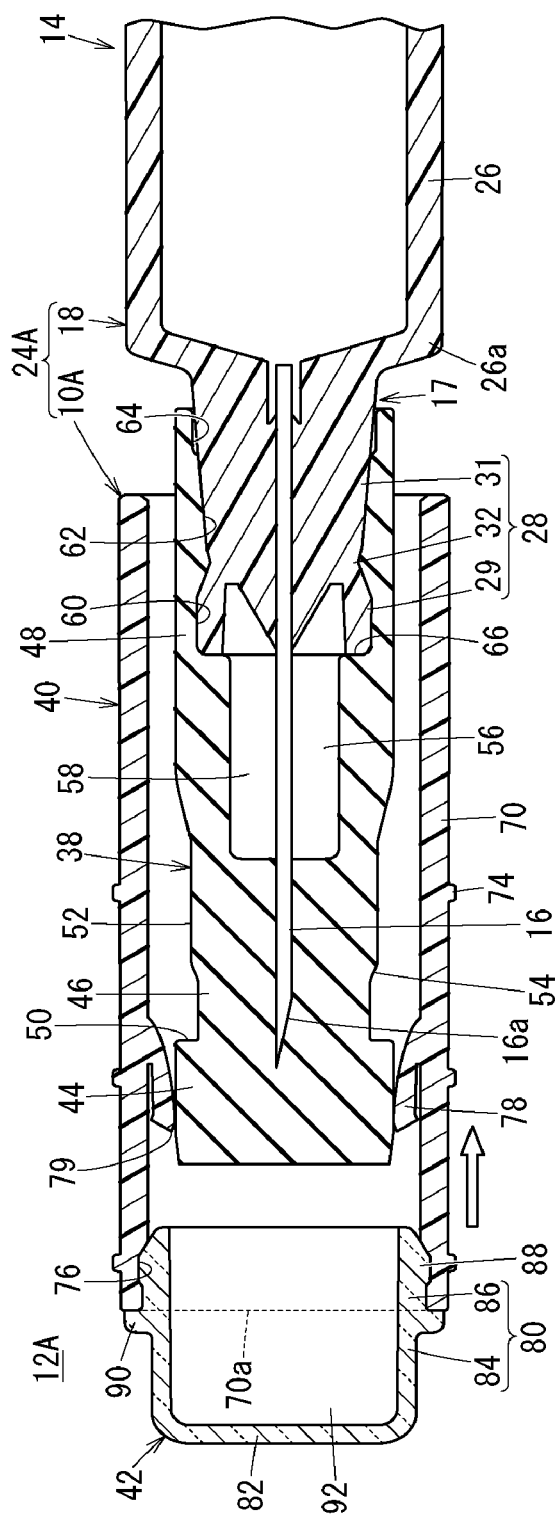
FIG. 5B is a second explanatory diagram of the procedure for manufacturing the cap.
Figure 6:
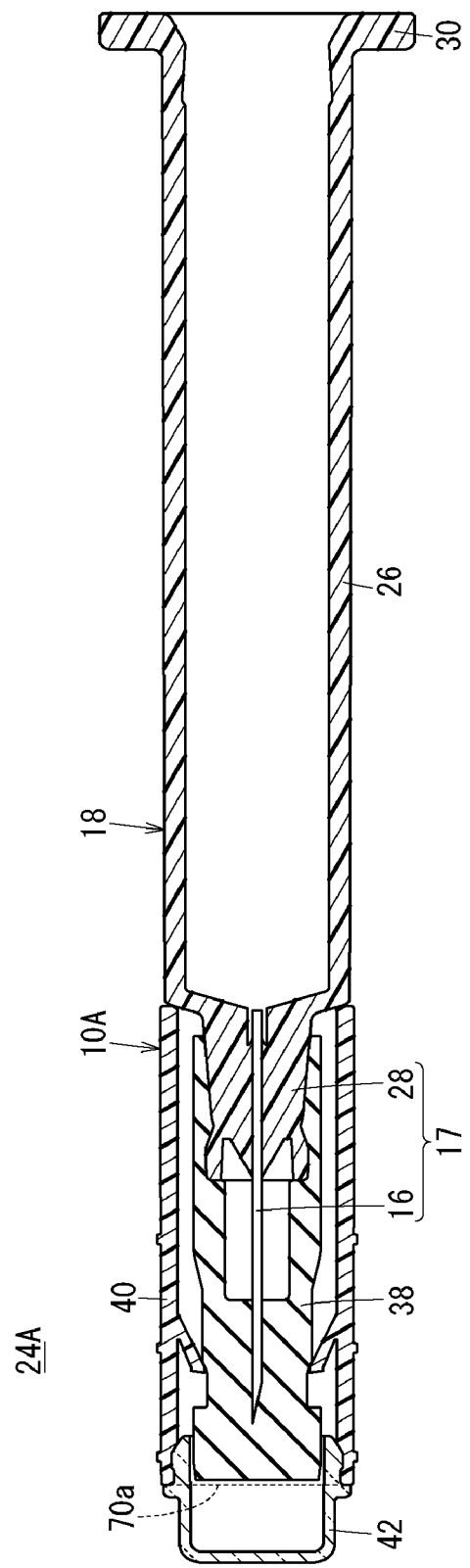
FIG. 6 is a longitudinal cross-sectional view of a syringe assembly according to the first embodiment.

Subsequently, the large-diameter distal end portion 44 is inserted from the proximal end side of the cylindrical main body 70 as illustrated in FIG. 5B. Then, each engaging claw portion 78 is pressed by the large-diameter distal end portion 44. As a result, each engaging claw portion 78 is bent (elastically deformed) radially outward such that the hole diameter of the central hole 79 formed by the respective inner ends of the engaging claw portions 78 increases, and thus the large-diameter distal end portion 44 climbs over each engaging claw portion 78 and moves in the distal end direction beyond each engaging claw portion 78. Then, the mounting of the cap cover 40 with respect to the cap body 38 is completed by the proximal end portion of the cylindrical main body 70 being brought into contact with or close to the shoulder portion 26a of the body portion 26. Manufactured as a result is the syringe assembly 24A provided with the syringe outer tube 18 and the cap 10A as illustrated in FIG. 6.

In a state in which the syringe assembly 24A is assembled as described above, that is, in a state in which the cap 10A is completely mounted on the syringe body 14, the cap body 38 is positioned at a first position, where the large-diameter distal end portion 44 is proximal of the opening 70a of the cylindrical main body 70. Specifically, the distal end of the cap body 38 is positioned more proximally than the opening 70a of the cylindrical main body 70 and in the engagement extending portion 86 of the distal end cover member 42. As a result, the outer peripheral portion of the large-diameter distal end portion 44, which is a viewing portion, is hidden in the substantially opaque cylindrical main body 70 and cannot be viewed from the outside. In addition, the mounting tube portion 48 as a mounting portion is in a state of being mounted on the needle hub 28 as a part of the nozzle portion 17, and the sealing portion 49 (distal end wall portion) of the mounting tube portion 48 seals the drug discharge port 16a formed at the distal end of the needle body 16, which is a part of the nozzle portion 17.

In a state in which the cap body 38 of the cap 10A mounted on the syringe body 14 is at the first position, a distance L1 from the proximal stepped surface 50 to the opening 70a of the cylindrical main body 70 is shorter than an axial length L2 of the small-diameter middle portion 46. In addition, each engaging claw portion 78 is separated more proximally than the proximal stepped surface 50. It should be noted that each engaging claw portion 78 may abut against the proximal stepped surface 50.

The proximal end portion of the cylindrical main body 70 of the cap cover 40 is configured to abut against the shoulder portion 26a of the body portion 26 of the syringe body 14 in the state in which the cap body 38 of the cap 10A mounted on the syringe body 14 is at the first position. As a result, movement of the cap cover 40 in the proximal direction with respect to the syringe body 14 is restricted, and the cap body 38 at the first position is inhibited from being displaced to a second position.

The prefilled syringe 12A illustrated in FIG. 1 is manufactured by the syringe outer tube 18 of the syringe assembly 24A being filled with the drug M and the gasket 20 and the pusher 22 being mounted.

Next, operation for opening the cap 10A that is in the unopened state and a recap operation will be described. The recap operation is to reinstall the cap 10A on the syringe body 14 after removal of the cap 10A from the syringe body 14.

Figure 7A:
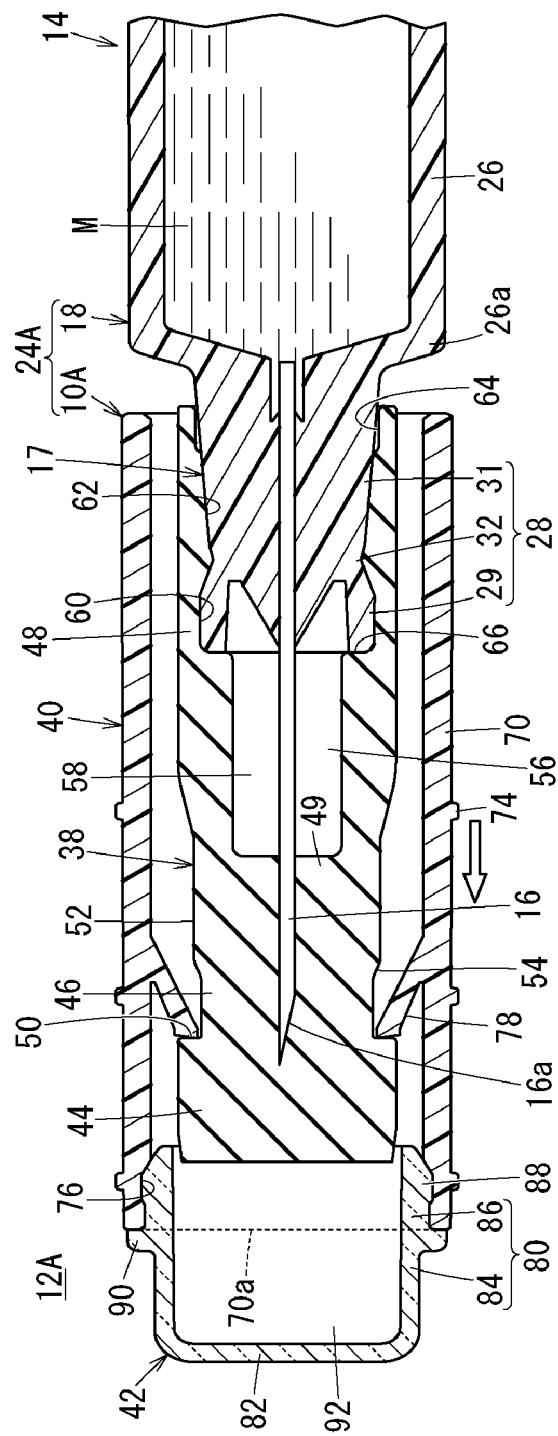
FIG. 7A is a first explanatory diagram of opening operation for the cap.
Figure 7B:
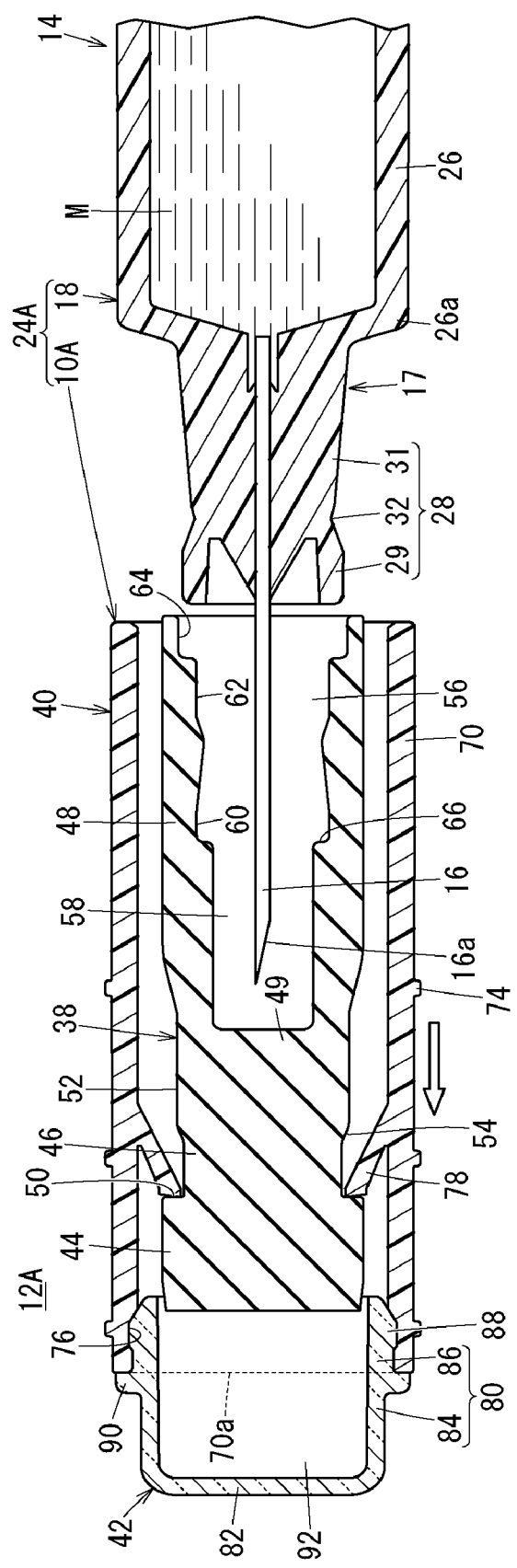
FIG. 7B is a second explanatory diagram of the opening operation for the cap.

A user who wishes to open the cap 10A displaces the cap cover 40 relative to the syringe body 14 in the distal end direction as illustrated in FIG. 7A. Then, the cap cover 40 is displaced in the distal end direction with respect to the cap body 38, and thus each engaging claw portion 78 comes into contact with the proximal stepped surface 50. Once the cap cover 40 is further displaced relative to the syringe body 14 in the distal end direction as illustrated in FIG. 7B, the proximal stepped surface 50 is pressed in the distal end direction by each engaging claw portion 78, the needle hub 28 is disengaged from the second hole portion 60 and the third hole portion 62 of the cap body 38, and the distal end portion of the needle body 16 comes out of the small-diameter middle portion 46. The cap 10A is opened as a result.

In the open cap 10A, in a distal direction displacement of the cap body 38 with respect to the cap cover 40 is restricted by the large-diameter distal end portion 44 coming into contact with the distal end wall 82 and proximal displacement of the cap body 38 with respect to the cap cover 40 is restricted by the engaging claw portion 78 coming into contact with the proximal stepped surface 50. In other words, the cap body 38 is not detached from the cap cover 40.

Figure 8A:
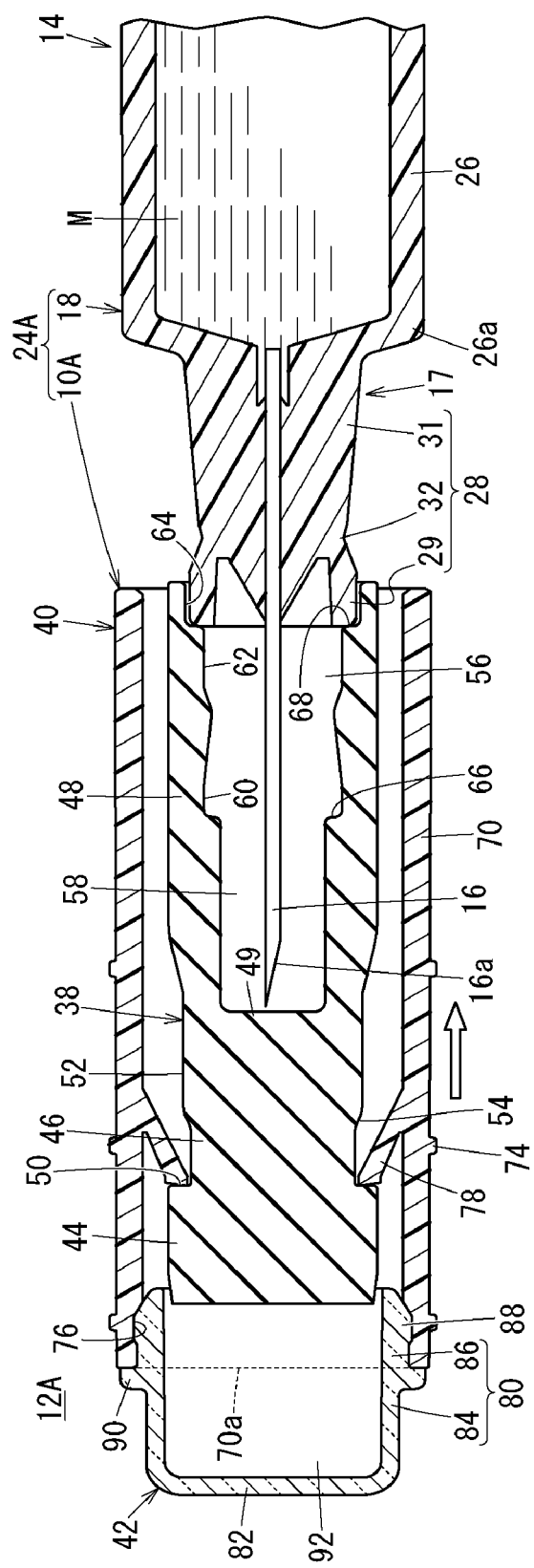
FIG. 8A is a first explanatory diagram of a recap operation for the cap.

As illustrated in FIG. 8A, in a case where the syringe body 14 is recapped with the cap 10A after opening, the needle body 16 and the needle hub 28 are inserted into the accommodating space 56 from the proximal direction of the cap body 38 by the cap cover 40 being displaced relative to the syringe body 14 in the proximal direction. Then, the second stepped surface 68 of the cap body 38 comes into contact with the distal end surface of the needle hub 28 and is pressed in the distal end direction and the large-diameter distal end portion 44 protrudes in the distal end direction beyond the opening 70a of the cylindrical main body 70. In other words, once the mounting tube portion 48 of the cap 10A is brought close to the nozzle portion 17 of the syringe body 14 in a state in which the cap body 38 is disposed at the first position, the mounting tube portion 48 of the cap body 38 is pressed in the distal end direction by the needle hub 28 (nozzle portion 17) of the syringe body 14 and the cap body 38 is displaced from the first position to the second position. As described above, the second stepped surface 68 of the cap body 38 functions as an abutting portion that abuts against the nozzle portion 17 when the syringe body 14 is recapped with the cap 10A after opening.

Figure 8B:
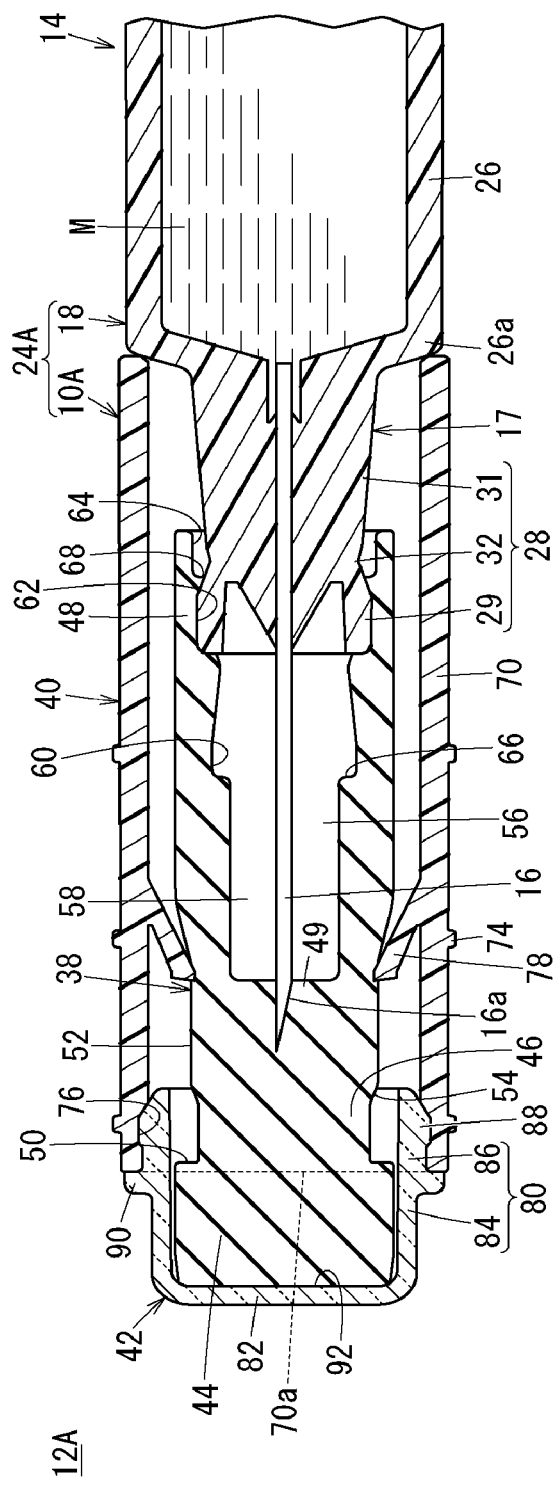
FIG. 8B is a second explanatory diagram of the recap operation for the cap.

By the cap cover 40 being further displaced relative to the syringe body 14 in the proximal direction with the distal end surface of the large-diameter distal end portion 44 abutting against the distal end wall 82 as illustrated in FIG. 8B, the distal end portion of the needle hub 28 climbs over the second stepped surface 68 and is fitted into the third hole portion 62 and the distal end portion of the needle body 16 punctures the small-diameter middle portion 46. As a result, the syringe body 14 is recapped with the cap 10A.

At this time, the cap body 38 is positioned at the second position, where the large-diameter distal end portion 44 is received in the receiving space 92 formed by the annular peripheral wall portion 84 and the distal end wall 82. Then, the outer peripheral portion of the large-diameter distal end portion 44 becomes visible through the substantially transparent annular peripheral wall portion 84. In other words, as a result of displacement of the cap body 38 from the first position to the second position, the outer peripheral portion of the large-diameter distal end portion 44 changes in appearance from a state in which the outer peripheral portion is covered with the substantially opaque cylindrical main body 70 and invisible to a state in which the outer peripheral portion is visible through the substantially transparent annular peripheral wall portion 84. In addition, since the wall surface that constitutes the third hole portion 62 is pushed out radially outward by the needle hub 28, the wall surface comes into liquid-tight contact with the outer peripheral surface of the distal end portion of the needle hub 28. Further, the drug discharge port 16*a* at the distal end of the needle body 16 is sealed by the sealing portion 49.

According to the present embodiment, when the mounting tube portion 48 of the cap 10A removed from the syringe body 14 is close to the nozzle portion 17 of the syringe body 14 with the cap body 38 disposed at the first position, the mounting tube portion 48 is pressed in the distal end direction by the nozzle portion 17 of the syringe body 14 such that the cap body 38 is displaced from the first position to the second position and the appearance of the outer peripheral portion of the large-diameter distal end portion 44 changes as the large-diameter distal end portion 44 protrudes from the opening 70*a* as a result of the displacement of the cap body 38 from the first position to the second position. As a result, a user can easily and reliably discriminate between the unopened state of the cap 10A with respect to the syringe body 14 having the needle body 16 and a recapped state in which the cap 10A is remounted on the syringe body 14 after removal from the syringe body 14, that is, an opened state.

As illustrated in FIG. 8B, the cylindrical main body 70 and the distal end cover member 42 cover the cap body 38 such that a user operating the cap 10A in the recapped state cannot touch the cap body 38. Accordingly, it is possible to inhibit a user from accidentally returning the cap body 38 at the second position to the first position in the recapped state.

Further, since the distal end of the annular peripheral wall portion 84 is closed by the distal end wall 82, it is possible to more reliably inhibit a user from accidentally returning the cap body 38 at the second position to the first position in the recapped state.

In the present embodiment, the distal end cover member 42 is transparent and the cylindrical main body 70 is substantially opaque. Accordingly, the outer peripheral portion of the large-diameter distal end portion 44 is hidden in the cylindrical main body 70 and substantially invisible when the cap body 38 is at the first position and the outer peripheral portion of the large-diameter distal end portion 44 becomes visible through the distal end cover member 42 when the cap body 38 is at the second position.

The engagement extending portion 86 is engaged with the inner peripheral surface of the cylindrical main body 70 in the structure described above. Accordingly, it is possible to inhibit a user from accidentally removing the distal end cover member 42 from the cylindrical main body 70.

Further, Movement of the distal end cover member 42 in the proximal direction with respect to the cylindrical main body 70 is inhibited by the positioning projection 90 abutting against the distal end surface of the cylindrical main body 70, and thus it is possible to reliably form the receiving space 92, which receives the large-diameter distal end portion 44 protruding in the distal end direction from the opening 70*a* of the cylindrical main body 70.

In the present embodiment, the inner diameter of the annular portion 80 is constant from the distal end of the annular portion 80 to the proximal end of the annular portion 80 and is slightly larger than the outer diameter of the large-diameter distal end portion 44. When the cap body 38 is at the first position, at least the distal end of the large-diameter distal end portion 44 is positioned in the annular portion 80. Accordingly, it is possible to smoothly displace the cap body 38 from the first position to the second position. In other words, it is possible to suppress the cap body 38 being caught on the inner surface of the distal end cover member 42 during the displacement from the first position to the second position.

The outer diameter of the large-diameter distal end portion 44 is larger than the outer diameter of the distal end head portion 29 of the needle hub 28 (part of the nozzle portion 17 where the mounting tube portion 48 is fitted), and thus the outer peripheral portion of the large-diameter distal end portion 44 as a viewing portion can be easily viewed.

In the present embodiment, detachment of the cap body 38 with in a proximal end direction respect to the cap cover 40 can be inhibited by engagement of the engaging claw portion 78 with the proximal stepped surface 50.

The proximal stepped surface 50 is pressed in the distal end direction by the engaging claw portion 78 and the cap body 38 is removed from the syringe body 14 by the cap cover 40 being displaced relative to the syringe body 14 in the distal end direction. Accordingly, the cap 10A can be easily removed from the syringe body 14.

Further, when the cap 10A is manufactured, the cap body 38 is inserted from the proximal direction of the cap cover 40 after the cap body 38 is attached to the syringe body 14. As a result, the large-diameter distal end portion 44 climbs over the engaging claw portion 78 while elastically deforming the engaging claw portion 78 radially outward. Accordingly, assembly of the cap cover 40 with respect to the cap body 38 can be performed with ease.

The plurality of engaging claw portions 78 are disposed along the circumferential direction of the cylindrical main body 70, and thus detachment of the cap body 38 in the proximal end direction with respect to the cap cover 40 can be effectively inhibited. Further, since a predetermined gap is formed between the engaging claw portions 78 adjacent to each other in the circumferential direction, each engaging claw portion 78 can be elastically deformed with reliability during manufacturing of the cap 10A.

In the present embodiment, the hole diameter of the central hole 79 formed by the inner ends of the plurality of engaging claw portions 78 is smaller than the outer diameter of the large-diameter distal end portion 44. Accordingly, each engaging claw portion 78 can be reliably brought into contact with the proximal stepped surface 50.

The large-diameter distal end portion 44 functioning as a viewing portion is disposed in the distal end portion of the cap body 38, and thus the outer peripheral portion of the large-diameter distal end portion 44 (viewing portion) can be easily viewed and an increase in the outer diameter of the proximal end side of the cap body 38 can be suppressed.

Further, the inner diameter of the annular portion 80 is set to a range of 101% to 150% of the outer diameter of the large-diameter distal end portion 44. Accordingly, it is possible to more smoothly displace the cap body 38 from the first position to the second position while relatively increasing the outer diameter of the large-diameter distal end portion 44.

Moreover, the axial length L2 of the small-diameter middle portion 46 is longer than the distance L1 from the proximal stepped surface 50 to the opening 70*a* of the cylindrical main body 70 in a state in which the cap body 38 is at the first position (see FIG. 1). Accordingly, it is possible to inhibit the small-diameter middle portion 46 from being caught by the engaging claw portion 78 and inhibit the displacement from being hindered during the displacement of the cap body 38 from the first position to the second position.

In the present embodiment, the drug discharge port 16a is sealed in a liquid-tight manner by the distal end portion of the needle body 16 inserted through the first hole portion 58 puncturing the distal end wall portion of the mounting tube portion 48 as the sealing portion 49 and the distal end portion of the needle hub 28 is liquid-tightly fitted in the second hole portion 60 and the third hole portion 62 when the cap body 38 is at the first position. Accordingly, the drug M can be reliably sealed in the syringe body 14 in the unopened state of the cap 10A.

When the cap body 38 is at the first position, the wall surface that constitutes the second hole portion 60 abuts against the diameter-reduced portion 32 of the needle hub 28. Accordingly, it is possible to inhibit the mounting tube portion 48 from accidentally coming out of the needle hub 28 in the unopened state of the cap 10A.

Further, when the cap body 38 is at the second position as illustrated in FIG. 8B, the drug discharge port 16a is sealed in a liquid-tight manner by the distal end portion of the needle body 16 puncturing the sealing portion 49 and the distal end portion of the needle hub 28 is fitted in the third hole portion 62 without being fitted in the second hole portion 60. Accordingly, it is possible to inhibit needle tip exposure attributable to an accidental disengagement of the cap 10A from the syringe body 14 in the recapped state of the cap 10A.

The distal end of the large-diameter distal end portion 44 abuts against the distal end wall 82 when the cap body 38 is at the second position. Accordingly, the distal end portion of the needle hub 28 can be reliably fitted into the third hole portion 62.

Second Embodiment

Next, a prefilled syringe 12B according to a second embodiment of the present invention will be described. It should be noted that components of the prefilled syringe 12B according to the second embodiment that are identical to those of the prefilled syringe 12A according to the first embodiment are denoted by the same reference numerals and detailed descriptions of the components are omitted. In the present embodiment, configurations similar to those of the prefilled syringe 12A according to the first embodiment have similar actions and effects. This also applies to a third embodiment to be described later.

Figure 9:
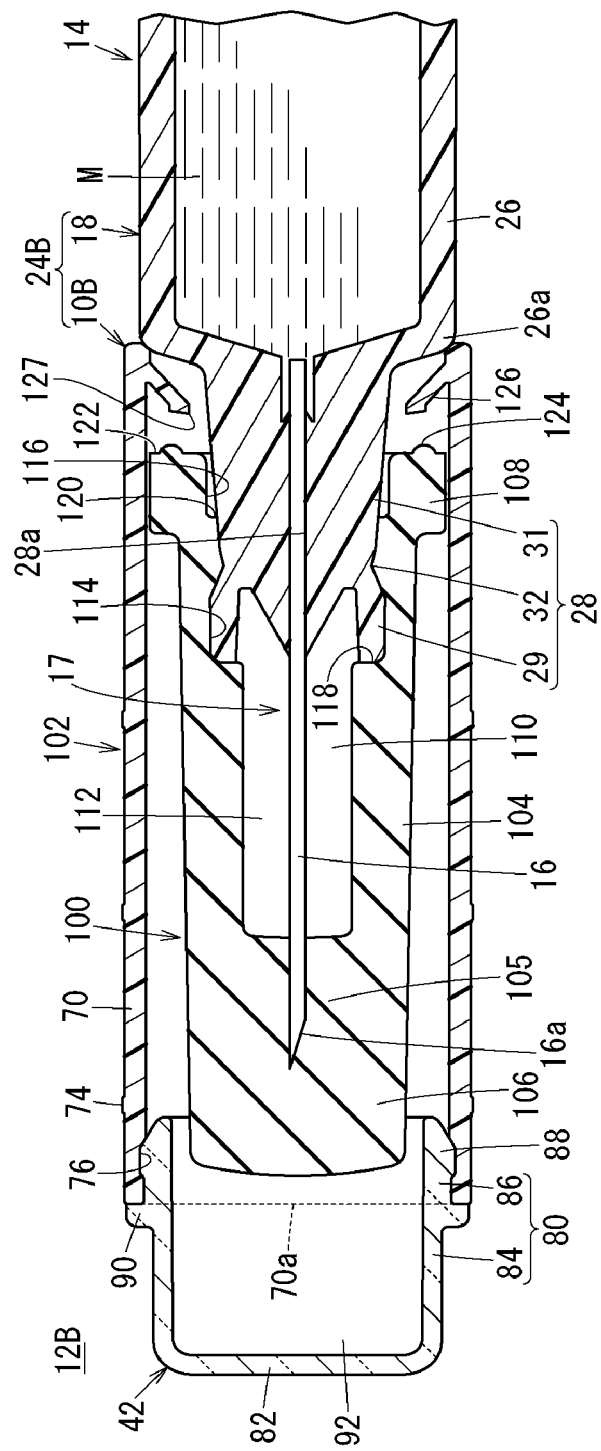
FIG. 9 is a partially-omitted and enlarged longitudinal cross-sectional view of the distal end portion of a prefilled syringe according to a second embodiment of the present invention.
Figure 10:
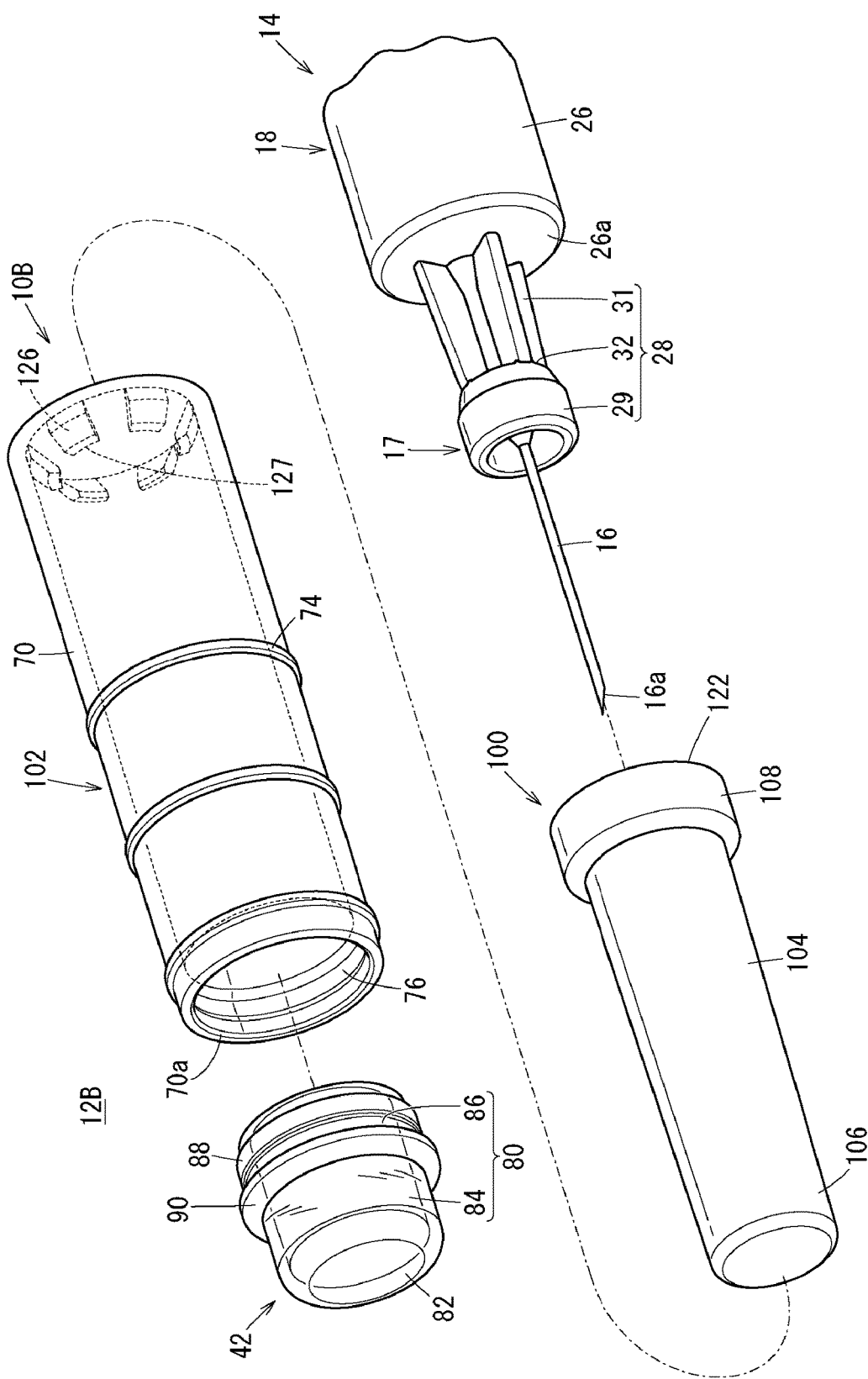
FIG. 10 is an exploded perspective view of FIG. 9.

As illustrated in FIGS. 9 and 10, the prefilled syringe 12B is provided with the syringe body 14 and a cap 10B detachable from the syringe body 14. In the present embodiment, the syringe outer tube 18, the needle body 16, and the cap 10B constitute a syringe assembly 24B.

The cap 10B has a cap body 100, a cap cover 102, and the distal end cover member 42. The constituent material of the cap body 100 can be similar to the material of the cap body 38 described above.

The cap body 100 has a mounting tube portion 104 where the needle hub 28 is mounted, a distal end extending portion 106 extending in the distal end direction from the distal end of the mounting tube portion 104, and a large-diameter proximal end portion 108 disposed in the proximal end portion of the mounting tube portion 104. The distal end portion of the mounting tube portion 104 is a closed sealing portion 105 (distal end wall portion). The distal end extending portion 106 is configured to have a columnar shape. The distal end extending portion 106 functions as a viewing portion as described later. The outer diameter of the distal end extending portion 106 is larger than the distal end outer diameter of the needle hub 28.

Figure 11:
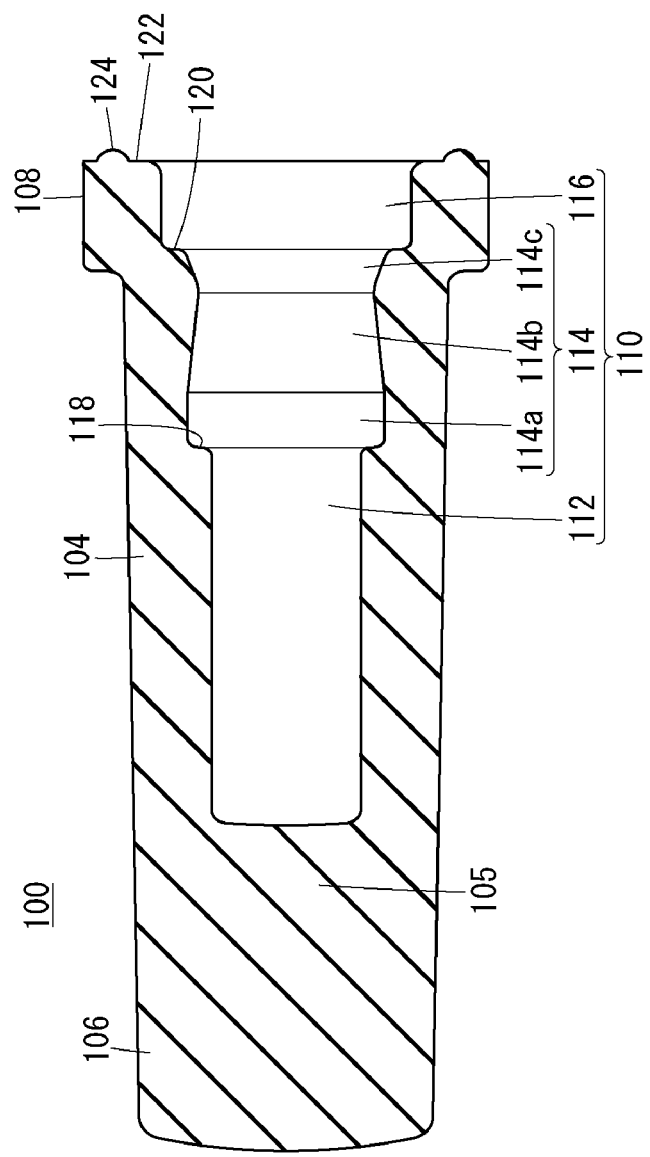
FIG. 11 is an enlarged cross-sectional view of the cap body illustrated in FIG. 9.

As illustrated in FIG. 11, an accommodating space 110 accommodating the needle body 16 and the needle hub 28 is formed in the mounting tube portion 104. The accommodating space 110 has a first hole portion 112 disposed in the distal end portion of the mounting tube portion 104, a second hole portion 114 disposed proximal of the first hole portion 112, and a third hole portion 116 disposed proximal of the second hole portion 114. In other words, the first hole portion 112, the second hole portion 114, and the third hole portion 116 are disposed so as to communicate with each other and in this order from the distal end of the mounting tube portion 104 toward the proximal end of the mounting tube portion 104, and the one accommodating space 110 is formed as a result.

The first hole portion 112 is formed so as to have a constant hole diameter (inner diameter) over the entire length of the first hole portion 112. The hole diameter of the first hole portion 112 is larger than the outer diameter of the needle body 16. The hole diameter of the second hole portion 114 is larger than the hole diameter of the first hole portion 112. The second hole portion 114 includes a distal end hole portion 114a formed so as to have a constant hole diameter (inner diameter), a middle hole portion 114b positioned proximal of the distal end hole portion 114a and reduced in diameter in a tapered shape toward the proximal direction, and a proximal hole portion 114c positioned proximal of the middle hole portion 114b and enlarged in diameter in a tapered shape toward the proximal direction. The third hole portion 116 is formed so as to have a constant hole diameter (inner diameter) over the entire length of the third hole portion 116. The hole diameter of the third hole portion 116 is larger than the hole diameter of the second hole portion 114. The axial length of the third hole portion 116 is shorter than the axial length of the second hole portion 114.

In the cap body 100, a first stepped surface 118 facing the proximal direction is formed in the boundary portion between the first hole portion 112 and the second hole portion 114 and a second stepped surface 120 facing the proximal direction is formed in the boundary portion between the second hole portion 114 and the third hole portion 116. The distance from the distal end of the first hole portion 112 to the first stepped surface 118 is shorter than the distance from the distal end of the needle body 16 to the distal end of the needle hub 28. The distance from the distal end of the first hole portion 112 to the second stepped surface 120 is shorter than the distance from the distal end of the needle body 16 to the distal end of the needle hub 28.

A plurality of support projections 124 protruding in the proximal direction are disposed at equal intervals in the circumferential direction on a proximal end surface 122 of the large-diameter proximal end portion 108. Each support projection 124 has an outer surface formed in a circular arc shape in transverse cross portion.

The cap cover 102 is configured to have a cylindrical shape as illustrated in FIGS. 9 and 10. The cap cover 102 is made of a resin material having no transparency (substantially opaque resin material). The cap cover 102 has the cylindrical main body 70 longer than the entire length of the cap body 100. The non-slip portion 74 is formed on the outer peripheral surface of the cylindrical main body 70. A plurality of (six in FIG. 10) engaging claw portions 126

(engaging portions) coming into contact with the proximal end surface 122 (locking surface) of the large-diameter proximal end portion 108 are disposed at equal intervals in the circumferential direction of the cylindrical main body 70 in the proximal end portion of the inner peripheral surface of the cylindrical main body 70. In other words, a predetermined gap is formed between the engaging claw portions 126 adjacent to each other in the circumferential direction. Each engaging claw portion 126 extends so as to be inclined in the distal end direction from the inner peripheral surface of the cylindrical main body 70 and is configured to be elastically deformable in the radial direction of the cylindrical main body 70. Each engaging claw portion 126 has a flat distal end surface. In a state in which none of the engaging claw portions 126 are elastically deformed, the hole diameter of a central hole 127 formed by the inner ends of the plurality of engaging claw portions 126 is smaller than the outer diameter of the large-diameter proximal end portion 108.

Figure 12A:
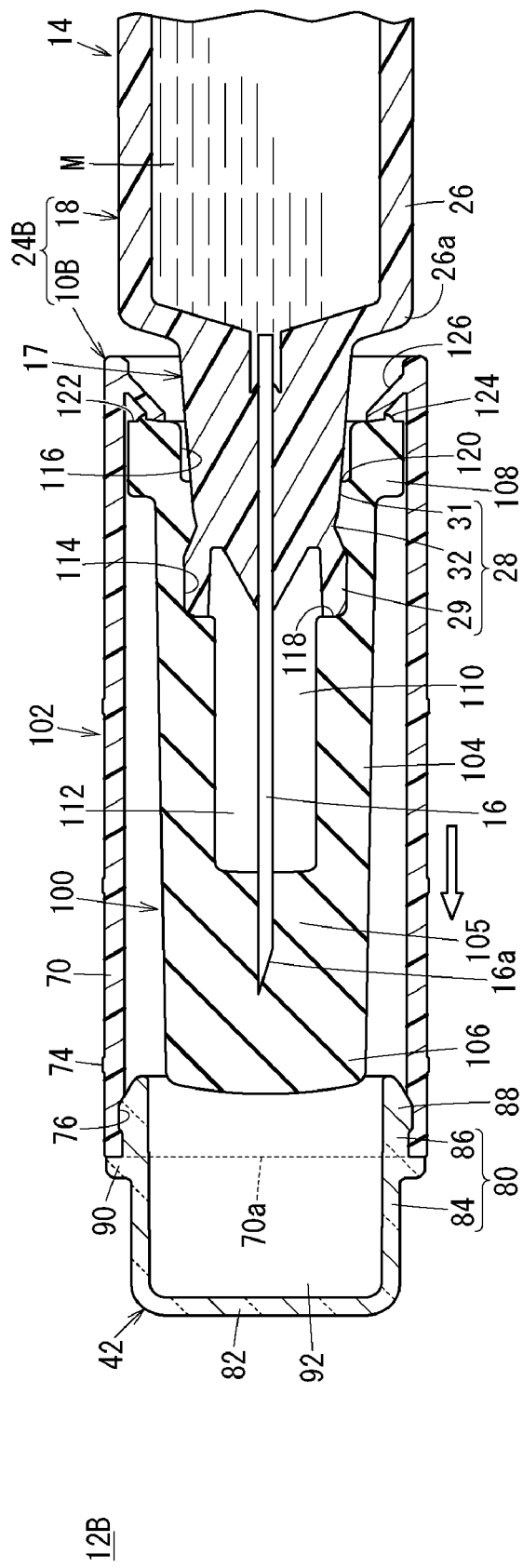
FIG. 12A is a first explanatory diagram of opening operation for the cap illustrated in FIG. 9.

The engaging claw portion 126 comes into contact with the proximal end surface 122 of the large-diameter proximal end portion 108 in a state in which the support projection 124 is pressed radially outward (see FIG. 12A). As a result, the cap cover 102 can be stably supported with respect to the cap body 100.

A procedure for manufacturing the prefilled syringe 12B (cap 10B) according to the present embodiment is similar to the procedure for manufacturing the prefilled syringe 12A (cap 10A) according to the first embodiment.

In other words, the mounting tube portion 104 of the cap body 100 is fitted over the needle hub 28 and the distal end extending portion 106 is inserted from the proximal end side of the cap cover 102 with the distal end cover member 42 mounted. Then, each engaging claw portion 126 is pressed by the large-diameter proximal end portion 108. As a result, each engaging claw portion 126 is bent (elastically deformed) radially outward such that the inner diameter of the central hole 127 formed by the respective inner ends of the engaging claw portions 126 increases, and thus the large-diameter proximal end portion 108 climbs over each engaging claw portion 126 and moves in the distal end direction beyond each engaging claw portion 126. Then, installation of the cap cover 102 with respect to the cap body 100 is completed by the proximal end portion of the cylindrical main body 70 being brought into contact with or close to the shoulder portion 26a of the body portion 26. The syringe assembly 24B is manufactured as a result. The prefilled syringe 12B is manufactured by the syringe outer tube 18 of the syringe assembly 24B being filled with the drug M and the gasket 20 and the pusher 22 being mounted.

In the present embodiment, the needle hub 28 is fitted into the second hole portion 114, the distal end portion of the needle body 16 punctures the sealing portion 105, and the drug discharge port 16a is sealed as a result in the unopened state of the cap 10B. In other words, the nozzle portion 17 including the needle hub 28 and the needle body 16 is sealed by the distal end wall portion of the mounting tube portion 104, which is the sealing portion 105.

The cap body 100 is positioned at the first position, where the distal end portion of the cap body 100 is proximal of the opening 70a of the cylindrical main body 70. Specifically, the distal end of the cap body 100 is positioned more proximally than the opening 70a of the cylindrical main body 70 and in the engagement extending portion 86 of the distal end cover member 42. As a result, the outer peripheral portion of the distal end extending portion 106, which is a viewing portion, is hidden in the substantially opaque cylindrical main body 70 and cannot be viewed from the outside.

Next, operation for opening the cap 10B that is in the unopened state will be described.

A user who wishes to open the cap 10B displaces the cap cover 102 relative to the syringe body 14 in the distal end direction as illustrated in FIG. 12A. Then, the cap cover 102 is displaced in the distal end direction with respect to the cap body 100, and thus each engaging claw portion 126 comes into contact with the proximal end surface 122 of the large-diameter proximal end portion 108. At this time, the engaging claw portion 126 is pressed radially inward by the support projection 124, and thus contact with the proximal end surface 122 becomes reliable. As a result, the cap cover 102 is stably supported with respect to the cap body 100.

Figure 12B:
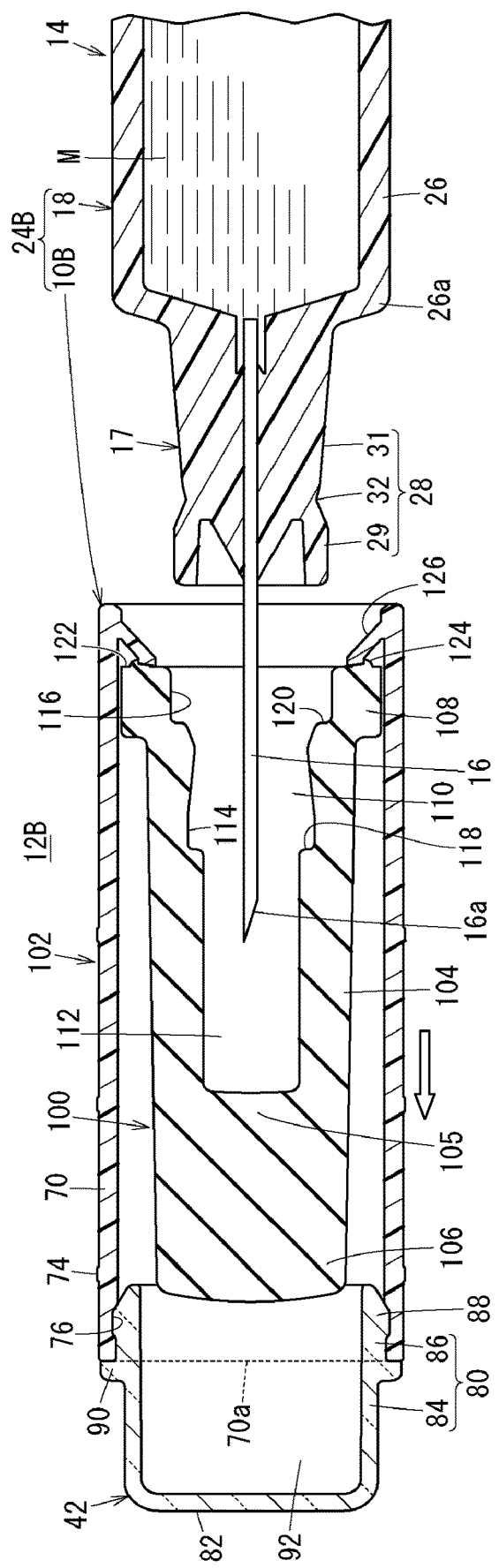
FIG. 12B is a second explanatory diagram of the opening operation for the cap.

Once the cap cover 102 is further displaced relative to the syringe body 14 in the distal end direction as illustrated in FIG. 12B, the proximal end surface 122 of the large-diameter proximal end portion 108 is pressed in the distal end direction by each engaging claw portion 126, the needle hub 28 is disengaged from the second hole portion 114 of the cap body 100, and the distal end portion of the needle body 16 comes out of the sealing portion 105. The cap 10B is opened as a result. In the open cap 10B, the proximal end surface 122 is locked in the engaging claw portion 126, and thus proximal displacement of the cap body 100 with respect to the cylindrical main body 70 is restricted.

As illustrated in FIG. 13A, in a case where the syringe body 14 is to be recapped with the cap 10B after opening, the needle body 16 and the needle hub 28 are inserted into the accommodating space 110 from the proximal direction of the cap body 100 by the cap cover 102 being displaced relative to the syringe body 14 in the proximal direction. Then, the second stepped surface 120 of the cap body 100 comes into contact with the distal end surface of the needle hub 28 and is pressed in the distal end direction and the distal end extending portion 106 of the cap body 100 protrudes in the distal end direction beyond the opening 70a of the cylindrical main body 70. In other words, once the mounting tube portion 104 of the cap 10B is brought close to the needle hub 28 (nozzle portion 17) of the syringe body 14 in a state in which the cap body 100 is disposed at the first position, the mounting tube portion 104 of the cap body 100 is pressed in the distal end direction by the needle hub 28 (nozzle portion 17) of the syringe body 14 and the cap body 100 is displaced from the first position to the second position.

Figure 13B:
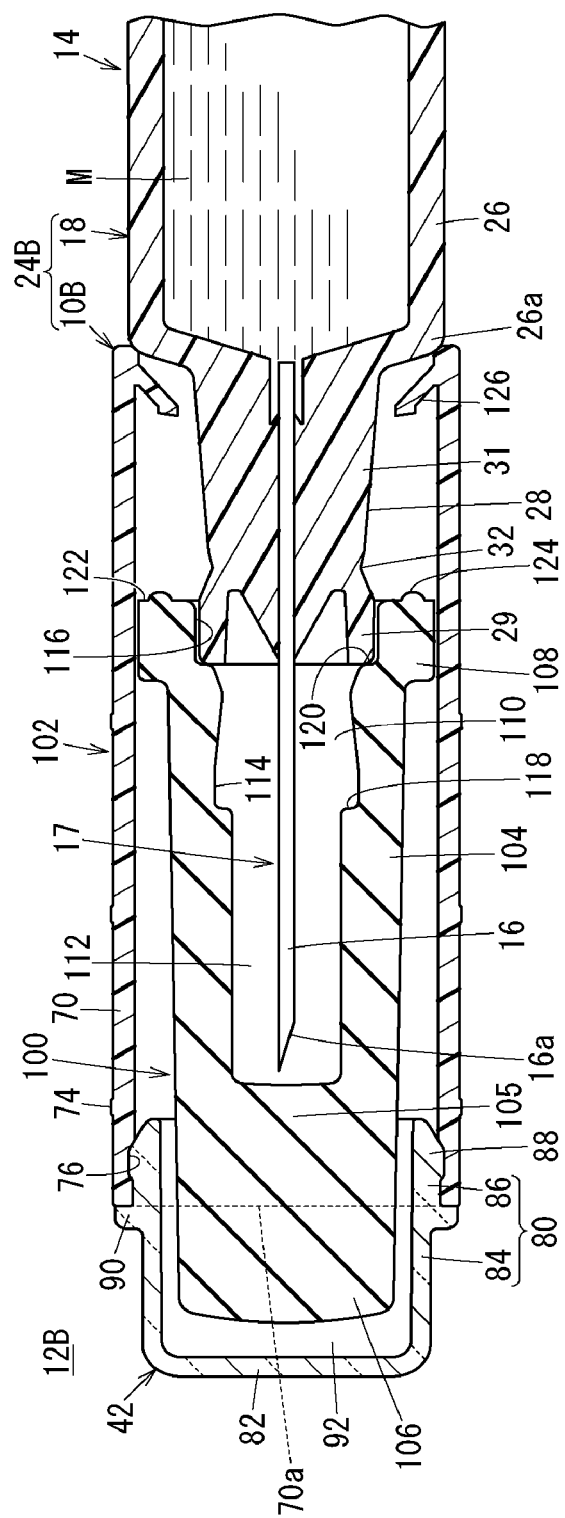
FIG. 13B is a second explanatory diagram of a state in which the cap body is disposed at a second position.

At this time, the cap body 100 is positioned at the second position, where the distal end extending portion 106 is received in the receiving space 92 formed by the annular peripheral wall portion 84 and the distal end wall 82, as illustrated in FIG. 13B. In addition, the proximal end portion of the cylindrical main body 70 of the cap cover 102 abuts against the shoulder portion 26a of the body portion 26 of the syringe body 14. As a result, the cap 10B is inhibited from being further displaced relative to the syringe body 14 in the proximal direction.

In this state, the distal end of the needle body 16 is positioned in the first hole portion 112 and the distal end head portion 29 of the needle hub 28 is inserted in a state of not being fitted in the third hole portion 116. In other words, the drug discharge port 16a is not sealed by the sealing portion 105. In addition, a predetermined gap is formed between the wall surface that constitutes the third hole portion 116 and the outer peripheral surface of the distal end head portion 29 of the needle hub 28. Further, a predetermined gap is formed between the distal end of the cap body 100 and the distal end wall 82 in a state in which the distal end surface of the distal end head portion 29 of the needle hub 28 is in contact with (abuts against) the second stepped surface 120.

According to the present embodiment, the cap body 100 is displaced from the first position to the second position and the outer peripheral portion of the distal end extending portion 106 as the viewing portion of the cap body 100 changes in appearance when the cap 10B removed from the syringe body 14 is to be remounted on the syringe body 14 (when the mounting tube portion 104 of the cap 10B removed from the syringe body 14 is close to the nozzle portion 17 of the syringe body 14 with the cap body 100 positioned at the first position). As a result, a user can easily and reliably discriminate between the unopened state and the opened state of the cap 10B with respect to the syringe body 14 having the needle body 16. Accordingly, the second embodiment can be similar in effect to the first embodiment.

According to the present embodiment, detachment of the cap body 100 in a proximal end direction with respect to the cap cover 102 can be inhibited by the engaging claw portion 126 being brought into contact with the proximal end surface 122 of the large-diameter proximal end portion 108 disposed in the proximal end portion of the cap body 100.

As illustrated in FIG. 13A, in the present embodiment, a distance L3 from the distal end of the cap body 100 to the distal end wall 82 of the distal end cover member 42 is longer than a distance L4 from the proximal end of the cap cover 102 to the distal end of the body portion 26 of the syringe body 14 in a state in which the proximal end surface 122 of the large-diameter proximal end portion 108 of the cap body 100 is engaged with the engaging claw portion 126 (engaging portion) of the cap cover 102 and the second stepped surface 120 (abutting portion) of the mounting tube portion 104 (mounting portion) of the cap body 100 abuts against the distal end surface (nozzle portion 17) of the needle hub 28. Accordingly, when the cap body 100 is displaced from the first position to the second position by the mounting tube portion 104 of the cap body 100 being pressed in the distal end direction by the needle hub 28 (nozzle portion 17) of the syringe body 14, the proximal end portion of the cap cover 102 abuts against the distal end portion (shoulder portion 26a) of the body portion 26 of the syringe body 14, and a predetermined gap is formed between the distal end of the cap body 100 and the distal end wall 82 as a result (see FIG. 13B). As a result, fitting of the mounting tube portion 104 of the cap body 100 onto the needle hub 28 is inhibited and remounting of the cap 10B onto the syringe body 14 is inhibited when the cap 10B removed from the syringe body 14 is to be remounted on the syringe body 14.

Third Embodiment

Next, a prefilled syringe 12C according to the third embodiment of the present invention will be described.

As illustrated in FIG. 14, the prefilled syringe 12C is provided with a syringe body 140 and a cap 10C detachable from the syringe body 140. The syringe body 140 has a syringe outer tube 142, the gasket 20, and the pusher 22. In the present embodiment, the syringe outer tube 142 and the cap 10C constitute a syringe assembly 24C, and the prefilled syringe 12C is assembled by the gasket 20 to which the pusher 22 is connected being inserted in a state in which the syringe outer tube 142 of the syringe assembly 24C is filled with the drug M.

The syringe outer tube 142 has the body portion 26, a hollow nozzle portion 144 protruding in the distal end direction from the distal end portion (shoulder portion 26a) of the cylindrical body portion 26 extending in the axial direction, and the flange portion 30 disposed in the proximal end portion of the body portion 26. The body portion 26, the nozzle portion 144, and the flange portion 30 are integrally formed. The constituent material of the syringe outer tube 142 can be similar to the constituent material of the syringe outer tube 18 of the first embodiment described above.

Figure 15:
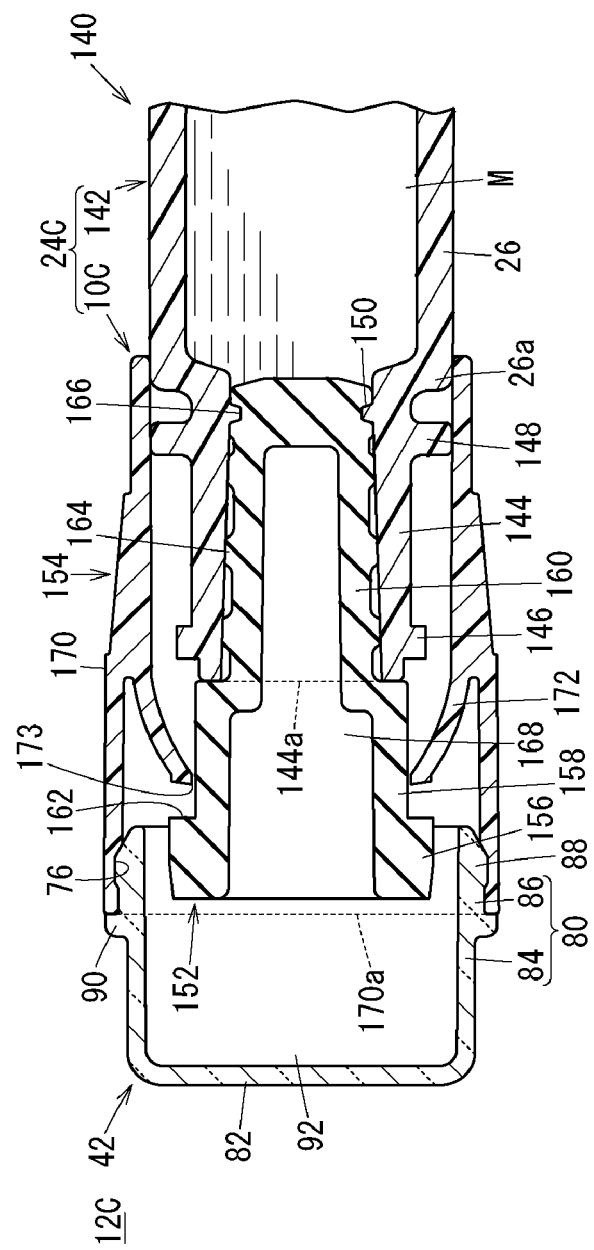
FIG. 15 is a partially-omitted and enlarged longitudinal cross-sectional view of the distal end side of the prefilled syringe illustrated in FIG. 14.
Figure 16:
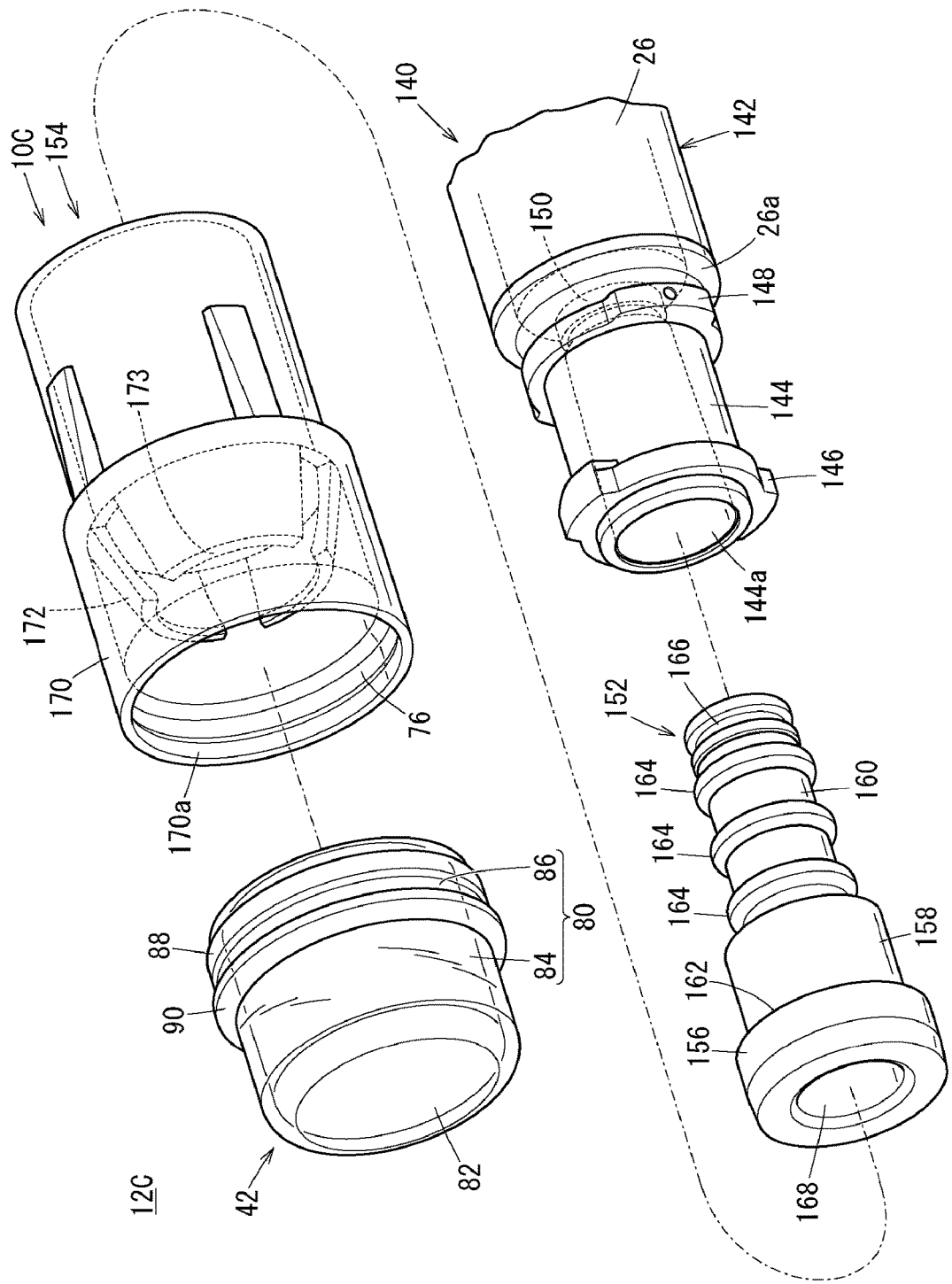
FIG. 16 is an exploded perspective view of FIG. 15.

As illustrated in FIGS. 15 and 16, the nozzle portion 144 is a female luer having a drug discharge port 144a disposed at the distal end of the nozzle portion 144. Disposed on the outer peripheral surface of the nozzle portion 144 are a distal end side protruding portion 146 for mounting of a male luer (not illustrated) and a proximal end side protruding portion 148 with which the inner peripheral surface of a cylindrical main body 170 comes into contact in the unopened state of the cap 10C. An annular projecting portion 150 (first locking portion) for locking a cap body 152 is disposed at the proximal end of the inner peripheral surface of the nozzle portion 144.

The cap 10C has the cap body 152, a cap cover 154, and the distal end cover member 42. The constituent material of the cap body 152 can be similar to the material of the cap body 38 described above.

The cap body 152 has a large-diameter distal end portion 156 (large-diameter portion) positioned in the distal end portion of the cap body 152, a small-diameter middle portion 158 disposed proximal of the large-diameter distal end portion 156, and a mounting portion 160 disposed proximal of the small-diameter middle portion 158.

The large-diameter distal end portion 156 functions as a viewing portion as described later. The outer diameter of the large-diameter distal end portion 156 is larger than the distal end outer diameter of the nozzle portion 144. The small-diameter middle portion 158 has an outer diameter smaller than the outer diameter of the large-diameter distal end portion 156 over the entire length of the small-diameter middle portion 158. A proximal stepped surface 162 facing the proximal direction is formed in the boundary portion between the large-diameter distal end portion 156 and the small-diameter middle portion 158.

The mounting portion 160 has an outer diameter smaller than the outer diameter of the small-diameter middle portion 158 and is inserted into the nozzle portion 144. The outer peripheral surface of the mounting portion 160 is provided with a plurality of (three in FIGS. 15 and 16) annular seal projections 164 (sealing portions) coming into liquid-tight contact with the inner peripheral surface of the nozzle portion 144 and an annular recess 166 (second locking portion) into which the annular projecting portion 150 is fitted. The plurality of seal projections 164 are separated at equal intervals in the axial direction of the cap body 152. The annular recess 166 is positioned in the proximal end portion of the mounting portion 160. The proximal end portion of the mounting portion 160 comes into liquid-tight contact with the inner peripheral surface of the nozzle portion 144.

In the cap body 152, the mounting portion 160 is inserted into the nozzle portion 144 and the proximal end portion of the mounting portion 160 comes into liquid-tight contact with the inner peripheral surface of the nozzle portion 144. The nozzle portion 144 is sealed as a result.

A recessed portion 168 (lightening space) open to the distal end surface of the cap body 152 is formed in the cap body 152. The recessed portion 168 extends to the position of the seal projection 164 that is positioned on the most proximal side in the mounting portion 160.

The cap cover 154 is configured to have a cylindrical shape. The cap cover 154 is made of a resin material having no transparency (substantially opaque resin material). The cap cover 154 has the cylindrical main body 170 longer than the entire length of the cap body 152. An opening 170a is formed at the distal end of the cylindrical main body 170 so that the cap body 152 is exposed (protrudes) from the cylindrical main body 170.

The outer diameter of the cylindrical main body 170 is formed such that a user is allowed to easily grasp the cylindrical main body 170 with his or her fingers. The annular locking groove 76 for locking the distal end cover member 42 is formed in the distal end portion of the inner peripheral surface of the cylindrical main body 170.

A plurality of (three in FIG. 16) engaging claw portions 172 (engaging portions) coming into contact with the proximal stepped surface 162 are disposed at equal intervals in the circumferential direction of the cylindrical main body 170 on the inner peripheral surface of the cylindrical main body 170. In other words, a predetermined gap is formed between the engaging claw portions 172 adjacent to each other in the circumferential direction. Each engaging claw portion 172 extends so as to be inclined in the distal end direction from the inner peripheral surface of the cylindrical main body 170 and is configured to be elastically deformable in the radial direction of the cylindrical main body 170. Each engaging claw portion 172 has a flat distal end surface. The hole diameter of a central hole 173 formed by the inner ends of the plurality of engaging claw portions 172 is smaller than the outer diameter of the large-diameter distal end portion 156. The inner diameter of the proximal end side of the cylindrical main body 170 is set to an inner diameter fitted to the outer diameter of the body portion 26 of the syringe outer tube 142.

A procedure for manufacturing the prefilled syringe 12C (cap 10C) according to the present embodiment is similar to the procedure for manufacturing the prefilled syringe 12A (cap 10A) according to the first embodiment.

In other words, the mounting portion 160 of the cap body 152 is fitted into the nozzle portion 144 and the large-diameter distal end portion 156 is inserted from the proximal end side of the cap cover 154 with the distal end cover member 42 mounted. Then, each engaging claw portion 172 is pressed by the large-diameter distal end portion 156. As a result, each engaging claw portion 172 is bent (elastically deformed) radially outward such that the inner diameter of the central hole 173 formed by the respective inner ends of the engaging claw portions 172 increases, and thus the large-diameter distal end portion 156 climbs over each engaging claw portion 172 and moves in the distal end direction beyond each engaging claw portion 172. Then, mounting of the cap cover 154 with respect to the cap body 152 is completed by the proximal end portion of the inner peripheral surface of the cylindrical main body 170 being brought into contact with the outer surface of the body portion 26. The syringe assembly 24C is manufactured as a result. The prefilled syringe 12C illustrated in FIG. 14 is manufactured by the syringe outer tube 142 of the syringe assembly 24C being filled with the drug M and the gasket 20 and the pusher 22 being mounted.

In the present embodiment, the mounting portion 160 is fitted into the nozzle portion 144 and the proximal end portion of the mounting portion 160 comes into liquid-tight contact with the inner peripheral surface of the nozzle portion 144 in the unopened state of the cap 10C. The nozzle portion 144 (drug discharge port 144a) is sealed as a result.

In addition, the cap body 152 is positioned at the first position, where the large-diameter distal end portion 156 is positioned proximal of the opening 170a of the cylindrical main body 170. Specifically, the distal end of the cap body 152 is positioned more proximally than the opening 170a of the cylindrical main body 170 and in the engagement extending portion 86 of the distal end cover member 42. As a result, the outer peripheral portion of the large-diameter distal end portion 156, which is a viewing portion, is hidden in the substantially opaque cylindrical main body 170 and cannot be viewed from the outside.

Ina state in which the cap body 152 is at the first position, a distance L5 from the proximal stepped surface 162 to the opening 170a of the cylindrical main body 170 is shorter than an axial length L6 of the small-diameter middle portion 158. In addition, each engaging claw portion 172 is separated more proximally than the proximal stepped surface 162 (see FIG. 15).

Next, operation for opening the cap 10C that is in the unopened state and a recap operation will be described. The recap operation is to reinstall the cap 10C on the syringe body 140 after removal of the cap 10C from the syringe body 140.

Figure 17A:
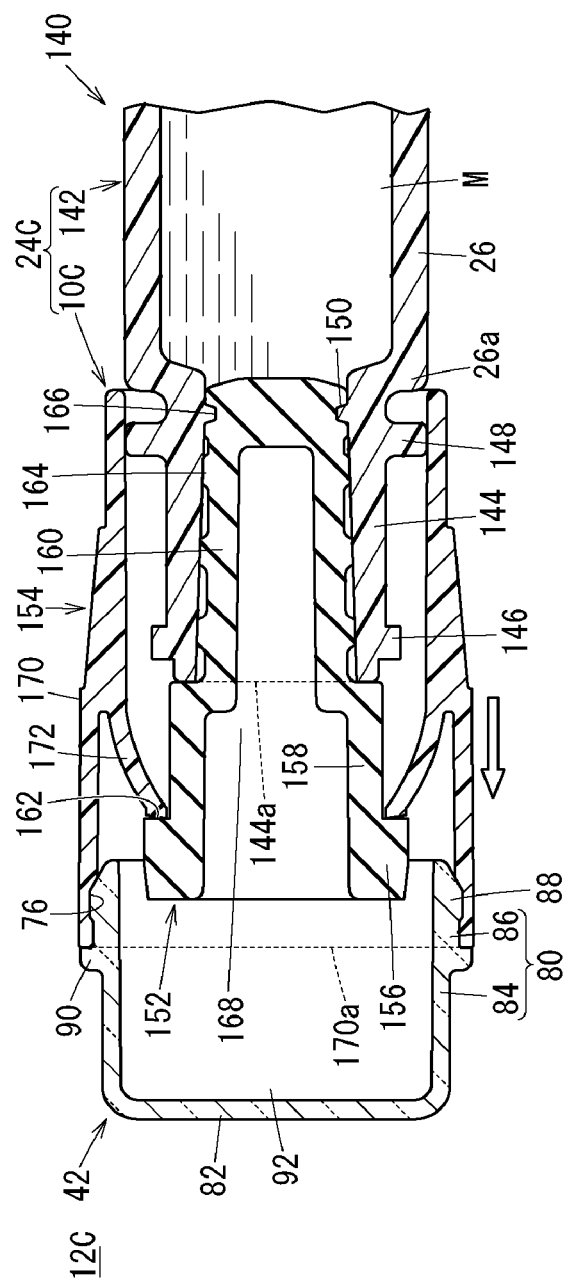
FIG. 17A is a first explanatory diagram of opening operation for the cap illustrated in FIG. 15.
Figure 17B:
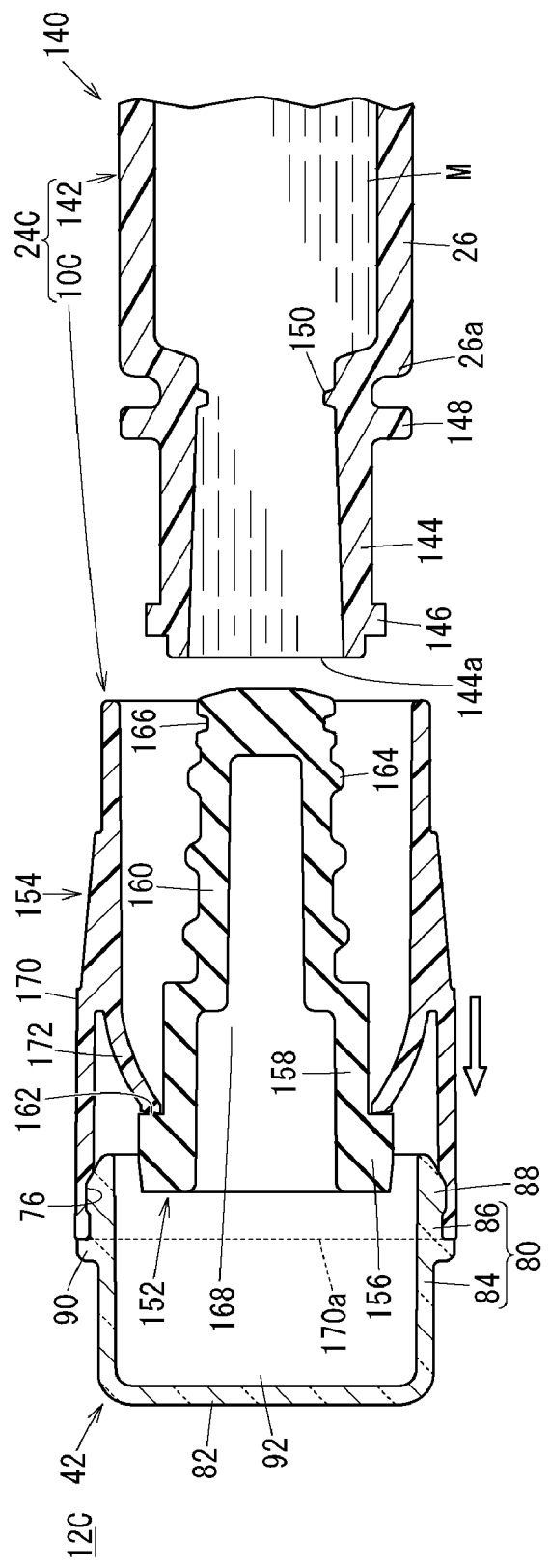
FIG. 17B is a second explanatory diagram of the opening operation for the cap.

A user who wishes to open the cap 10C displaces the cap cover 154 relative to the syringe body 140 in the distal end direction as illustrated in FIG. 17A. Then, the cap cover 154 is displaced in the distal end direction with respect to the cap body 152, and thus each engaging claw portion 172 comes into contact with the proximal stepped surface 162. Once the cap cover 154 is further displaced relative to the syringe body 140 in the distal end direction as illustrated in FIG. 17B, the proximal stepped surface 162 is pressed in the distal end direction by each engaging claw portion 172 and the mounting portion 160 of the cap body 152 comes out of the nozzle portion 144. The cap 10C is opened as a result.

In the open cap 10C, displacement of the cap body 152 in the distal direction with respect to the cylindrical main body 170 is restricted by the large-diameter distal end portion 156 coming into contact with the distal end wall 82 and proximal displacement of the cap body 152 with respect to the cylindrical main body 170 is restricted by engaging claw portion 172 coming into contact with the proximal stepped surface 162. In other words, the cap body 152 is not detached from the cap cover 154.

Figure 18A:
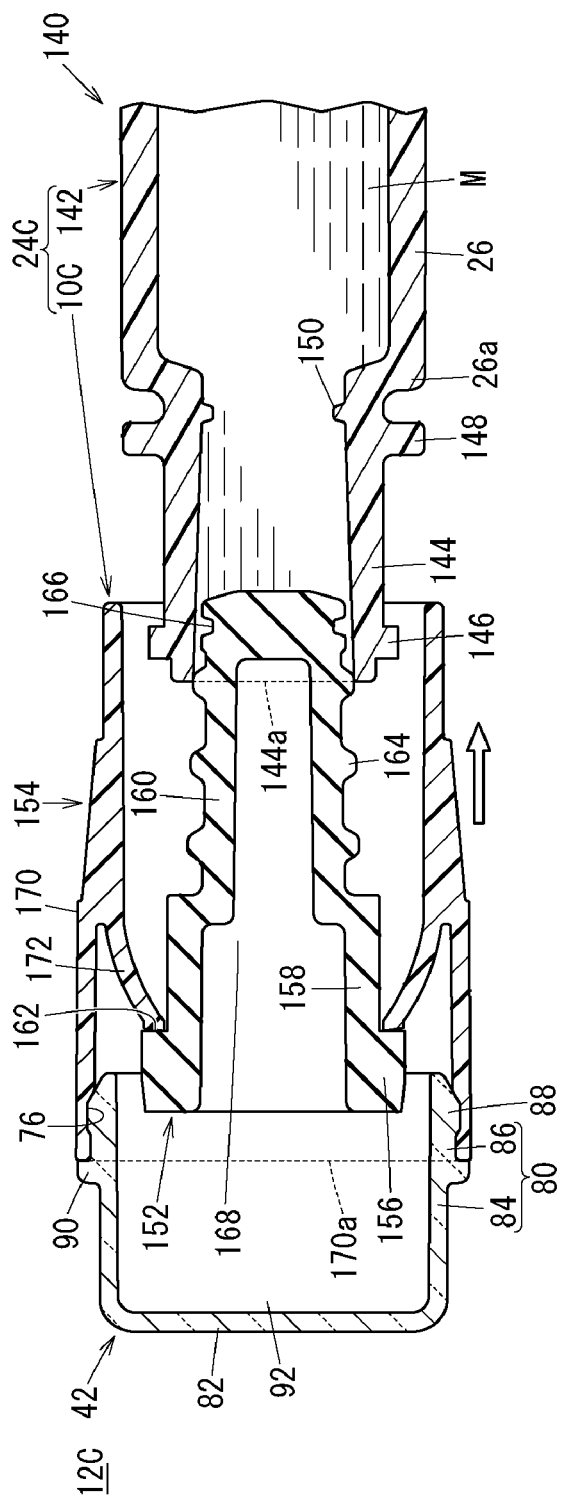
FIG. 18A is a first explanatory diagram of a recap operation for the cap illustrated in FIG. 15.

As illustrated in FIG. 18A, in a case where the syringe body 140 is recapped with the cap 10C after opening, the cap cover 154 is displaced relative to the syringe body 140 in the proximal direction. Then, the proximal end portion of the mounting portion 160 of the cap body 152 comes into contact with the nozzle portion 144 and proximal displacement of the cap body 152 is restricted. Once the cap cover 154 is further displaced relative to the syringe body 140 in the proximal direction, the cap cover 154 is displaced in the proximal direction with respect to the cap body 152, and thus the large-diameter distal end portion 156 protrudes in the distal end direction beyond the opening 170a of the cylindrical main body. As a result, the syringe body 140 is recapped with the cap 10C.

Figure 18B:
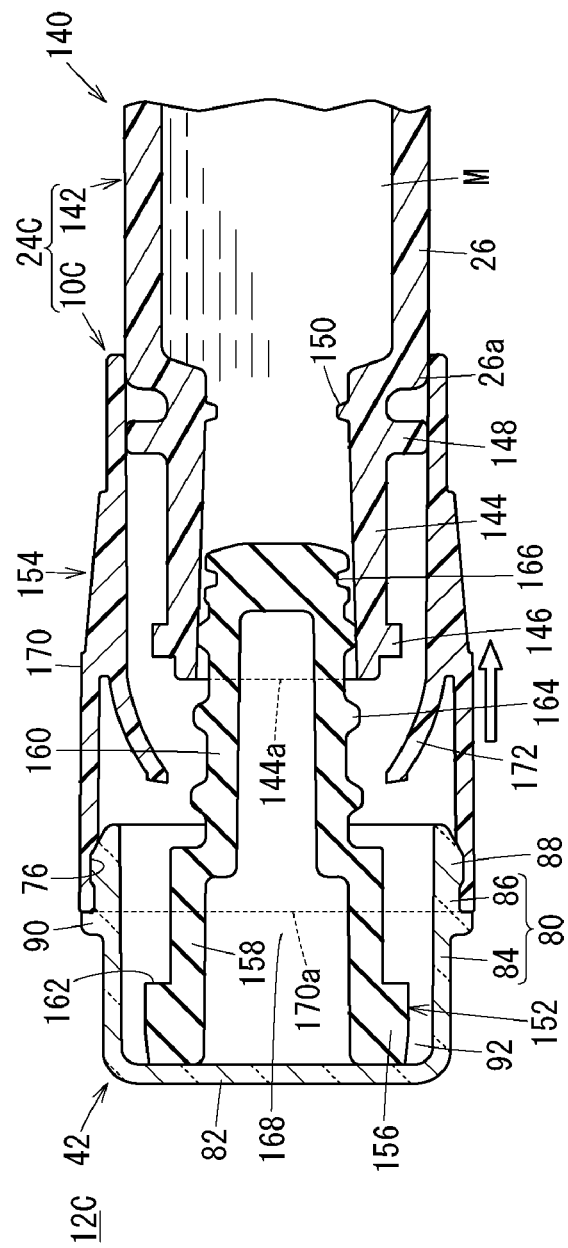
FIG. 18B is a second explanatory diagram of the recap operation for the cap.

At this time, the cap body 152 is positioned at the second position, where the large-diameter distal end portion 156 is received in the receiving space 92 formed by the annular peripheral wall portion 84 and the distal end wall 82, as illustrated in FIG. 18B. In addition, the drug discharge port 144a is sealed by the proximal end portion of the mounting portion 160 being fitted into the nozzle portion 144.

According to the present embodiment, the cap body 152 is displaced from the first position to the second position and at least the outer peripheral portion of the large-diameter distal end portion 156 as the viewing portion of the cap body 152 changes in appearance when the mounting portion 160 of the cap 10C removed from the syringe body 140 is close to the nozzle portion 144 of the syringe body 140 with the cap body 152 disposed at the first position. As a result, a user can easily and reliably discriminate between the unopened state and the recapped state, that is, the opened state of the cap 10C with respect to the syringe body 140 having the tubular nozzle portion 144. Accordingly, the third embodiment can be similar in effect to the first and second embodiments.

The cap body 152 can be locked in the nozzle portion 144 by the fitting force between the annular projecting portion 150 disposed on the inner peripheral surface of the nozzle portion 144 and the annular recess 166 disposed in the outer peripheral surface of the mounting portion 160.

Further, the tubular seal projection 164 coming into liquid-tight contact with the inner peripheral surface of the nozzle portion 144 is disposed on the outer peripheral surface of the mounting portion 160, and thus the space between the nozzle portion 144 and the mounting portion 160 can be effectively sealed in a liquid-tight manner.

Moreover, the recessed portion 168 open to the distal end surface of the cap body 152 is formed in the mounting portion 160, and thus the mounting portion 160 can be easily fitted into the nozzle portion 144 during manufacturing of the cap 10C.

The present embodiment is not limited to the above-described configuration. For example, an annular recess may be disposed in place of the annular projecting portion 150 in the inner peripheral surface of the nozzle portion 144 and an annular projecting portion may be disposed in place of the annular recess 166 in the mounting portion 160. Even in this case, the mounting portion 160 can be locked with respect to the nozzle portion 144. In addition, the mounting portion 160 may not be fitted in the nozzle portion 144 when the cap body 152 is at the second position. In this case, the outer diameter of the proximal end portion of the mounting portion 160 may be larger than, for example, the inner diameter of the drug discharge port 144a of the nozzle portion 144. As a result, the proximal end portion of the mounting portion 160 is not inserted into the drug discharge port 144a of the nozzle portion and remounting of the cap 10C onto the syringe body 14 is inhibited when the cap 10C is to be remounted on the syringe body 14 after removal from the syringe body 14.

Fourth Embodiment

Next, a prefilled syringe 12D according to a fourth embodiment of the present invention will be described. It should be noted that components of the prefilled syringe 12D according to the fourth embodiment that are identical to those of the prefilled syringe 12A according to the first embodiment are denoted by the same reference numerals and detailed descriptions of the components are omitted. In the present embodiment, configurations similar to those of the prefilled syringe 12A according to the first embodiment have similar actions and effects.

Figure 19:
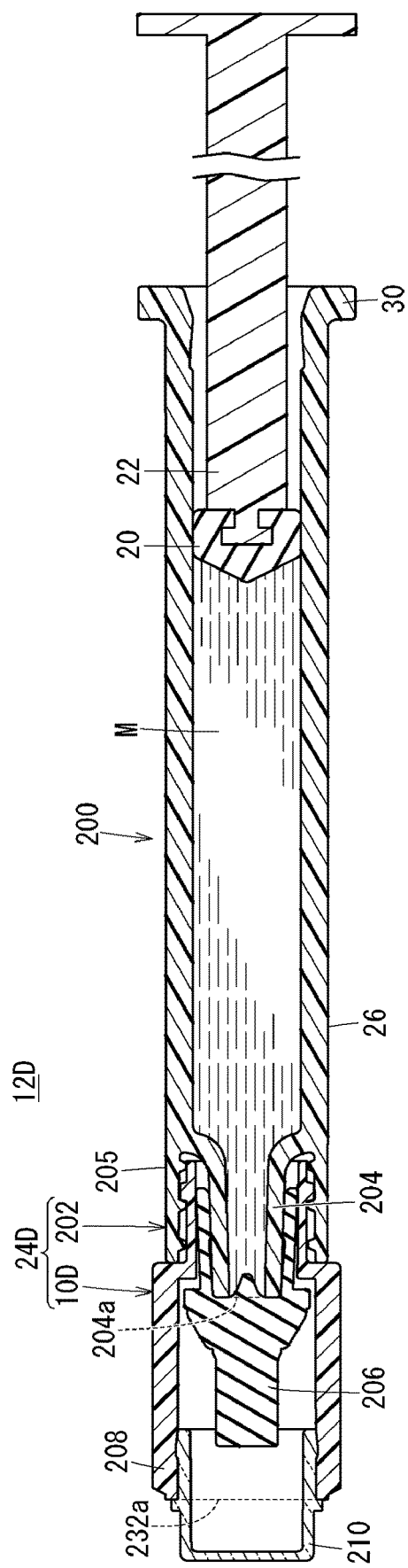
FIG. 19 is a longitudinal cross-sectional view of a prefilled syringe according to a fourth embodiment of the present invention.

As illustrated in FIG. 19, the prefilled syringe 12D is provided with a syringe body 200 and a cap 10D detachable from the syringe body 200. The syringe body 200 has a syringe outer tube 202, the gasket 20, and the pusher 22. In the present embodiment, the syringe outer tube 202 and the cap 10D constitute a syringe assembly 24D, and the prefilled syringe 12D is assembled by the gasket 20 to which the pusher 22 is connected being inserted in a state in which the syringe outer tube 202 of the syringe assembly 24D is filled with the drug M.

The syringe outer tube 202 has the cylindrical body portion 26 extending in the axial direction, a nozzle portion 204 protruding in the distal end direction from the distal end portion of the body portion 26, a syringe side connecting portion 205 disposed on the outer peripheral side of the nozzle portion 204, and the flange portion 30 disposed in the proximal end portion of the body portion 26. The body portion 26, the nozzle portion 204, the syringe side connecting portion 205, and the flange portion 30 are integrally formed.

Figure 20:
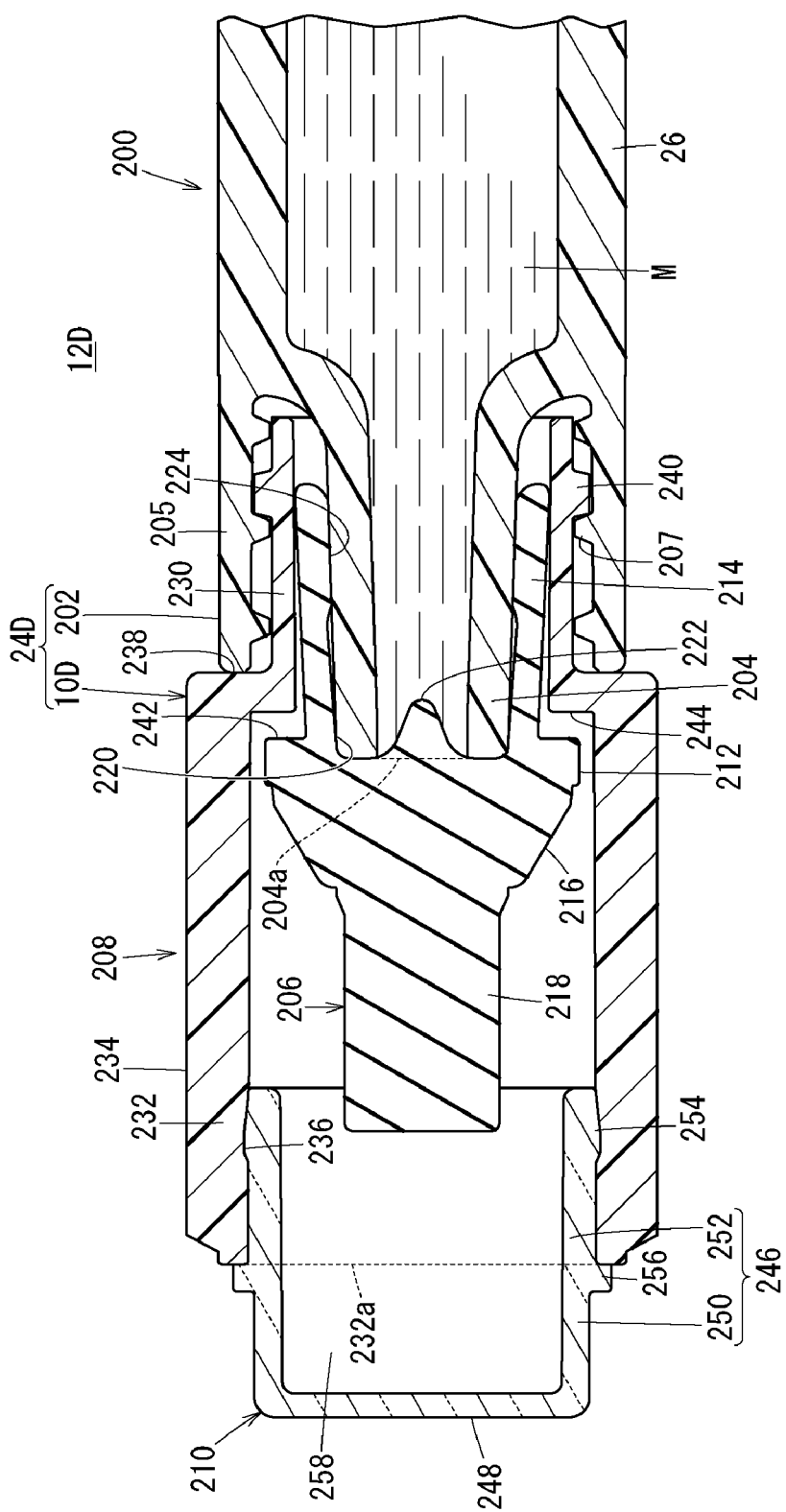
FIG. 20 is an enlarged longitudinal cross-sectional view of the distal end part of the prefilled syringe illustrated in FIG. 19.

As illustrated in FIG. 20, the nozzle portion 204 is a circular tube-shaped member forming a drug discharge port 204a communicating with the inner cavity of the body portion 26 and is configured as a luer connector. The syringe side connecting portion 205 is a lock adapter protruding distally from the distal end portion of the body portion 26 concentrically with the nozzle portion 204, and a female screw portion 207 is formed on the inner peripheral surface of the lock adapter. The cap 10D and a syringe needle (not illustrated) or the like are detachable from the syringe side connecting portion 205.

The constituent material of the syringe outer tube 202 can be similar to the constituent material of the syringe outer tube 18 of the first embodiment described above.

Figure 21:
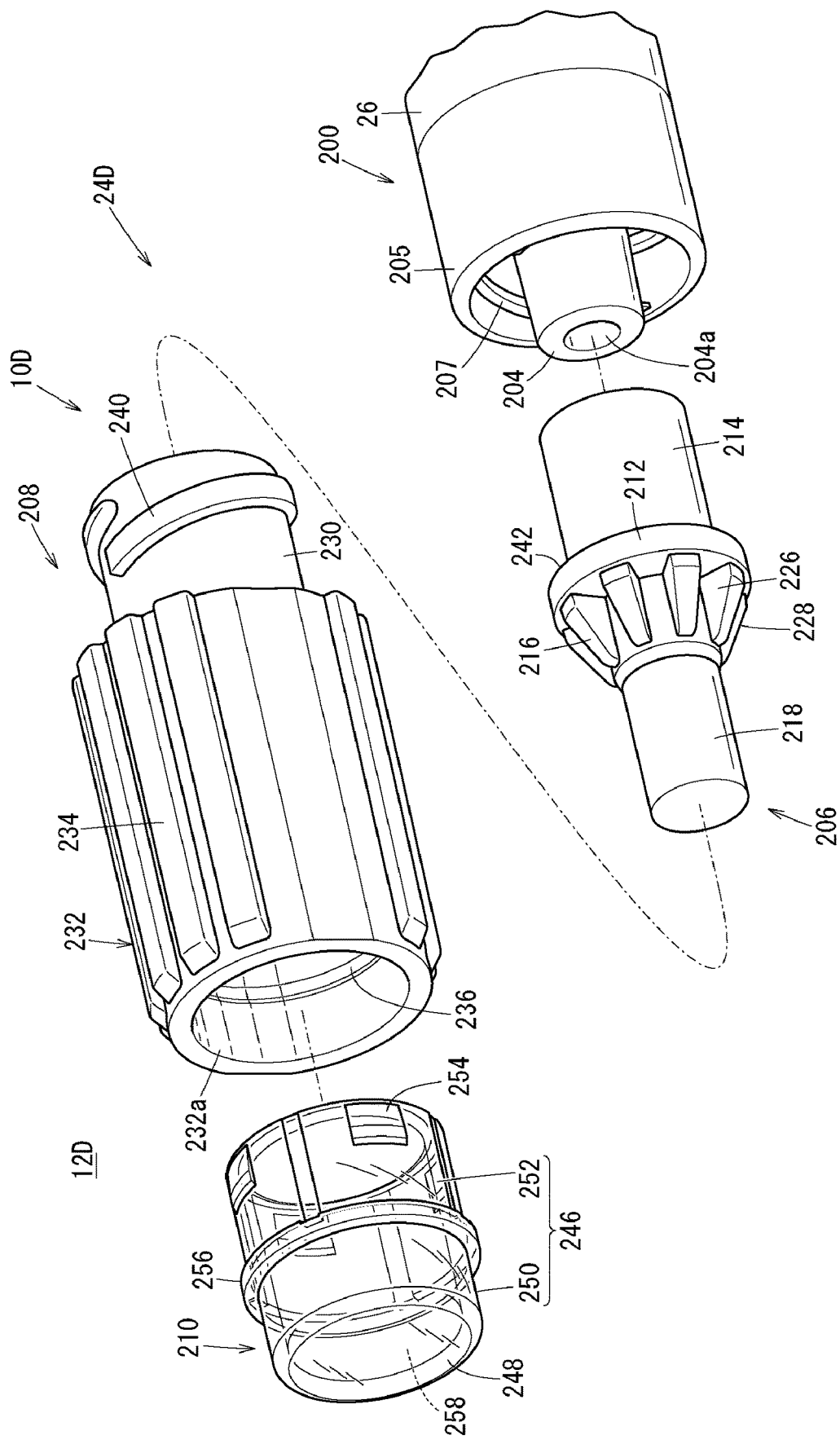
FIG. 21 is an exploded perspective view of FIG. 20.

As illustrated in FIGS. 20 and 21, the cap 10D is provided with a cap body 206 sealing the drug discharge port 204a in the unopened state, a cap cover 208 covering the cap body 206, and a distal end cover member 210 disposed distal of the cap cover 208.

The constituent material of the cap body 206 can be similar to the material of the cap body 38 described above.

The cap body 206 has a large-diameter portion 212, a mounting tube portion 214 (mounting portion) protruding from the surface of the large-diameter portion 212 that is on the proximal end side, a tapered portion 216 disposed on the surface of the large-diameter portion 212 that is on the distal end side, and a distal end protruding portion 218 protruding in the distal end direction from the tapered portion 216.

The large-diameter portion 212 is the part where the outer diameter of the cap body 206 is maximized. The large-diameter portion 212 extends radially outward beyond the mounting tube portion 214. The mounting tube portion 214 is a circular tube-shaped member that is fitted over (fitted onto) the outer peripheral portion of the nozzle portion 204 in the unopened state of the cap 10D. The mounting tube portion 214 has a length of protrusion shorter than the axial length of the nozzle portion 204.

The mounting tube portion 214 has a sealing portion 220 positioned in the distal end portion of the mounting tube portion 214 and configured to seal the drug discharge port 204a in a liquid-tight manner and a raised portion 222 raised from the sealing portion 220. The sealing portion 220 abuts against the distal end portion of the nozzle portion 204. Specifically, the sealing portion 220 abuts against the distal end surface of the nozzle portion 204 or the side peripheral surface of the distal end portion of the nozzle portion 204. The drug discharge port 204a is sealed as a result. It should be noted that the drug discharge port 204a is sealed in a liquid-tight manner so that the drug M does not leak to the outside of the cap body 206. Accordingly, even in a case where the sealing portion 220 abuts against only the side peripheral surface of the distal end portion of the nozzle portion 204, the sealing portion 220 seals the drug discharge port 204a in a liquid-tight manner. The inner cavity of the mounting tube portion 214 extends to the proximal end portion of the large-diameter portion 212. An annular abutting projecting portion 224 (abutting portion) configured to abut against the distal end portion of the nozzle portion 204 is disposed in the proximal end portion of the inner peripheral surface of the mounting tube portion 214. In the installation state (unopened state) where the cap body 206 is mounted on the nozzle portion 204, the abutting projecting portion 224 is sandwiched between the nozzle portion 204 and a cylindrical connecting portion 230 and undergoes compressive deformation. The cylindrical connecting portion 230, which will be described later, constitutes the cap cover 208.

The outer peripheral surface of the tapered portion 216 is reduced in diameter in a tapered shape from the large-diameter portion 212 toward the distal end protruding portion 218. A plurality of recessed portions 226 extending along the axial direction of the cap body 206 are formed at equal intervals in the circumferential direction on the outer peripheral surface of the tapered portion 216 (see FIG. 21). In other words, a plurality of ribs 228 extending along the axial direction of the cap body 206 are formed at equal intervals in the circumferential direction in the tapered portion 216.

The distal end protruding portion 218 is configured to have a columnar shape and has an outer diameter smaller than the outer diameter of the mounting tube portion 214. The distal end protruding portion 218 may be colored in red or any other color that a user can recognize with relative ease. As for coloring of the distal end protruding portion 218, the outer surface of the distal end protruding portion 218 may be painted or pre-colored rubber or a pre-colored synthetic resin may constitute the cap body 206. The distal end protruding portion 218 functions as a viewing portion as described later.

The cap cover 208 is configured to have a cylindrical shape and is made of a resin material having no transparency (substantially opaque resin material). Alternatively, the cap cover 208 may be made of a transparent material. The cap cover 208 has the cylindrical connecting portion 230 positioned in the proximal end portion of the cap cover 208 and detachable from the syringe side connecting portion 205 by screwing, a cylindrical main body 232 extending in the distal end direction from the distal end of the cylindrical connecting portion 230, and an opening 232a disposed at the distal end of the cylindrical main body 232 so that the cap body 206 is exposed from the cap cover 208.

The axial length of the cylindrical main body 232 is longer than the length dimension from the surface of the large-diameter portion 212 that is on the proximal end side to the protruding end surface (distal end surface) of the distal end protruding portion 218 and is shorter than the entire length of the cap body 206. In other words, the axial length of the cylindrical main body 232 is set to a length at which the cap body 206 does not protrude (is not exposed) from the opening 232a of the cap cover 208 in a state in which the mounting tube portion 214 is mounted on the nozzle portion 204 (unopened state) and the distal end protruding portion 218 of the cap body 206 protrudes (is exposed) from the opening 232a of the cap cover 208 in a state in which the mounting tube portion 214 is mounted on the nozzle portion 204. The inner diameter of the cylindrical main body 232 is slightly larger than the outer diameter of the large-diameter portion 212.

The outer diameter of the cylindrical main body 232 is formed such that a user is allowed to easily grasp the cylindrical main body 232 with his or her fingers. A non-slip portion 234 functioning as a non-slip portion for a user's fingers is formed on the outer peripheral surface of the cylindrical main body 232. The non-slip portion 234 is configured by a plurality of projecting portions extending along the axial direction of the cylindrical main body 232 being disposed in the circumferential direction of the cylindrical main body 232. An annular locking groove 236 for locking the distal end cover member 210 is formed in the distal end portion of the inner peripheral surface of the cylindrical main body 232. An insertion restricting portion 238 configured to abut against the distal end of the syringe side connecting portion 205 is disposed at the proximal end of the cylindrical main body 232.

The cylindrical connecting portion 230 is a cylinder member disposed concentrically with the cap cover 208, and a male screw portion 240 configured to be screwed into the female screw portion 207 is formed on the outer peripheral surface of the cylindrical connecting portion 230. The inner diameter of the cylindrical connecting portion 230 is smaller than the inner diameter of the cap cover 208 and the outer diameter of the large-diameter portion 212. In other words, an engaging stepped surface 244 configured to come into contact with a proximal stepped surface 242, which is outside the mounting tube portion 214 and constitutes the surface of the large-diameter portion 212 that is on the proximal end side, is formed at the boundary between the cap cover 208 and the cylindrical connecting portion 230 (see FIG. 20).

The distal end cover member 210 is formed in a substantially U-shape in longitudinal cross portion. The distal end cover member 210 covers the cap body 206 together with the cap cover 208 such that a user operating the cap 10D cannot touch the cap body 206. In other words, the distal end cover member 210 has a contact blocking function. In addition, the distal end cover member 210 functions as a detachment blocking portion blocking the cap body 206 from being detached from the opening 232a of the cap cover 208. The distal end cover member 210 has an annular portion 246 and a distal end wall 248 disposed in the distal end portion of the annular portion 246. The annular portion 246 has a proximal end portion fitted in the distal end portion of the cap cover 208 so as to protrude distally from the opening 232a of the cap cover 208.

The annular portion 246 includes an annular peripheral wall portion 250 on the distal end side and a tubular engagement extending portion 252 extending in the proximal direction from the annular peripheral wall portion 250. The inner diameter of the annular portion 246 is constant from the distal end of the annular portion 246 to the proximal end of the annular portion 246 and is larger than the outer diameter of the distal end protruding portion 218. A plurality of locking claws 254 configured to be mounted on the locking groove 236 of the cap cover 208 are disposed at equal intervals in the circumferential direction on the outer peripheral surface of the engagement extending portion 252. A positioning projection 256 coming into contact with the distal end surface of the cap cover 208 is disposed on the outer peripheral surface of the proximal end portion of the annular peripheral wall portion 250.

The distal end cover member 210 is integrally molded with a transparent resin material. In a case where a transparent resin material constitutes the cap cover 208, the transparency of the distal end cover member 210 is set higher than the transparency of the cap cover 208. As a result, a user can view the inside of the distal end cover member 210 more clearly than the inside of the cap cover 208 from the outside of the cap 10D. The distal end cover member 210 may be colored although the distal end cover member 210 is colorless in the present embodiment.

Basically, the prefilled syringe 12D according to the present embodiment is configured as described above. Next, a procedure for attaching the cap 10D with respect to the syringe outer tube 202 during manufacturing of the prefilled syringe 12D will be described.

Figure 22A:
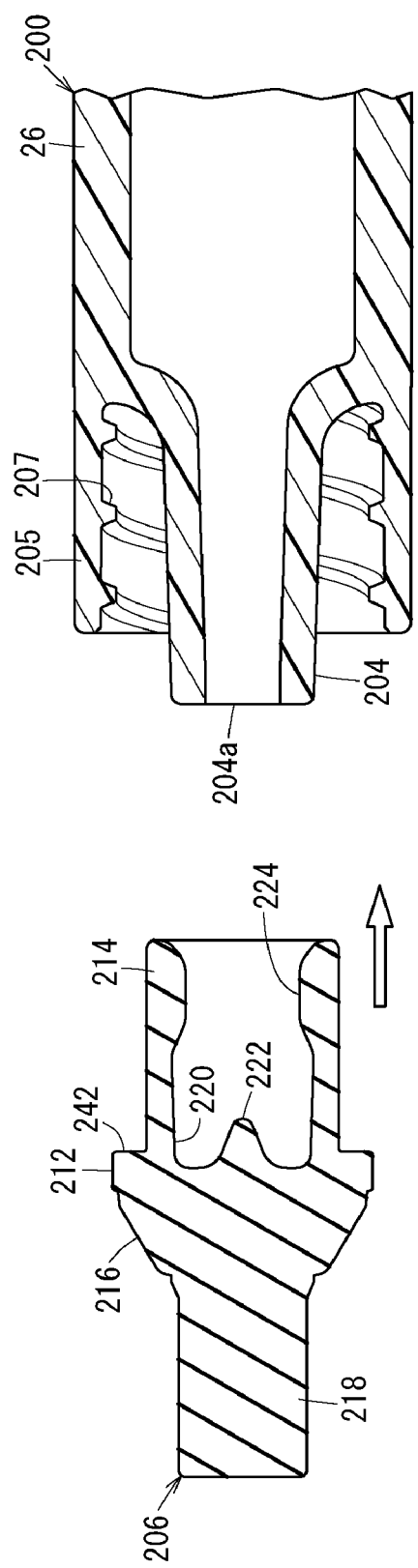
FIG. 22A is a first explanatory cross-sectional view of an assembly method for the cap illustrated in FIG. 20.

First, the mounting tube portion 214 of the cap body 206 is fitted over the nozzle portion 204 of the syringe outer tube 202 as illustrated in FIG. 22A. At this time, the distal end portion of the nozzle portion 204 is allowed to abut against the sealing portion 220 of the cap body 206.

Subsequently, the distal end cover member 210 is mounted with respect to the cap cover 208 by the locking claw 254 of the distal end cover member 210 being fitted into the locking groove 236 of the cap cover 208. It should be noted that the mounting of the distal end cover member 210 onto the cap cover 208 may be performed after the cylindrical connecting portion 230 is completely mounted on the syringe side connecting portion 205.

Figure 22B:
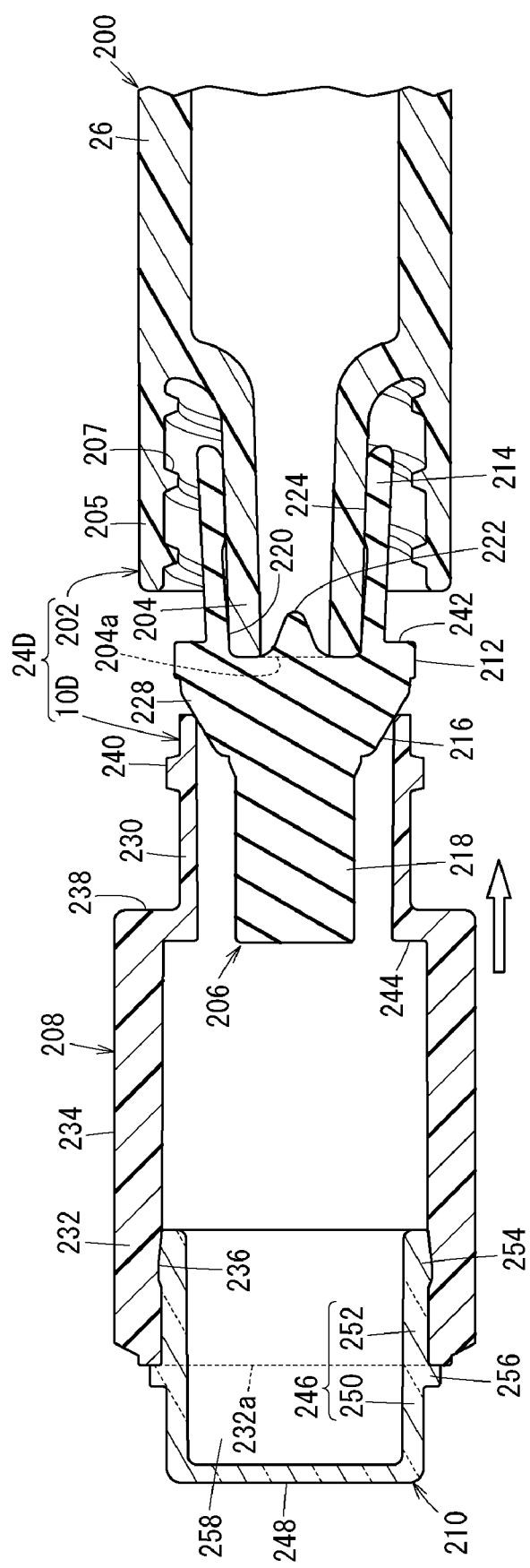
FIG. 22B is a second explanatory cross-sectional view of the assembly method for the cap.
Figure 25:
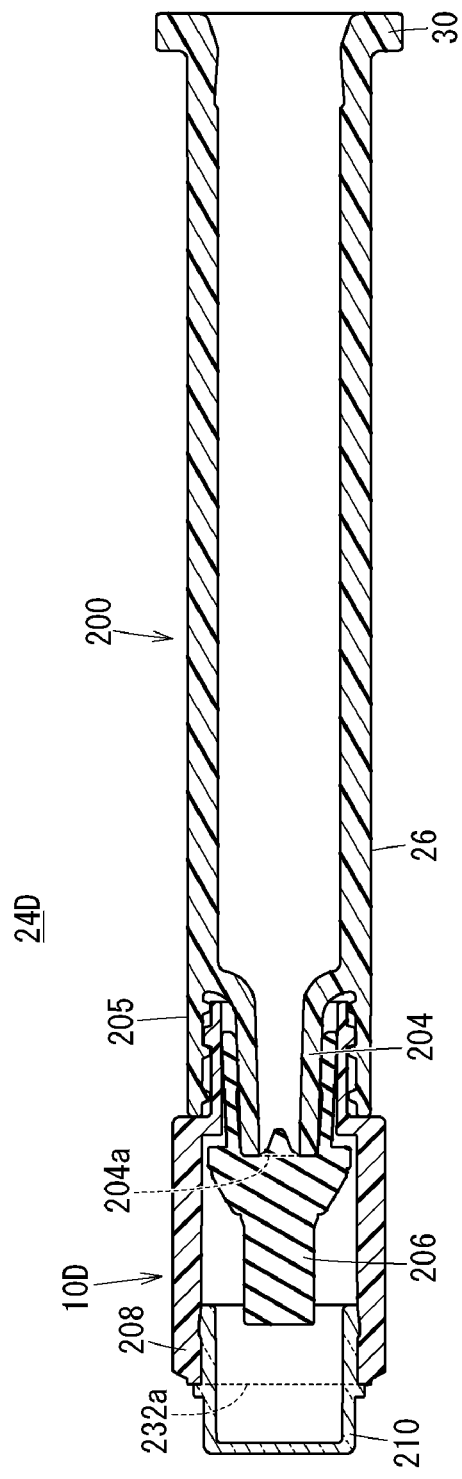
FIG. 25 is a longitudinal cross-sectional view of a syringe assembly according to the fourth embodiment.

Subsequently, the distal end protruding portion 218 is inserted from the proximal end side of the cylindrical connecting portion 230 and the proximal end portion of the cylindrical connecting portion 230 is brought into contact with the outer surface of the tapered portion 216 (outer surface of the rib 228) (see FIG. 22B). Then, the cylindrical connecting portion 230 and the syringe outer tube 202 are brought close to each other. As a result, the tapered portion 216 and the large-diameter portion 212 are passed through the inner cavity of the cylindrical connecting portion 230 while being elastically deformed. Subsequently, the cap 10D is mounted with respect to the syringe outer tube 202 by the male screw portion 240 of the cylindrical connecting portion 230 being screwed into the female screw portion 207 of the syringe side connecting portion 205. Configured as a result is the syringe assembly 24D provided with the syringe outer tube 202 and the cap 10D (see FIG. 25). It should be noted that the large-diameter portion 212 is positioned in the cap cover 208 in a state in which the cap 10D is completely mounted on the syringe outer tube 202 (see FIG. 20).

In addition, the cap body 206 is positioned at the first position, where the distal end protruding portion 218 is proximal of the opening 232a of the cap cover 208. At this time, the distal end protruding portion 218 is positioned in the cylindrical main body 232. Accordingly, the outer peripheral portion of the distal end protruding portion 218, which is a viewing portion, is hidden in the opaque cap cover 208 and cannot be viewed from the outside.

The prefilled syringe 12D is configured by the syringe outer tube 202 of the syringe assembly 24D configured as described above being filled with the drug M and the gasket 20 and the pusher 22 being mounted.

Next, operation for opening the cap 10D that is in the unopened state and a recap operation will be described. The recap operation is to reinstall the cap 10D on the syringe outer tube 202 after opening of the cap 10D.

Figure 23:
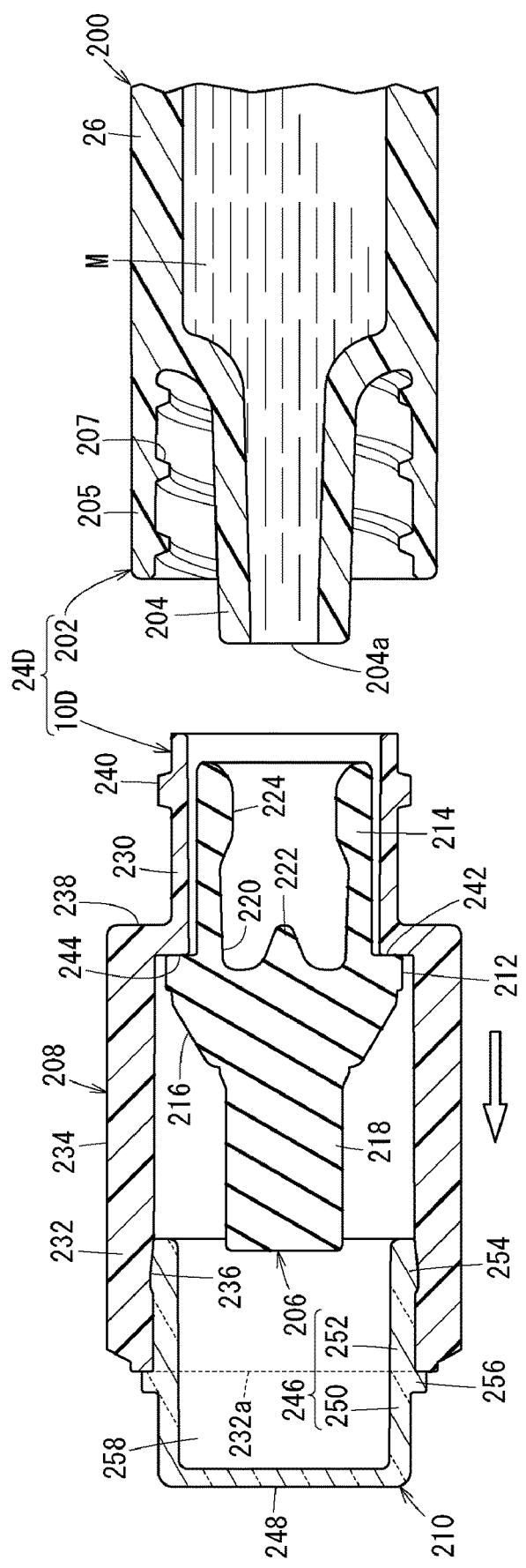
FIG. 23 is an explanatory cross-sectional view of opening operation for the cap illustrated in FIG. 20.

A user who wishes to open the cap 10D grasps the cap cover 208 with his or her fingers and rotates the cap 10D in the direction in which the screwing (tightening) of the male screw portion 240 of the cylindrical connecting portion 230 with respect to the female screw portion 207 of the syringe side connecting portion 205 loosens. Then, with the screwing between the male screw portion 240 and the female screw portion 207 released, the cap cover 208 is pulled out from the syringe outer tube 202. Then, the engaging stepped surface 244 of the cylindrical connecting portion 230 comes into contact with the proximal stepped surface 242 of the large-diameter portion 212, the cap body 206 is pressed in the distal end direction by the cylindrical connecting portion 230, and the mounting tube portion 214 is detached from the nozzle portion 204 as illustrated in FIG. 23. The cap 10D is opened as a result.

In a case where the syringe outer tube 202 is recapped with the cap 10D after opening, the distal end portion of the nozzle portion 204 of the syringe outer tube 202 is inserted into the cylindrical connecting portion 230 from the opening of the cylindrical connecting portion 230 that is on the proximal end side. Then, the distal end portion of the nozzle portion 204 comes into contact with the abutting projecting portion 224 of the cap body 206 as illustrated in FIG. 24A.

Figure 24B:
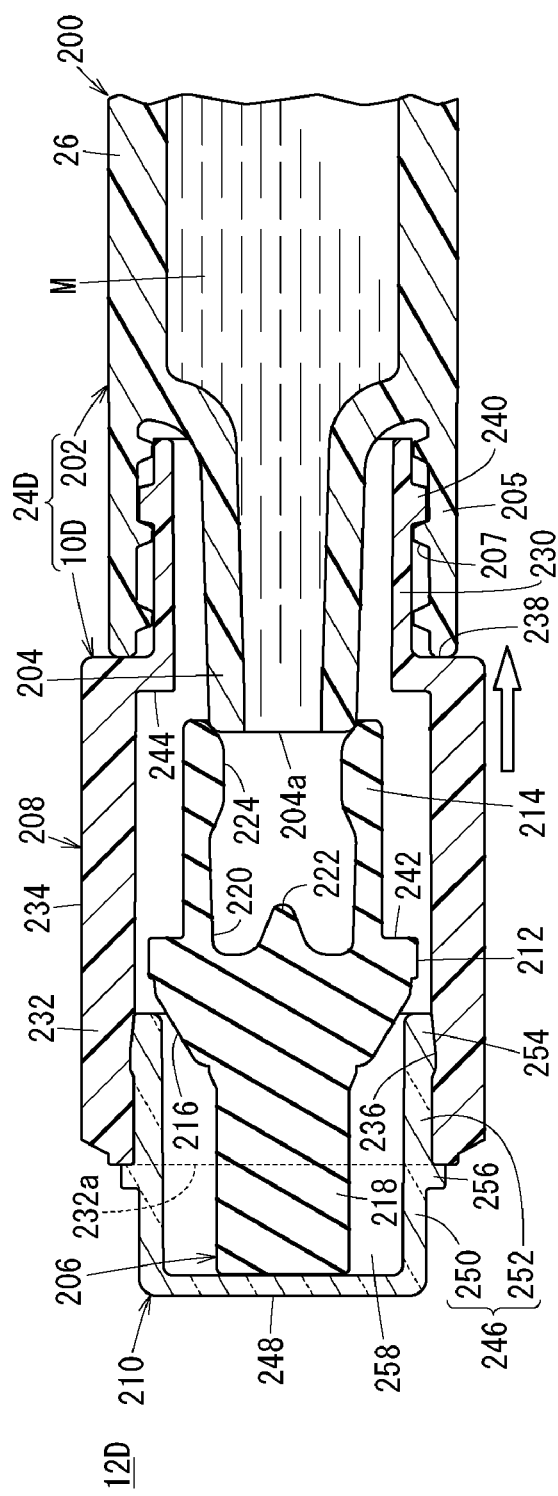
FIG. 24B is a longitudinal cross-sectional view illustrating a recapped state in which the recap operation is completed.

Once the cap cover 208 and the syringe outer tube 202 are subsequently brought close to each other, abutting between the abutting projecting portion 224 of the cap body 206 and the distal end portion of the nozzle portion 204 causes the cap body 206 at the first position to be pressed by the nozzle portion 204 and displaced in the distal end direction with respect to the cap cover 208. Then, the distal end protruding portion 218 protrudes distally from the opening 232a on the distal end side of the cap cover 208. Subsequently, the syringe outer tube 202 is recapped (remounted) with the cap 10D after opening by the male screw portion 240 of the cylindrical connecting portion 230 being screwed into the female screw portion 207 of the syringe side connecting portion 205 as illustrated in FIG. 24B. At this time, the cap body 206 is positioned at the second position, where the distal end protruding portion 218 is received in a receiving space 258 formed by the annular peripheral wall portion 250 and the distal end wall 248. Accordingly, the outer peripheral portion of the distal end protruding portion 218, which is a viewing portion, can be viewed from the outside via the transparent distal end cover member 210. The protruding end surface (distal end surface) of the distal end protruding portion 218 of the cap body 206 comes into contact with the distal end wall 248, and the mounting tube portion 214 is not fitted in the outer peripheral portion of the nozzle portion 204.

According to the present embodiment, the cap body 206 is displaced from the first position to the second position and the outer peripheral portion of the distal end protruding portion 218 as the viewing portion of the cap body 206 changes in appearance when the male screw portion 240 of the cap 10D removed from the syringe outer tube 202 is screwed into the female screw portion 207 of the syringe side connecting portion 205. Specifically, the outer peripheral portion of the distal end protruding portion 218, which could not be viewed, becomes visible by the cap body 206 being displaced. As a result, a user can easily and reliably discriminate between the unopened state of the cap 10D and the recapped state in which the cap 10D is remounted on the syringe outer tube 202 after removal from the syringe outer tube 202 by the screwing between the male screw portion 240 of the cap cover 208 and the female screw portion 207 of the syringe side connecting portion 205, which is a lock adapter.

The cap cover 208 is substantially opaque and the distal end cover member 210 is transparent. Accordingly, the distal end protruding portion 218 of the cap body 206 is invisible at the first position and visible at the second position. Accordingly, a change in the appearance of the distal end protruding portion 218, which is a viewing portion, becomes clear and it is possible to discriminate between the unopened state and the recapped state of the cap 10D with greater ease.

Further, when the cap body 206 is at the second position, the cap cover 208 and the distal end cover member 210 cover the cap body 206 such that a user operating the cap 10D cannot touch the cap body 206. Accordingly, it is possible to inhibit a user from accidentally returning the cap body 206 at the second position to the first position in the recapped state.

Moreover, the distal end of the distal end cover member 210 is closed by the distal end wall 248, and thus it is possible to more reliably inhibit a user from accidentally returning the cap body 206 at the second position to the first position in the recapped state.

In the present embodiment, the distal end cover member 210 is mounted on the cap cover 208 by engagement of the engagement extending portion 252 with the inner peripheral surface of the cap cover 208. Specifically, the locking claw 254 of the distal end cover member 210 is fitted into the locking groove 236 of the cap cover 208, and thus it is possible to inhibit a user from accidentally removing the distal end cover member 210.

Movement of the distal end cover member 210 in a proximal direction with respect to the cap cover 208 is inhibited by the positioning projection 256 of the distal end cover member 210 abutting against the distal end of the cap cover 208. As a result, the distal end cover member 210 is not moved in the proximal direction with respect to the cap cover 208 and it is possible to reliably form the receiving space 258, which receives the distal end protruding portion 218 as a viewing portion protruding from the opening 232a of the cap cover 208.

Further, the distal end protruding portion 218 is disposed at the distal end of the cap body 206, and thus a user can discriminate between the unopened state and the recapped state of the cap 10D on the basis of whether or not the cap body 206 protrudes from the opening 232a of the cap cover 208.

In the present embodiment, the abutting projecting portion 224 protrudes inward to the proximal end portion of the inner peripheral surface of the mounting tube portion 214. As a result, the abutting projecting portion 224, which is an abutting portion, reliably abuts against the distal end portion of the nozzle portion 204, and thus the cap body 206 can be reliably displaced from the first position to the second position.

The abutting projecting portion 224 is annularly disposed on the inner peripheral surface of the proximal end portion of the mounting tube portion 214, and thus the abutting projecting portion 224 is capable of abutting against the distal end portion of the nozzle portion 204 in a more reliable manner.

Further, the abutting projecting portion 224 is sandwiched between the nozzle portion 204 and the cylindrical connecting portion 230 and compressed in a state in which the cap 10D is mounted on the syringe outer tube 202 and the cap body 206 is positioned at the first position. As a result, the cap body 206 is unlikely to be disengaged from the nozzle portion 204, and thus a state in which the drug discharge port 204a is sealed by the sealing portion 220 can be reliably maintained.

In the present embodiment, the cylindrical main body 232 has the engaging stepped surface 244 functioning as an engaging portion at the boundary with the cylindrical connecting portion 230, the large-diameter portion 212 has the proximal stepped surface 242 at the boundary with the mounting tube portion 214, and the engaging stepped surface 244 is engaged with the proximal stepped surface 242. As a result, detachment of the cap body 206 in a proximal end direction with respect to the cap cover 208 can be reliably inhibited.

The cap body 206 has the tapered portion 216 extending in the distal end direction from the distal end of the large-diameter portion 212 and decreasing in outer diameter toward the distal end. As a result, the cap body 206 is easily inserted from the proximal direction of the cap cover 208 during assembly of the cap 10D.

Further, the cap cover 208 has the insertion restricting portion 238 configured to abut against the distal end of the syringe side connecting portion 205 at the proximal end of the cylindrical main body 232. The length of insertion of the cylindrical connecting portion 230 into the space between the syringe side connecting portion 205 and the nozzle portion 204 is restricted by the insertion restricting portion 238 abutting against the syringe side connecting portion 205. As a result, the cylindrical connecting portion 230 is inhibited from being excessively inserted. As a result, it is possible to inhibit the distal end protruding portion 218 from protruding from the opening 232a by the cap body 206 being displaced relative to the cap cover 208 with the nozzle portion 204 sealed.

In the present embodiment, the inner diameter of the annular portion 246 is constant from the distal end of the annular portion 246 to the proximal end of the annular portion 246 and is larger than the outer diameter of the distal end protruding portion 218 (distal end portion) of the cap body 206. When the cap body 206 is at the first position, at least the distal end of the cap body 206 is positioned in the annular portion 246. Accordingly, it is possible to inhibit the cap body 206 from being caught on the inner peripheral surface of the distal end cover member 210 and it is possible to inhibit non-displacement of the cap body 206 to the second position during displacement of the cap body 206 from the first position to the second position.

The present embodiment is not limited to the above-described configuration. For example, procedures for attaching the cap 10D with respect to the syringe outer tube 202 are not limited to the above-described procedure and the following attachment procedure may be adopted as an example. First, only the cap cover 208 is mounted with respect to the syringe outer tube 202 by the male screw portion 240 of the cylindrical connecting portion 230 being screwed into the female screw portion 207 of the syringe side connecting portion 205. Subsequently, the cap body 206 is inserted into the cap cover 208 from the opening 232a of the cap cover 208 and the mounting tube portion 214 of the cap body 206 is fitted over the nozzle portion 204 of the syringe outer tube 202. Subsequently, the distal end cover member 210 is mounted with respect to the cap cover 208 by the locking claw 254 of the distal end cover member 210 being fitted into the locking groove 236 of the cap cover 208. As a result, the cap 10D is mounted with respect to the syringe outer tube 202 and the syringe assembly 24D provided with the syringe outer tube 202 and the cap 10D is configured (see FIG. 25).

Fifth Embodiment

Next, a prefilled syringe 12E according to a fifth embodiment of the present invention will be described. It should be noted that components of the prefilled syringe 12E according to the fifth embodiment that are identical to those of the prefilled syringe 12D according to the fourth embodiment are denoted by the same reference numerals and detailed descriptions of the components are omitted. In the present embodiment, configurations similar to those of the prefilled syringe 12D according to the fourth embodiment have similar actions and effects. This also applies to sixth to eleventh embodiments to be described later.

Figure 26:
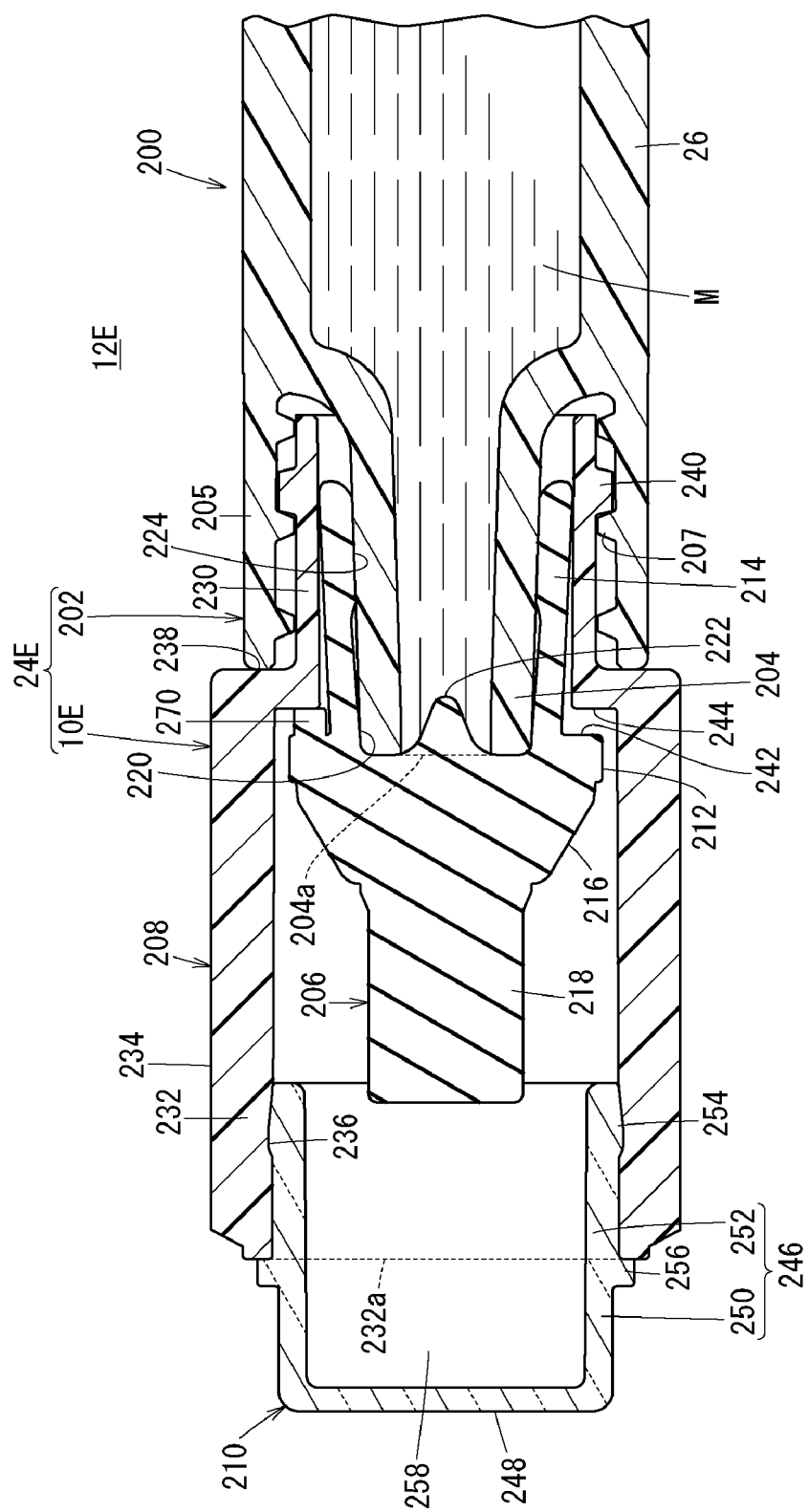
FIG. 26 is an enlarged longitudinal cross-sectional view of the distal end part of a prefilled syringe according to a fifth embodiment of the present invention.

As illustrated in FIG. 26, a syringe assembly 24E of the prefilled syringe 12E according to the present embodiment is provided with a cap 10E in place of the cap 10D. The cap 10E has a proximal end projection 270 (inclination promoting portion) protruding to the cylindrical connecting portion 230 side from a part of the proximal stepped surface 242 of the large-diameter portion 212 of the cap body 206. The proximal end projection 270 is configured as a columnar pin.

Figure 27A:
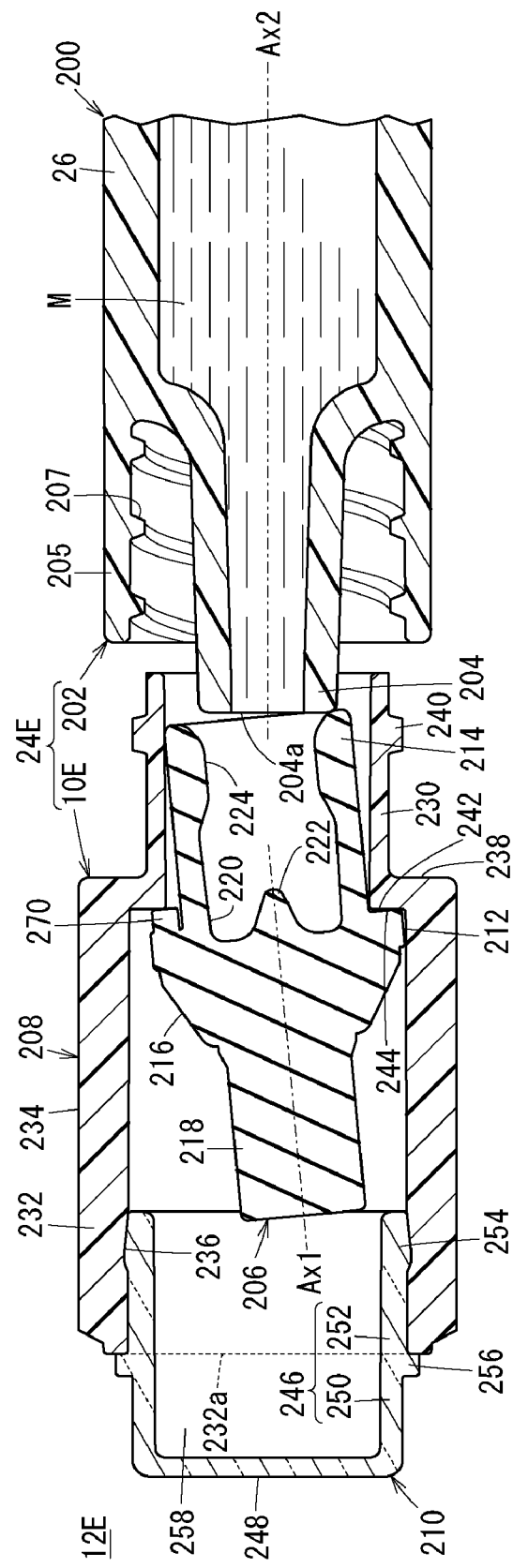
FIG. 27A is a longitudinal cross-sectional view illustrating a state in which a recap operation for the cap illustrated in FIG. 26 is in progress.
Figure 27B:
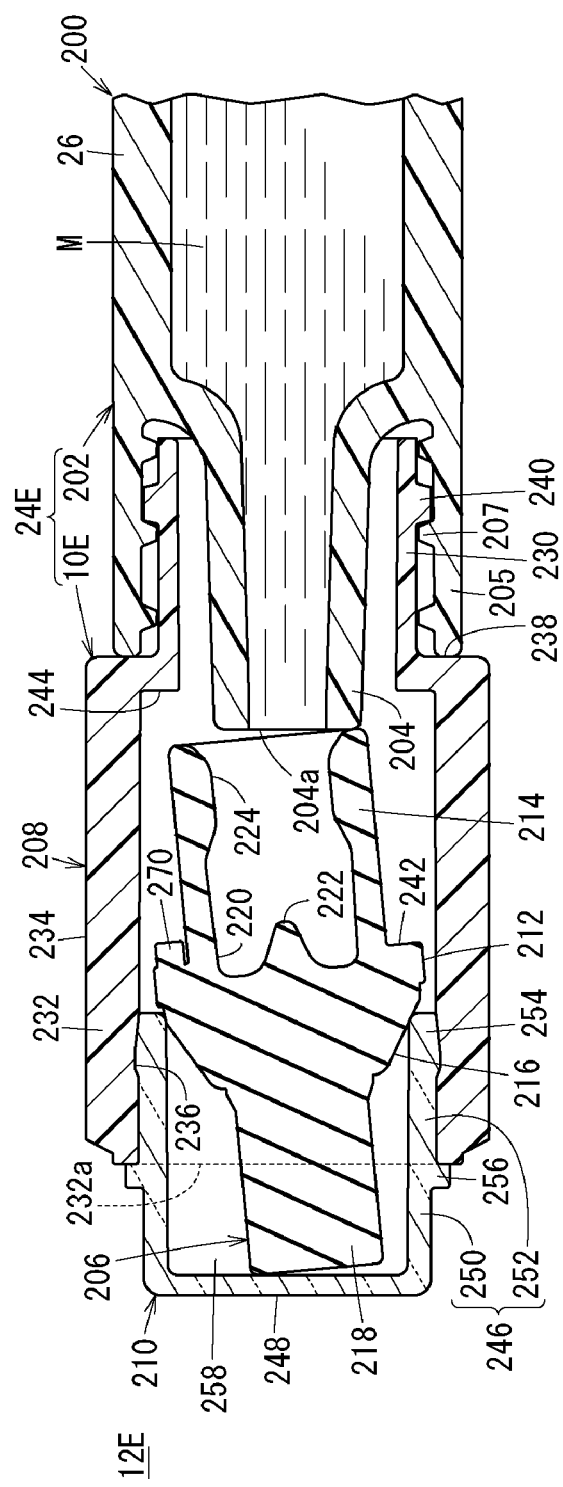
FIG. 27B is a longitudinal cross-sectional view illustrating a recapped state in which the recap operation is completed.

As illustrated in FIG. 27A, when the syringe outer tube 202 is recapped with the cap 10E after opening of the cap 10E in this configuration, the proximal end surface of the proximal end projection 270 comes into contact with the engaging stepped surface 244 of the cylindrical connecting portion 230 and an axis Ax1 of the cap body 206 is inclined with respect to an axis of the cylindrical connecting portion 230 (axis Ax2 of the nozzle portion 204). As a result, the proximal end surface or the abutting projecting portion 224 of the mounting tube portion 214 comes into contact with the distal end surface of the nozzle portion 204. Accordingly, it is possible to effectively suppress the mounting tube portion 214 being fitted over the nozzle portion 204 in a state in which the male screw portion 240 of the cylindrical connecting portion 230 is completely screwed in the female screw portion 207 of the syringe side connecting portion 205 (recapped state) as illustrated in FIG. 27B. It should be noted that the outer peripheral portion of the distal end protruding portion 218 as a viewing portion is invisible in the unopened state of the cap 10E and is visible in the recapped state as in the fourth embodiment. As a result, a user can easily and reliably discriminate between the unopened state and the recapped state of the cap 10E.

The present embodiment is not limited to the above-described configuration. For example, the cap body 206 may not be provided with the abutting projecting portion 224. In this case, the proximal end of the cap body 206 is configured to be displaced distally by being pressed by the distal end of the nozzle portion 204 with the axis Ax1 of the cap body 206 inclined with respect to the axis Ax2 of the nozzle portion 204 during remounting of the cap 10E on the syringe outer tube 202. In other words, the proximal end of the mounting tube portion 214 functions as an abutting portion. This also applies to a prefilled syringe 12F according to the sixth embodiment, which will be described below.

Sixth Embodiment

Figure 28:
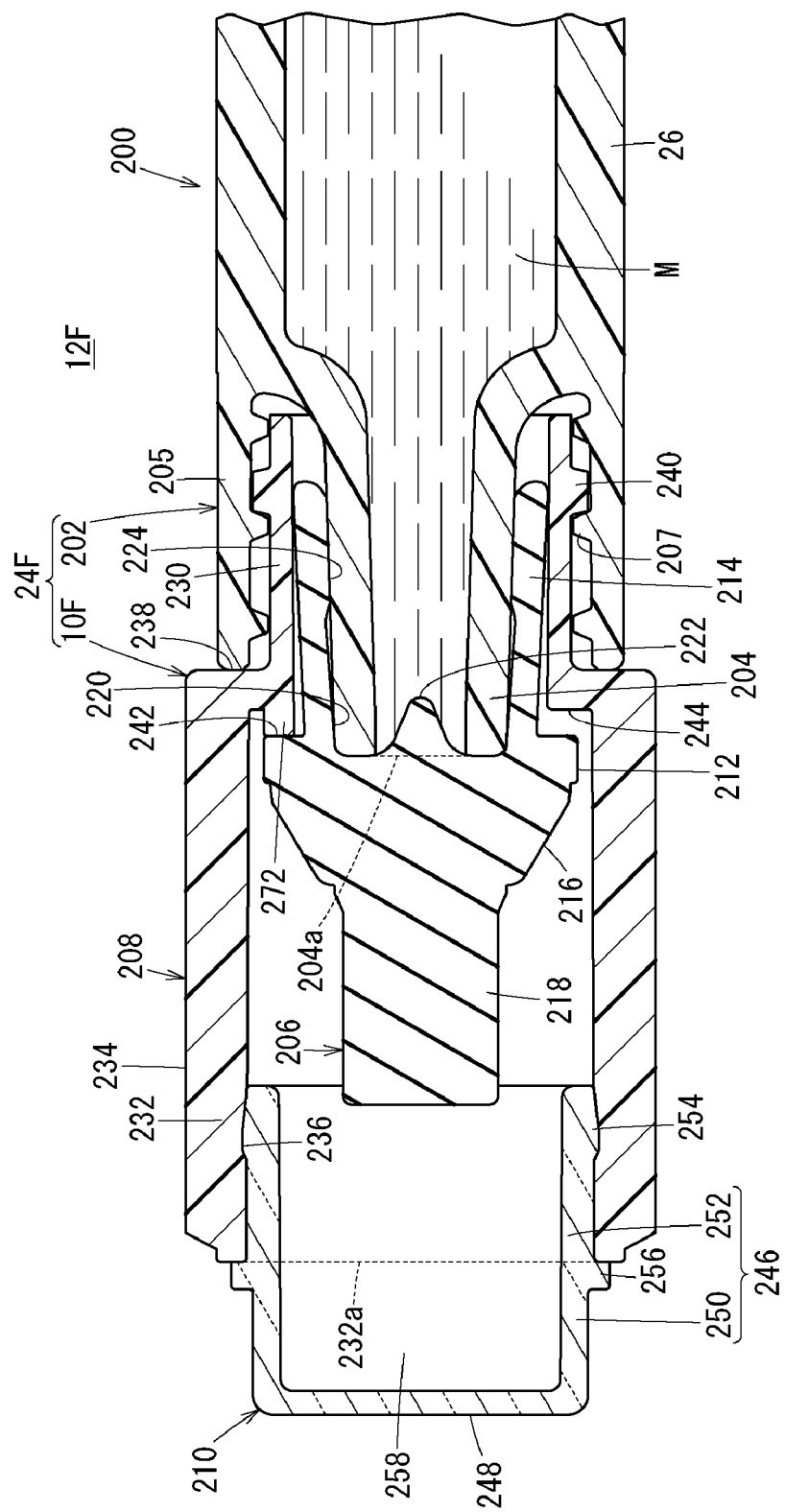
FIG. 28 is an enlarged longitudinal cross-sectional view of the distal end part of a prefilled syringe according to a sixth embodiment of the present invention.

Next, the prefilled syringe 12F according to the sixth embodiment of the present invention will be described. As illustrated in FIG. 28, a syringe assembly 24F of the prefilled syringe 12F according to the present embodiment is provided with a cap 10F in place of the cap 10D. The cap 10F has a distal end projection 272 (inclination promoting portion) protruding in the distal end direction from a part of the engaging stepped surface 244 of the cylindrical connecting portion 230. The distal end projection 272 is configured as a columnar pin.

Figure 29A:
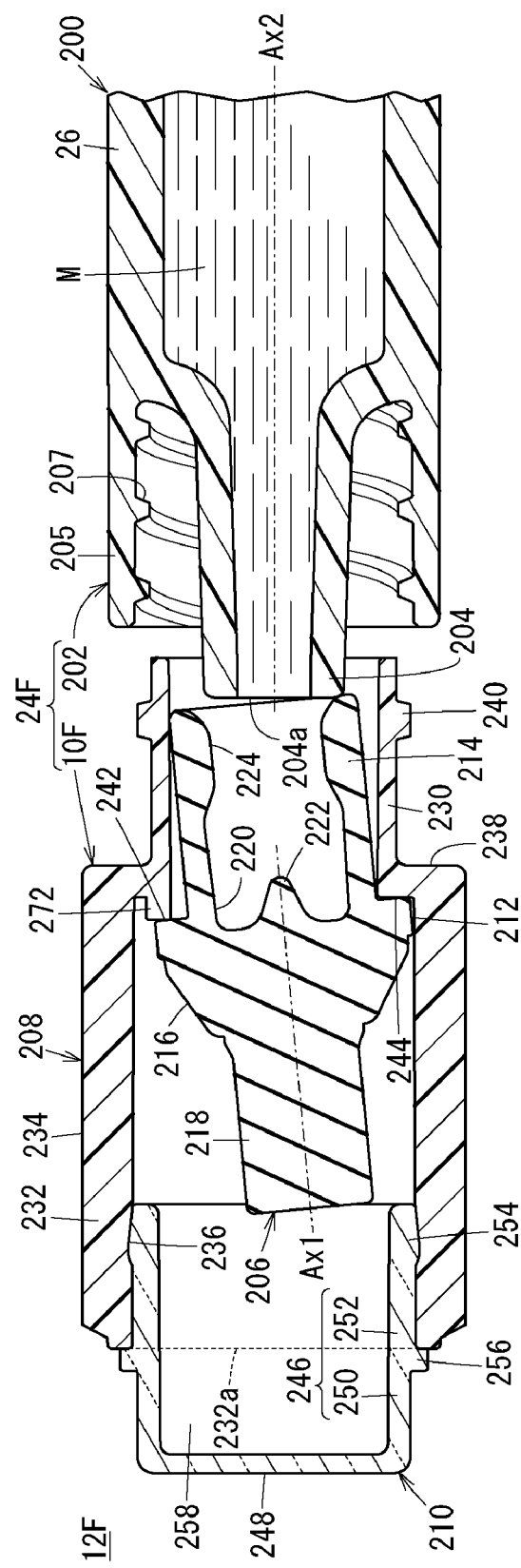
FIG. 29A is a longitudinal cross-sectional view illustrating a state in which a recap operation for the cap illustrated in FIG. 28 is in progress.
Figure 29B:
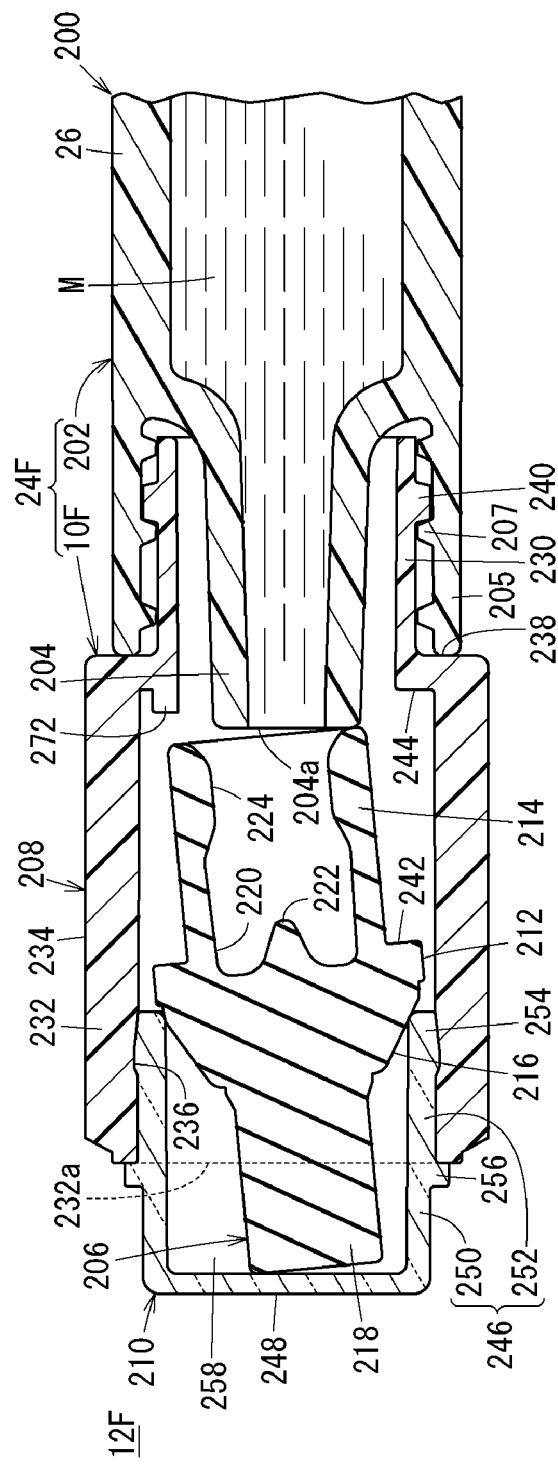
FIG. 29B is a longitudinal cross-sectional view illustrating a recapped state in which the recap operation is completed.

As illustrated in FIG. 29A, when the syringe outer tube 202 is recapped with the cap 10F after opening of the cap 10F in this configuration, the distal end surface of the distal end projection 272 comes into contact with the proximal stepped surface 242 of the large-diameter portion 212 and the axis Ax1 of the cap body 206 is inclined with respect to the axis of the cylindrical connecting portion 230 (axis Ax2 of the nozzle portion 204). As a result, the proximal end surface or the abutting projecting portion 224 of the mount-ing tube portion 214 comes into contact with the distal end surface of the nozzle portion 204 in a reliable manner. Accordingly, it is possible to effectively suppress the mounting tube portion 214 being fitted over the nozzle portion 204 in a state in which the male screw portion 240 of the cylindrical connecting portion 230 is completely screwed in the female screw portion 207 of the syringe side connecting portion 205 (recapped state) as illustrated in FIG. 29B. It should be noted that the outer peripheral portion of the distal end protruding portion 218 as a viewing portion is invisible in the unopened state of the cap 10F and is visible in the recapped state as in the fourth embodiment. As a result, a user can easily and reliably discriminate between the unopened state and the recapped state of the cap 10F.

Seventh Embodiment

Figure 30:
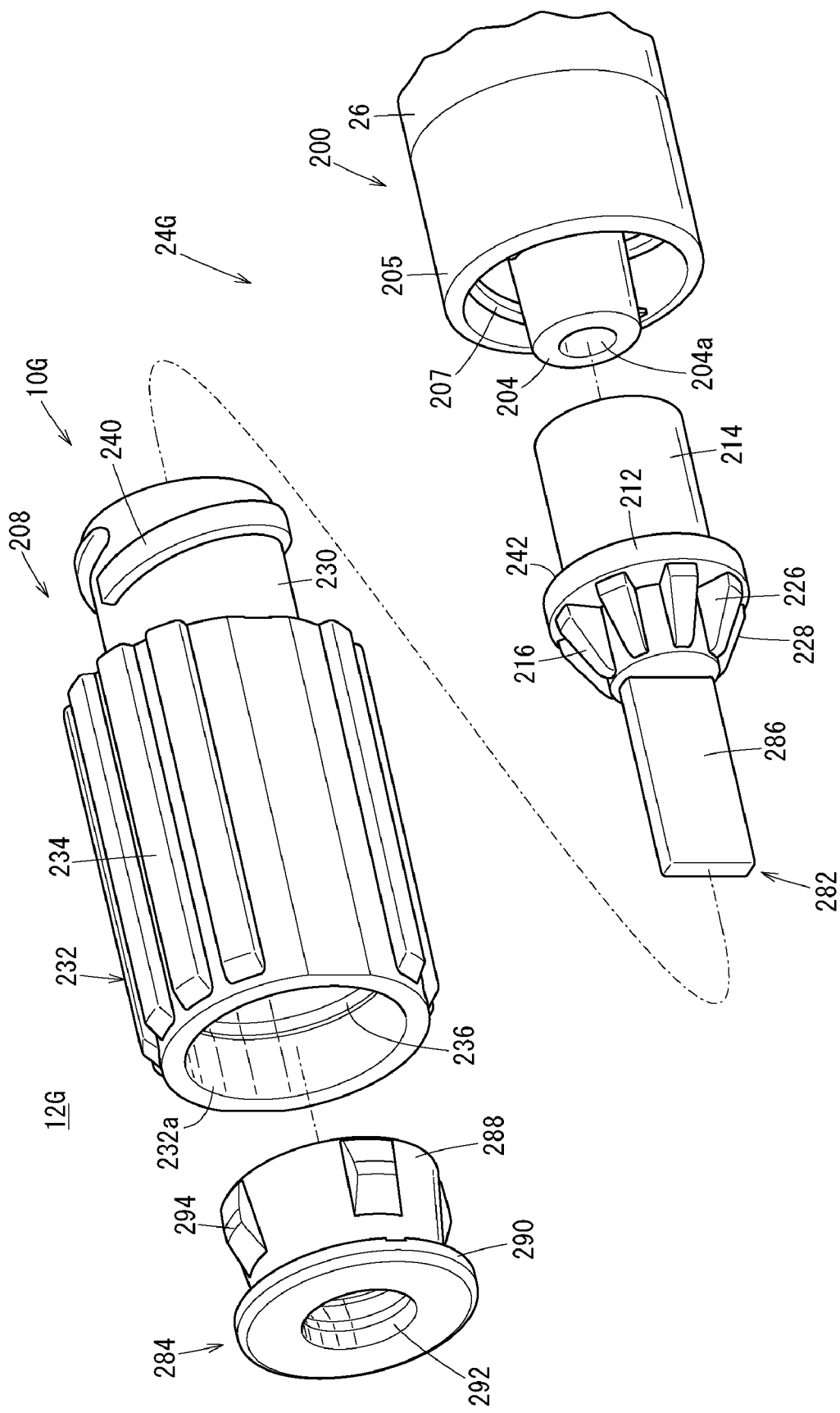
FIG. 30 is an exploded perspective view of the distal end part of a prefilled syringe according to a seventh embodiment of the present invention.
Figure 31A:
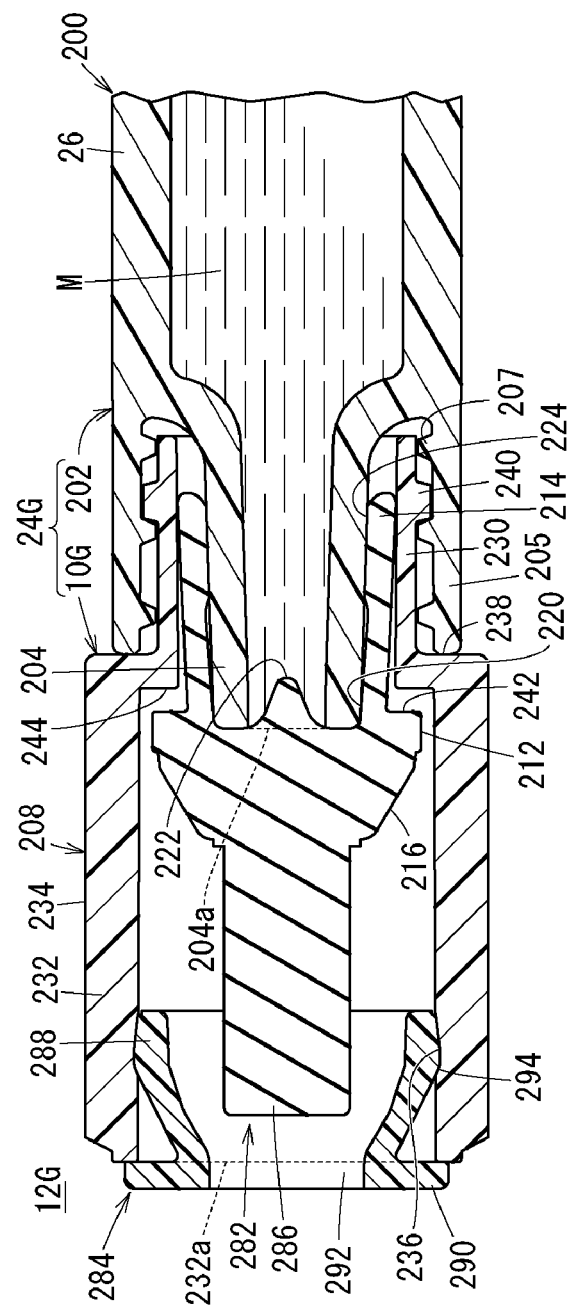
FIG. 31A is a longitudinal cross-sectional view illustrating the unopened state of the cap illustrated in FIG. 30.

Next, a prefilled syringe 12G according to the seventh embodiment of the present invention will be described. As illustrated in FIGS. 30 and 31A, a syringe assembly 24G of the prefilled syringe 12G according to the present embodiment is provided with a cap 10G in place of the cap 10D. The cap 10G has a cap body 282, the same cap cover 208 as in the fourth embodiment, and a distal end cover member 284.

The cap body 282 has a deformation-facilitated portion 286 in place of the distal end protruding portion 218. The deformation-facilitated portion 286 has a rectangular plate shape. The deformation-facilitated portion 286 is configured to be elastically deformed when pressed in the axial direction with a force weaker than the force that causes the abutting projecting portion 224 of the cap body 282 to be pressed by the distal end portion of the nozzle portion 204. In other words, the thickness of the deformation-facilitated portion 286 is set to a dimension that causes bending in the thickness direction of the deformation-facilitated portion 286 (direction orthogonal to the direction of the pressing) when the deformation-facilitated portion 286 is pressed in the axial direction with a force weaker than the force that causes the abutting projecting portion 224 of the cap body 282 to be pressed by the distal end portion of the nozzle portion 204. The deformation-facilitated portion 286 functions as a viewing portion as described later.

Although the cap body 282 is integrally formed of the same material in the present embodiment, a material softer than the constituent material of the other part of the cap body 282 (part other than the deformation-facilitated portion 286) may constitute the deformation-facilitated portion 286. In this case, the deformation-facilitated portion 286 can be elastically deformed with greater ease.

The shape of the deformation-facilitated portion 286 is not limited to the rectangular plate shape. For example, the deformation-facilitated portion 286 may have a substantially triangular or substantially trapezoidal plate shape formed so as to be narrow toward the direction of protrusion. In addition, the deformation-facilitated portion 286 may be columnar or tubular (hollow). Further, the deformation-facilitated portion 286 may be configured by a part of the distal end protruding portion 218 of the fourth embodiment being formed into a plate shape.

The distal end cover member 284 has an annular portion 288 fitted in the distal end portion of the cap cover 208 and a positioning projection 290 extending radially outward from the annular portion 288 and abutting against the distal end surface of the cap cover 208. In other words, a through hole 292 is formed in the distal end cover member 284. In the proximal end portion of the outer surface of the annular portion 288, a plurality of locking claws 294 configured to be mounted on the locking groove 236 of the cap cover 208 are disposed at equal intervals in the circumferential direction. The axially middle portion of the annular portion 288 gradually decreases in diameter toward the distal end portion of the annular portion 288.

The inner diameter of the distal end portion of the annular portion 288, which is the part where the hole diameter of the through hole 292 is minimized, is larger than the width dimension of the deformation-facilitated portion 286 and smaller than the outer diameter of the large-diameter portion 212. By the distal end portion of the annular portion 288 having a relatively small inner diameter as described above, it is difficult to operate the tapered portion 216 of the cap body 282 in the cap cover 208 via the through hole 292. The inner diameter of the through hole 292 is smaller than the outer diameter of the large-diameter portion 212. Accordingly, the distal end cover member 284 functions as a detachment blocking portion blocking the cap body 282 from being detached from the opening 232a of the cap cover 208 similarly to the distal end cover member 210 described above. The positioning projection 290 is disposed in the distal end portion of the annular portion 288. A material that has no transparency may constitute the distal end cover member 284 although the distal end cover member 284 is configured to be similar in constituent material to the distal end cover member 210 described above. It should be noted that the distal end cover member 284 does not cover the distal end portion of the cap body 282 at the second position unlike the distal end cover member 210 described above. In other words, the distal end cover member 284 has no contact blocking function.

Figure 31B:
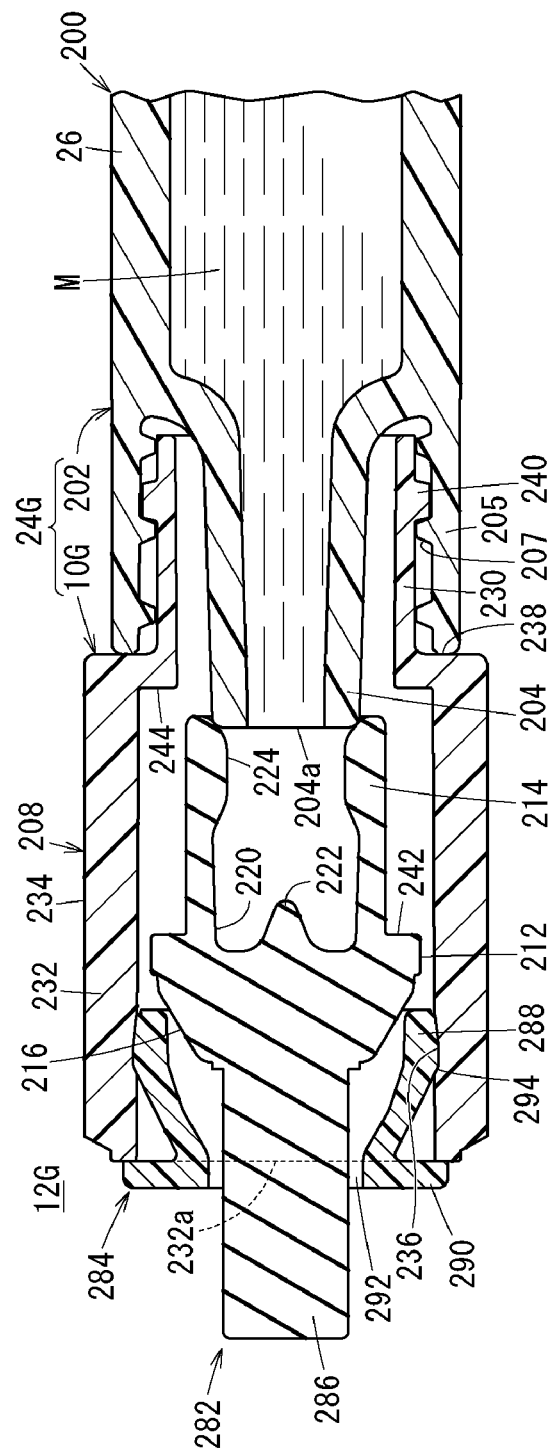
FIG. 31B is a longitudinal cross-sectional view illustrating the recapped state of the cap.

According to the present embodiment, the entire deformation-facilitated portion 286 is covered with the cap cover 208 in the unopened state of the cap 10G as illustrated in FIG. 31A. In other words, the deformation-facilitated portion 286 does not protrude from the opening 232a on the distal end side of the cap cover 208. In a case where the syringe outer tube 202 is recapped with the cap 10G after opening, abutting between the abutting projecting portion 224 of the cap body 282 and the distal end portion of the nozzle portion 204 causes the cap body 282 at the first position to be pressed by the nozzle portion 204 and displaced in the distal end direction with respect to the cap cover 208. Then, the deformation-facilitated portion 286 protrudes distally from the opening 232a on the distal end side of the cap cover 208. In other words, the deformation-facilitated portion 286, which is a viewing portion in the recapped state, is inserted through the through hole 292 of the distal end cover member 284 and protrudes (is exposed) to the outside of the cap cover 208 as illustrated in FIG. 31B. At this time, a user can directly view the deformation-facilitated portion 286. In other words, the outer peripheral portion of the deformation-facilitated portion 286 of the cap body 282 changes in appearance by the cap body 282 being displaced from the first position to the second position. Accordingly, it is possible to discriminate between the unopened state and the recapped state of the cap 10G with greater ease.

The deformation-facilitated portion 286 is bent (elastically deformed) in the thickness direction, and thus returning of the cap body 282 from the second position to the first position can be suppressed even in a case where a user presses the deformation-facilitated portion 286 from the outside of the cap cover 208 toward the syringe outer tube 202 side in the recapped state. As a result, it is possible to suppress the mounting tube portion 214 being fitted over the nozzle portion 204 in the recapped state. Since the hole diameter of the through hole 292 is smaller than the outer diameter of the large-diameter portion 212, it is difficult to return the cap body 282 from the second position to the first position by operating the tapered portion 216 of the cap body 282 in the cap cover 208 via the through hole 292. As a result, it is possible to suppress the mounting tube portion 214 being fitted over the nozzle portion 204.

The present embodiment is not limited to the above-described configuration. For example, the cap 10G may have the cap body 206 of the fourth embodiment. Even in this case, it is possible to directly view the distal end protruding portion 218 of the cap body 206 in the recapped state. The cap 10G may have the proximal end projection 270 of the fifth embodiment or the distal end projection 272 of the sixth embodiment. In other words, the cap 10G may have an inclination promoting portion.

Eighth Embodiment

Figure 32:
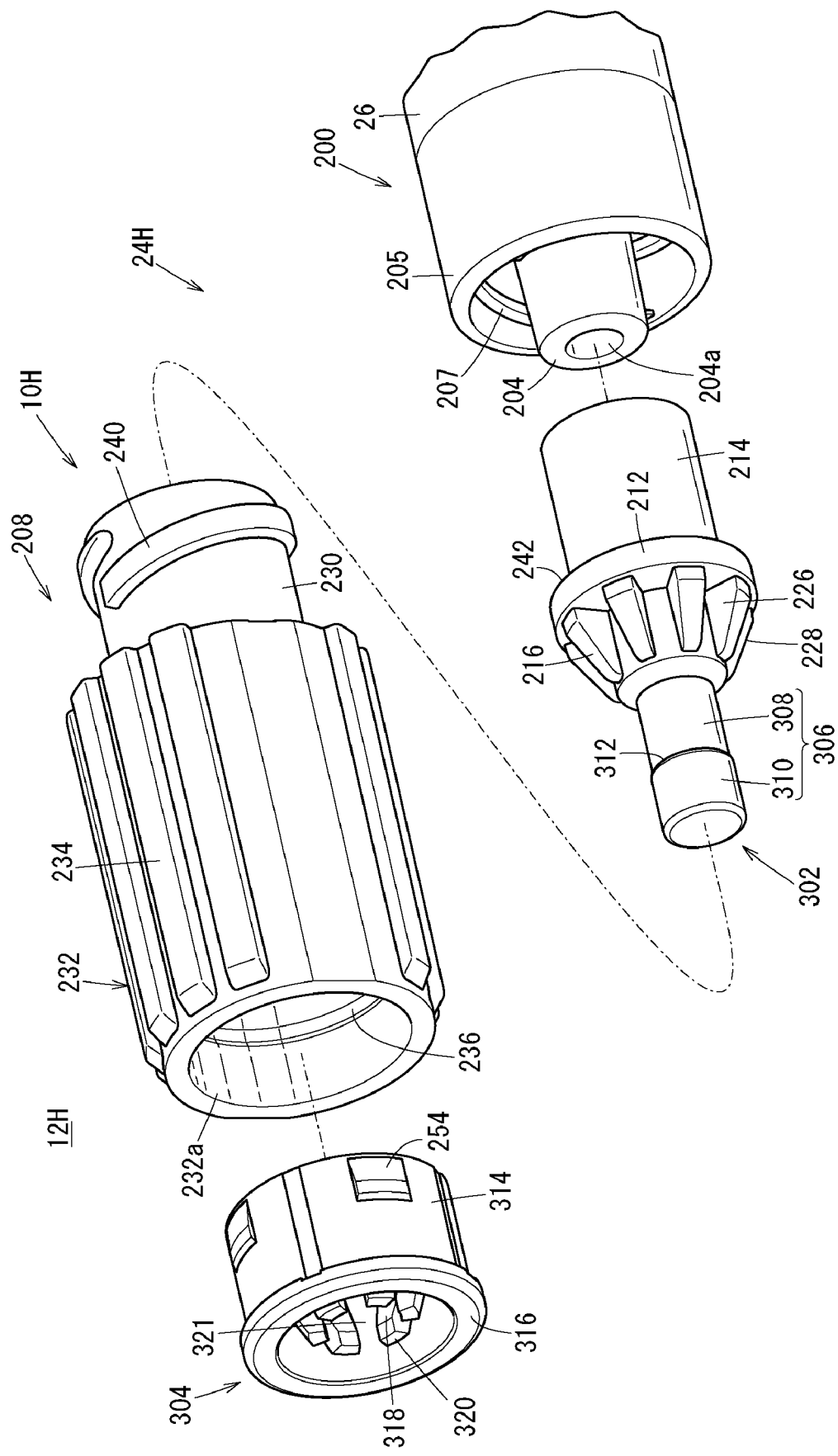
FIG. 32 is an exploded perspective view of the distal end part of a prefilled syringe according to an eighth embodiment of the present invention.
Figure 33A:
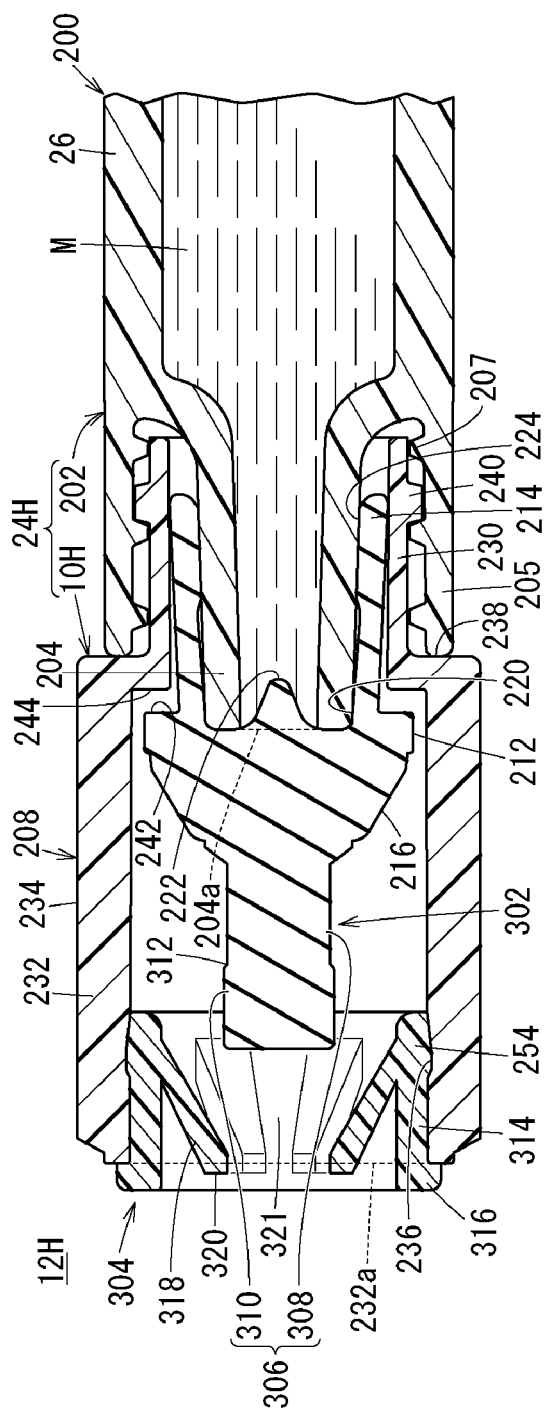
FIG. 33A is a longitudinal cross-sectional view illustrating the unopened state of the cap illustrated in FIG. 32.

Next, a prefilled syringe 12H according to the eighth embodiment of the present invention will be described. As illustrated in FIGS. 32 and 33A, a syringe assembly 24H of the prefilled syringe 12H according to the present embodiment is provided with a cap 10H in place of the cap 10D. The cap 10H has a cap body 302, the same cap cover 208 as in the fourth embodiment, and a distal end cover member 304.

A distal end protruding portion 306 of the cap body 302 has a proximal portion 308 having a constant outer diameter and a protruding end portion 310 larger in diameter than the proximal portion 308. An annular first stopper surface 312 facing the proximal direction is formed in the boundary portion between the proximal portion 308 and the protruding end portion 310. The first stopper surface 312 constitutes a part of the outer peripheral surface of the cap body 302. The distal end protruding portion 306 functions as a viewing portion as described later.

The distal end cover member 304 has an annular portion 314 fitted in the distal end portion of the cap cover 208 and a positioning projection 316 extending radially outward from annular portion 314 and abutting against the distal end surface of the cap cover 208. In the proximal end portion of the annular portion 314, the plurality of locking claws 254 configured to be mounted on the locking groove 236 of the cap cover 208 are disposed at equal intervals in the circumferential direction. The inner diameter of the annular portion 314 is smaller than the outer diameter of the large-diameter portion 212. A plurality of (six in FIG. 32) displacement restricting portions 318 configured to come into contact with the distal end protruding portion 306 are disposed in the proximal end portion of the inner peripheral surface of the annular portion 314.

The plurality of displacement restricting portions 318 are disposed at equal intervals (at intervals) in the circumferential direction of the annular portion 314. Each displacement restricting portion 318 is an elastic claw that has elasticity and extends to the front of the distal end of the annular portion 314 so as to be inclined radially inward from the proximal end portion of the annular portion 314 toward the distal end direction. The interval between the distal ends of the two displacement restricting portions 318 that face each other (inner diameter formed by the protruding ends of the plurality of displacement restricting portions 318) is slightly smaller than the outer diameter of the protruding end portion 310 of the distal end protruding portion 306 in a state in which the displacement restricting portion 318 is not in contact with the distal end protruding portion 306.

A second stopper surface 320 configured to come into contact with the first stopper surface 312 of the distal end protruding portion 306 is formed in the distal end portion of each displacement restricting portion 318. The second stopper surface 320 is a flat surface facing the direction that is opposite to the cylindrical connecting portion 230 (distal end direction). Each displacement restricting portion 318, which is an elastic claw, is configured to be enlarged in diameter outward in the radial direction of the annular portion 314 by the root portion of the displacement restricting portion 318 being bent.

The positioning projection 316 is disposed in the distal end portion of the annular portion 314. A material that has no transparency may constitute the distal end cover member 304 although the distal end cover member 304 is configured to be similar in constituent material to the distal end cover member 210 described above. A through hole 321 configured to allow the distal end protruding portion 306 to be inserted through the through hole 321 is formed in the distal end cover member 304. The inner diameter of the through hole 321 is smaller than the outer diameter of the large-diameter portion 212. Accordingly, the distal end cover member 304 functions as a detachment blocking portion blocking the cap body 302 from being detached from the opening 232a of the cap cover 208 similarly to the distal end cover member 210 described above. It should be noted that the distal end cover member 304 does not cover the distal end portion of the cap body 302 at the second position unlike the distal end cover member 210 described above. In other words, the distal end cover member 304 has no contact blocking function.

Figure 33B:
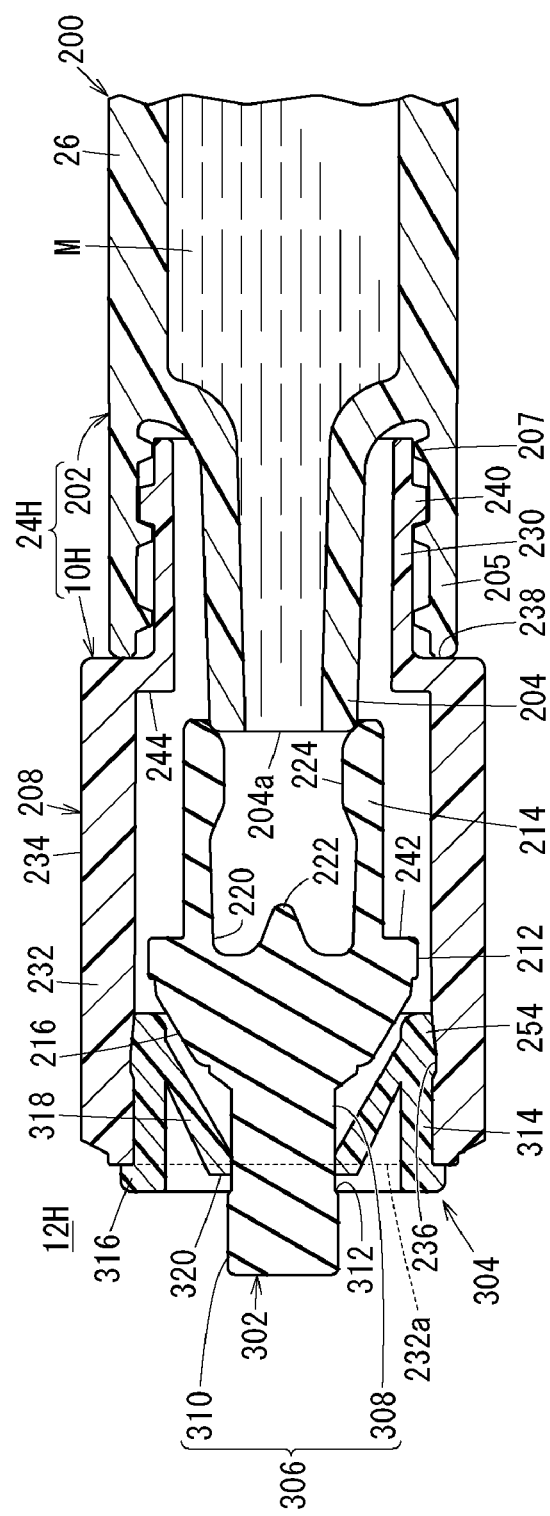
FIG. 33B is a longitudinal cross-sectional view illustrating the recapped state of the cap.

According to the present embodiment, the entire distal end protruding portion 306 is covered with the cap cover 208 in the unopened state of the cap 10H as illustrated in FIG. 33A. In other words, the distal end of the cap 10H is positioned proximal of the opening 232a on the distal end side of the cap cover 208. In other words, the distal end protruding portion 306 does not protrude from the opening 232a of the cap cover 208. In a case where the syringe outer tube 202 is recapped with the cap 10H after opening, abutting between the abutting projecting portion 224 of the cap body 302 and the distal end portion of the nozzle portion 204 causes the cap body 302 at the first position to be pressed by the nozzle portion 204 and displaced in the distal end direction with respect to the cap cover 208. Then, the distal end protruding portion 306 protrudes distally from the opening 232a on the distal end side of the cap cover 208. In other words, the distal end protruding portion 306, which is a viewing portion in the recapped state, is inserted through the through hole 321 of the distal end cover member 304 and protrudes (is exposed) to the outside of the cap cover 208 as illustrated in FIG. 33B. At this time, a user can directly view the distal end protruding portion 306. Accordingly, it is possible to discriminate between the unopened state and the recapped state of the cap 10H with greater ease. In addition, the cap body 302 is configured to climb over the displacement restricting portion 318 from the proximal end side by means of the force that causes the abutting projecting portion 224 (abutting portion) of the cap body 302 to be pressed by the distal end portion of the nozzle portion 204. As a result, the cap body 302 reliably moves from the first position to the second position during recapping.

In the recapped state, the distal end portion of each displacement restricting portion 318 is in contact with the outer peripheral surface of the proximal portion 308. Accordingly, returning of the cap body 302 from the second position to the first position can be suppressed, even in a case where a user presses the protruding end portion 310 from the outside of the cap cover 208 toward the syringe outer tube 202 side, since the second stopper surface 320 comes into contact with the first stopper surface 312. As a result, it is possible to suppress the mounting tube portion 214 being fitted over the nozzle portion 204 in the recapped state.

According to the present embodiment, the displacement restricting portion 318 is elastically deformed outward by the distal end protruding portion 306 when the distal end protruding portion 306 climbs over the displacement restricting portion 318, and thus the distal end protruding portion 306 easily climbs over the displacement restricting portion 318.

Further, the plurality of displacement restricting portions 318 are disposed at intervals along the circumferential direction of the cylindrical main body 232, and thus the displacement restricting portion 318 is elastically deformed with ease and the distal end protruding portion 306 climbs over the displacement restricting portion 318 with greater ease.

The present embodiment is not limited to the above-described configuration. For example, the cap 10H may have the cap body 206 of the fourth embodiment. Even in this case, it is possible to directly view the distal end protruding portion 218 of the cap body 206 in the recapped state. The cap 10H may have the proximal end projection 270 of the fifth embodiment or the distal end projection 272 of the sixth embodiment. In other words, the cap 10H may have an inclination promoting portion.

The displacement restricting portion 318 does not necessarily have to be an elastic claw and may be a simple projection protruding from the inner peripheral surface of the distal end cover member 304. In this case, the projection is configured to restrict displacement of the cap body 302 from the second position to the first position by engagement with the first stopper surface 312 (outer peripheral surface) of the cap body 302 at the second position and such that the cap body 302 (distal end protruding portion 306) is configured to climb over the projection from the proximal end side by means of the force that causes the abutting projecting portion 224 (abutting portion) of the cap body 302 to be pressed by the distal end portion of the nozzle portion 204.

Further, the first stopper surface 312 of the cap body 302 may be omitted. In this case, the displacement restricting portion 318 restricts displacement of the cap body 302 from the second position to the first position by engagement with the outer peripheral surface of the cap body 302 at the second position such as the outer peripheral surface of the distal end protruding portion 306.

Moreover, the displacement restricting portion 318 may be disposed as a projection protruding from the inner peripheral surface of the cap cover 208 instead of the distal end cover member 304. In this case, the distal end cover member 304 can be omitted.

Ninth Embodiment

Figure 35A:
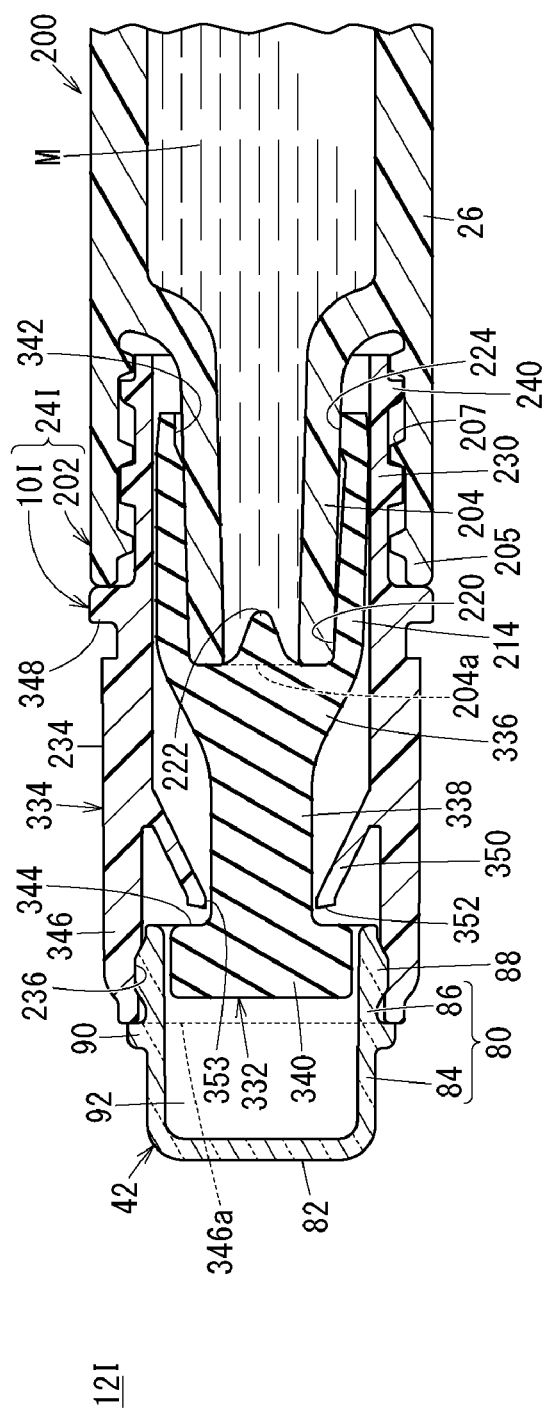
FIG. 35A is a longitudinal cross-sectional view illustrating the unopened state of the cap illustrated in FIG. 34.

Next, a prefilled syringe 12I according to the ninth embodiment of the present invention will be described. As illustrated in FIGS. 34 and 35A, a syringe assembly 24I of the prefilled syringe 12I according to the present embodiment is provided with a cap 10I. The cap 10I has a cap body 332, a cap cover 334, and the distal end cover member 42 similar to that of the first embodiment.

The cap body 332 has the mounting tube portion 214, a tapered portion 336 extending in the distal end direction from the distal end of the mounting tube portion 214, a small-diameter middle portion 338 extending in the distal end direction from the distal end of the tapered portion 336, and a large-diameter distal end portion 340 disposed at the distal end of the small-diameter middle portion 338. The large-diameter distal end portion 340 functions as a viewing portion as described later.

A circumferential part of the abutting projecting portion 224 of the mounting tube portion 214 is notched by a notch portion 342. The notch portion 342 extends over the entire length of the abutting projecting portion 224 along the axial direction of the mounting tube portion 214. In other words, a circumferential part of the abutting projecting portion 224 is recessed radially outward.

The outer peripheral surface of the tapered portion 336 is reduced in diameter in a tapered shape from the distal end of the mounting tube portion 214 to the proximal end of the small-diameter middle portion 338. The small-diameter middle portion 338 has an outer diameter smaller than the outer diameters of the large-diameter distal end portion 340 and the mounting tube portion 214 over the entire length of the small-diameter middle portion 338. A proximal stepped surface 344 facing the proximal direction is formed in the boundary portion between the large-diameter distal end portion 340 and the small-diameter middle portion 338. The outer diameter of the large-diameter distal end portion 340 is larger than the outer diameter of the distal end portion of the nozzle portion 204 and slightly smaller than the inner diameter of the annular portion 80.

The cap cover 334 is configured to have a cylindrical shape and is made of a resin material having no transparency (substantially opaque resin material). Alternatively, the cap cover 334 may be made of a transparent material. The cap cover 334 has the cylindrical connecting portion 230 positioned in the proximal end portion of the cap cover 334, a cylindrical main body 346 extending in the distal end direction from the distal end of the cylindrical connecting portion 230, and an opening 346a disposed at the distal end of the cylindrical main body 346.

The cylindrical main body 346 is formed so as to have a size that allows a user to easily grasp the cylindrical main body 346 with his or her fingers. The non-slip portion 234 functioning as a non-slip portion for a user's fingers is formed on the outer peripheral surface of the cylindrical main body 346. The annular locking groove 236 for locking the distal end cover member 42 is formed in the distal end portion of the inner peripheral surface of the cylindrical main body 346. An insertion restricting portion 348 is disposed at the proximal end of the cylindrical main body 346. The insertion restricting portion 348 protrudes radially outward from the outer peripheral surface of the cylindrical main body 346 so as to be configured to abut against the distal end of the syringe side connecting portion 205. The length of insertion of the cylindrical connecting portion 230 into the space between the syringe side connecting portion 205 and the nozzle portion 204 is restricted by the insertion restricting portion 348 abutting against the distal end of the syringe side connecting portion 205.

The outer diameter of the cap 10I is equal to or smaller than the outer diameter of the syringe side connecting portion 205 over the entire length of the cap 10I. Specifically, the outer diameter of the cylindrical main body 346 is smaller than the outer diameter of the syringe side connecting portion 205 and the outer diameter of the insertion restricting portion 348 is equal to the outer diameter of the syringe side connecting portion 205.

The inner peripheral surface of the cylindrical main body 346 and the inner peripheral surface of the cylindrical connecting portion 230 form one circumferential surface continuously with each other. A plurality of engaging claw portions 350 (engaging portions, engaging projections), which have elasticity and extend so as to be inclined in the distal end direction, are disposed on the inner peripheral surface of the cylindrical main body 346 that is proximal of the locking groove 236.

The plurality of engaging claw portions 350 are disposed at intervals along the circumferential direction of the cylindrical main body 346. Specifically, the plurality of engaging claw portions 350 are disposed at equal intervals along the circumferential direction of the cylindrical main body 346. In other words, a predetermined gap is formed between the engaging claw portions 350 facing each other. A protruding end portion 352 of each engaging claw portion 350 faces the distal end direction so as to be configured to come into contact with the proximal stepped surface 344. The protruding end portion 352 of each engaging claw portion 350 is positioned more proximally than the distal end cover member 42. The inner diameter of a central hole 353 formed by the protruding ends (inner end portions) of the plurality of engaging claw portions 350 is larger than the outer diameter of the small-diameter middle portion 338. The inner diameter of the part from the proximal end of the cap cover 334 to the engaging claw portion 350 has an inner diameter larger than the outer diameter of the large-diameter distal end portion 340.

In the present embodiment, the large-diameter distal end portion 340 is positioned between the opening of the cap cover 334 and the engaging claw portion 350 in a state in which the cap body 332 is at the first position. The axial length of the small-diameter middle portion 338 is longer than the distance from the proximal stepped surface 344 of the large-diameter distal end portion 340 to the opening of the cap cover 334 in a state in which the cap body 332 is at the first position. It should be noted that the distal end cover member 42 of the present embodiment is mounted on the cap cover 334 by the locking claw 88 being fitted into the locking groove 236 of the cap cover 334.

Figure 36A:
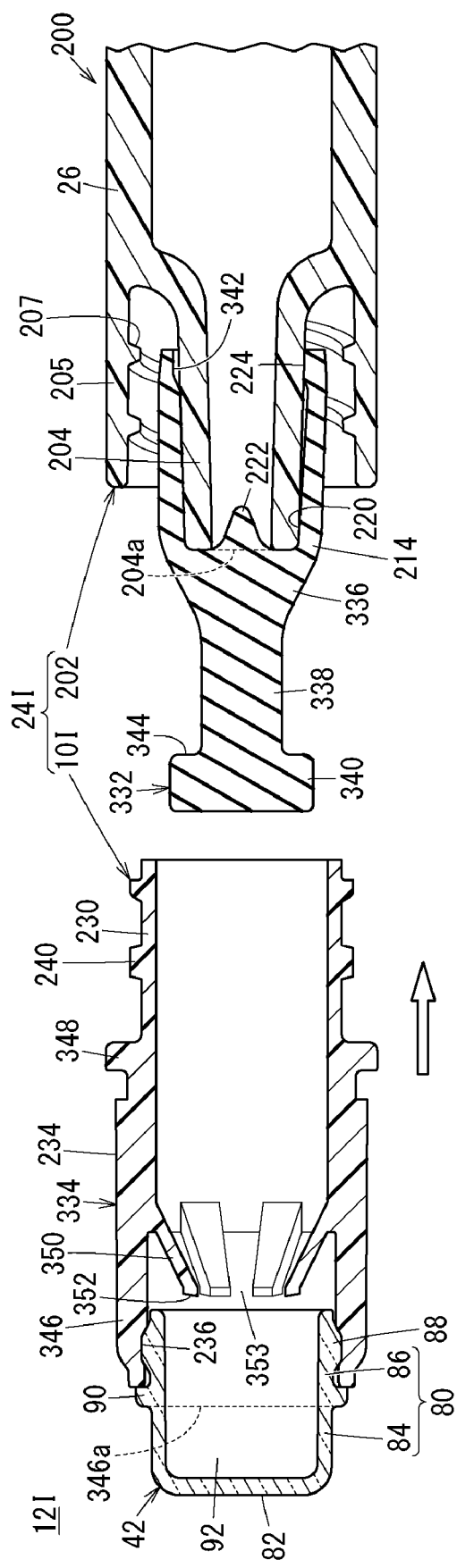
FIG. 36A is a first explanatory cross-sectional view of an assembly method for the cap illustrated in FIG. 34.

In a case where the cap 10I is assembled in the prefilled syringe 12I according to the present embodiment, the mounting tube portion 214 of the cap body 332 is fitted first, over the nozzle portion 204 of the syringe outer tube 202, as illustrated in FIG. 36A. At this time, the distal end portion of the nozzle portion 204 is allowed to abut against the sealing portion 220 of the cap body 332.

Figure 36B:
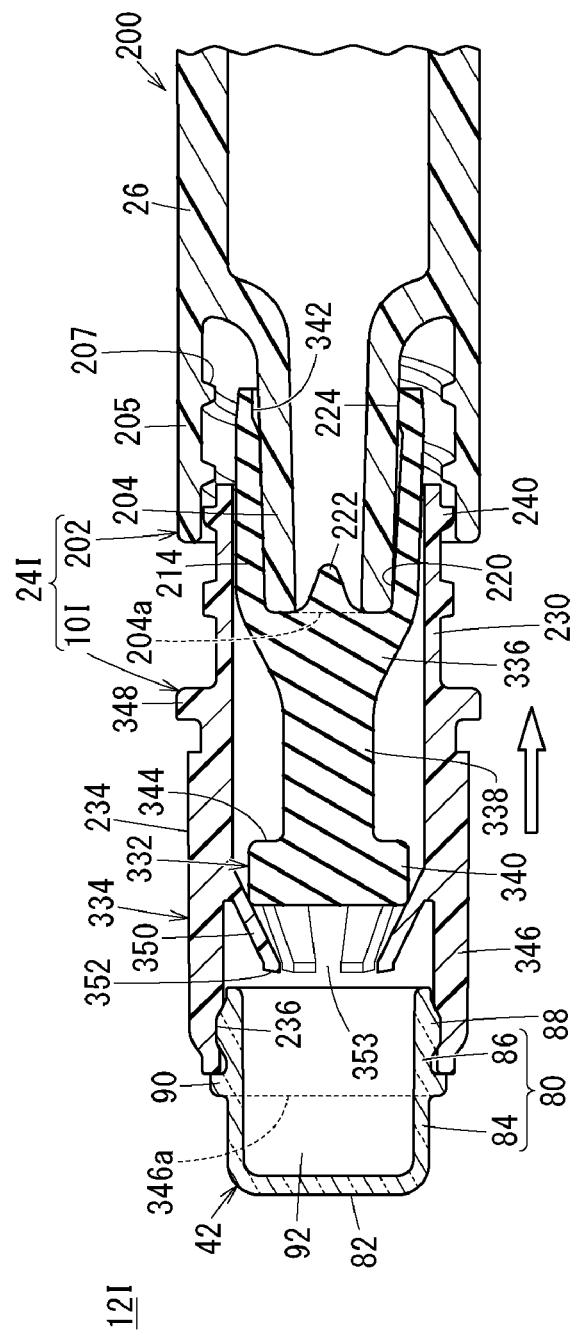
FIG. 36B is a second explanatory cross-sectional view of the assembly method for the cap.

Subsequently, the large-diameter distal end portion 340 is inserted from the proximal end side of the cap cover 334 with the distal end cover member 210 mounted and the large-diameter distal end portion 340 is brought into contact with each engaging claw portion 350 (FIG. 36B). Then, the cylindrical main body 346 and the syringe outer tube 202 are brought close to each other. As a result, the large-diameter distal end portion 340 is displaced in the distal end direction beyond each engaging claw portion 350 while each engaging claw portion 350 is elastically deformed radially outward. Subsequently, the cap 10I is mounted with respect to the syringe outer tube 202 by the male screw portion 240 of the cylindrical connecting portion 230 being screwed into the female screw portion 207 of the syringe side connecting portion 205. Configured as a result is the syringe assembly 24I provided with the syringe outer tube 202 and the cap 10I. It should be noted that mounting of the distal end cover member 42 onto the cap cover 334 may be performed after the cylindrical connecting portion 230 is completely mounted on the syringe side connecting portion 205.

In a state in which the cap 10I is completely mounted on the syringe outer tube 202, the cap body 332 is positioned at the first position, where the large-diameter distal end portion 340 is distal of the engaging claw portion 350. At this time, the distal end surface of the large-diameter distal end portion 340 is positioned in the engagement extending portion 86. In addition, the sealing portion 220 of the mounting tube portion 214 seals the drug discharge port 204a of the nozzle portion 204 and the inner peripheral surface of the mounting tube portion 214 forms a circumferentially continuous airtight seal with the outer peripheral surface of the nozzle portion 204 at least in the vicinity of the distal end of the abutting projecting portion 224. As a result, sterility is ensured at the part of the nozzle portion 204 that is positioned distal of the abutting projecting portion 224. The nozzle portion 204 has a tapered shape and decreases in outer diameter toward the distal end. Accordingly, when the sealing portion 220 of the mounting tube portion 214 is separated by a predetermined distance from the drug discharge port 204a of the nozzle portion 204 and the abutting projecting portion 224 abuts against the outer peripheral surface of the nozzle portion 204, the inner peripheral surface in the vicinity of the distal end of the abutting projecting portion 224 of the mounting tube portion 214 is separated from the outer peripheral surface of the nozzle portion 204 and the airtight seal is released. It should be noted that the inner peripheral surface of the mounting tube portion 214 may form a circumferentially continuous airtight seal with the outer peripheral surface of the nozzle portion 204 from the distal end of the mounting tube portion 214 to the vicinity of the distal end of the abutting projecting portion 224.

The prefilled syringe 12I is configured by the syringe outer tube 202 of the syringe assembly 24I configured as described above being filled with the drug M and the gasket 20 and the pusher 22 being mounted.

Figure 35B:
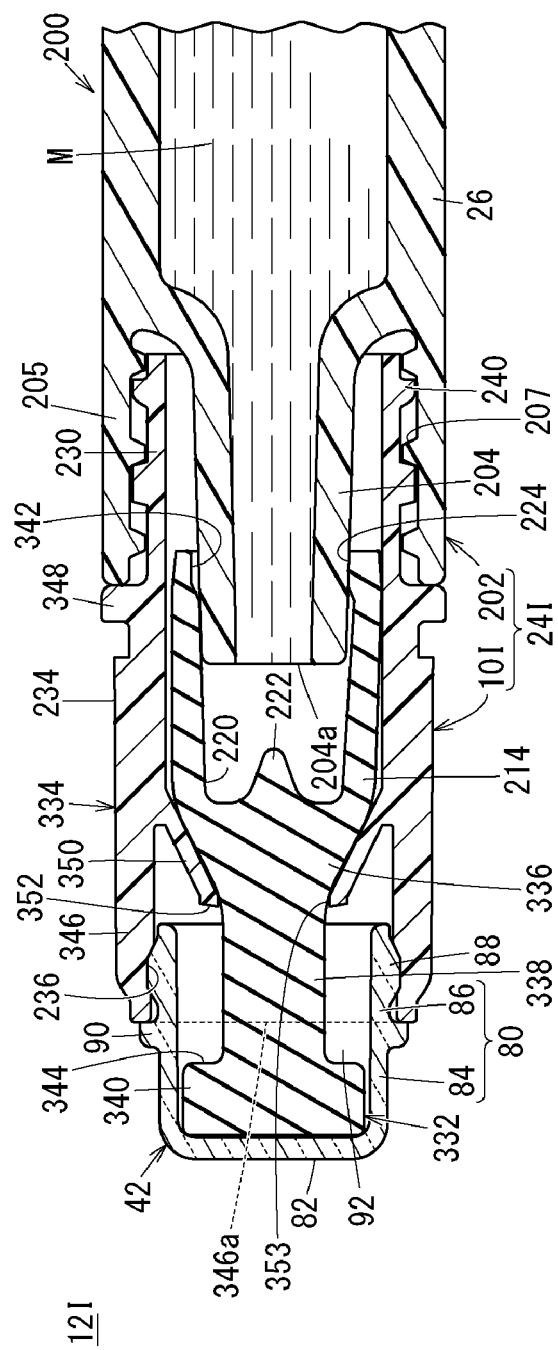
FIG. 35B is a longitudinal cross-sectional view illustrating the recapped state of the cap.

As illustrated in FIGS. 35A and 35B, in the present embodiment, the outer peripheral portion of the large-diameter distal end portion 340 as a viewing portion is invisible in the unopened state of the cap 10I and is visible in the recapped state. As a result, a user can easily and reliably discriminate between the unopened state and the recapped state of the cap 10I.

In the present embodiment, the notch portion 342 is formed in the abutting projecting portion 224. Accordingly, when the sealing portion 220 of the mounting tube portion 214 is separated by a predetermined distance from the drug discharge port 204a of the nozzle portion 204, the inside of the mounting tube portion 214 that is distal of the abutting projecting portion 224 communicates with the outside. As a result, the negative pressure in the mounting tube portion 214 is released during opening of the cap 10I and it is possible to inhibit the drug M in the nozzle portion 204 from being pulled by the negative pressure in the cap 10I and scattering when the cap 10I is disengaged from the syringe outer tube 202.

According to the present embodiment, the cap body 332 is fitted onto the nozzle portion 204, and then the large-diameter distal end portion 340 is inserted from the proximal end of the cap cover 334 and allowed to climb over the engaging claw portion 350. As a result, the cap body 332 is disposed at the first position and detachment of the cap body 332 in a proximal end direction with respect to the cap cover 334 is inhibited. As a result, the cap 10I can be assembled with ease.

When the large-diameter distal end portion 340 climbs over the engaging claw portion 350 during assembly of the cap 10I, the engaging claw portion 350 is elastically deformed outward by the large-diameter distal end portion 340, and thus the large-diameter distal end portion 340 climbs over the engaging claw portion 350 with ease.

Further, the plurality of engaging claw portions 350 are disposed at intervals along the circumferential direction of the cylindrical main body 346, and thus the engaging claw portion 350 is elastically deformed with ease. As a result, the large-diameter distal end portion 340 climbs over the engaging claw portion 350 with greater ease.

In the present embodiment, the outer diameter of the small-diameter middle portion 338 is smaller than the inner diameter formed by the inner end portion of the engaging claw portion 350 and the axial length of the small-diameter middle portion 338 is longer than the distance from the proximal stepped surface 344 of the large-diameter distal end portion 340 to the opening 346a of the cap cover 334 in a state in which the cap body 332 is at the first position. Accordingly, it is possible to inhibit the small-diameter middle portion 338 from being caught by the engaging claw portion 350 and inhibit displacement from being hindered during the displacement of the cap body 332 from the first position to the second position.

The outer diameter of the cap 10I is equal to or smaller than the outer diameter of the syringe side connecting portion 205, and thus the outer peripheral portion of the cap 10I does not protrude outward beyond the outer peripheral portion of the syringe side connecting portion 205. Accordingly, the cap 10I is unlikely to be caught by a feeder or the like when the syringe outer tube 202 is transported with the cap 10I mounted. Further, the large-diameter distal end portion 340 of the cap body 332 is larger than the distal end outer diameter of the nozzle portion 204, and thus a change in the appearance of the large-diameter distal end portion 340 can be easily understood.

Further, the cap 10I of the present embodiment is provided with the distal end cover member 42, which forms the receiving space 92 receiving the large-diameter distal end portion 340, on the side distal of the opening 346a of the cap cover 334. The cap cover 334 is substantially opaque, the distal end cover member 42 is transparent, and the inner diameter of the distal end cover member 42 is slightly larger than the outer diameter of the large-diameter distal end portion 340. Accordingly, the distal end cover member 42 does not hinder displacement of the cap body 332 from the first position to the second position and the large-diameter distal end portion 340 protruding from the opening 346a is easily visible even in a state in which the distal end cover member 42 is interposed.

The present embodiment is not limited to the above-described configuration. For example, the engaging projection does not necessarily have to have a claw shape and elasticity unlike the engaging claw portion 350. Specifically, the engaging projection may be a simple projection protruding from the inner peripheral surface of the cap cover 334. In addition, the projection may be disposed in an annular shape.

Tenth Embodiment

Figure 37A:
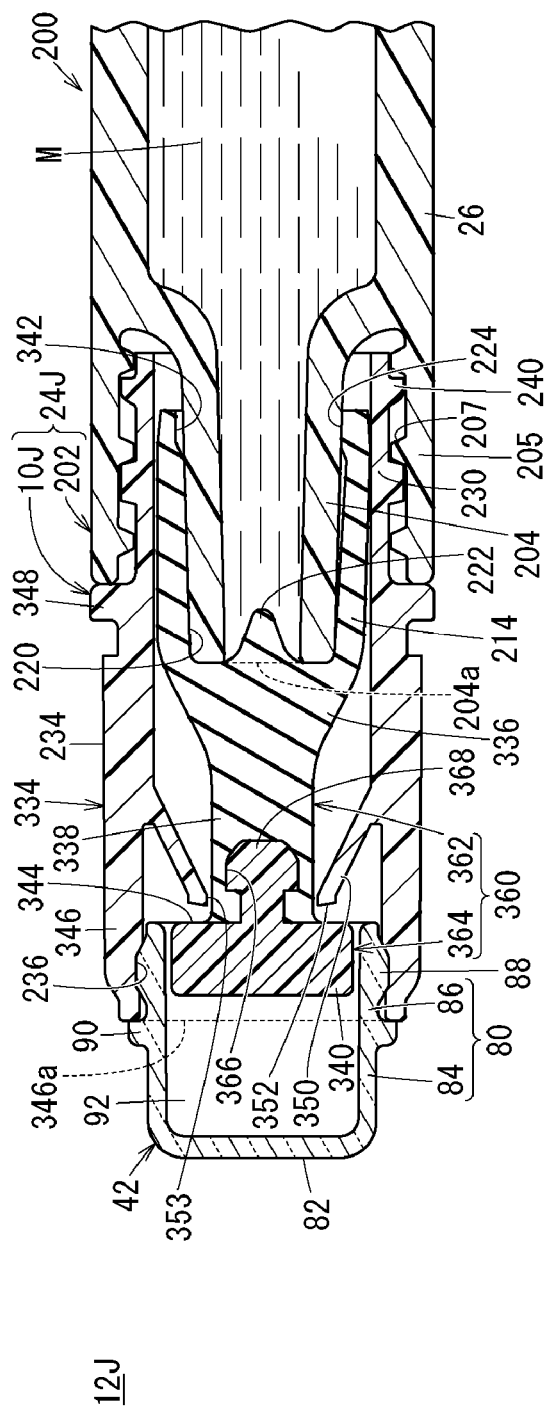
FIG. 37A is a longitudinal cross-sectional view illustrating the unopened state of the cap of a prefilled syringe according to a tenth embodiment of the present invention.
Figure 37B:
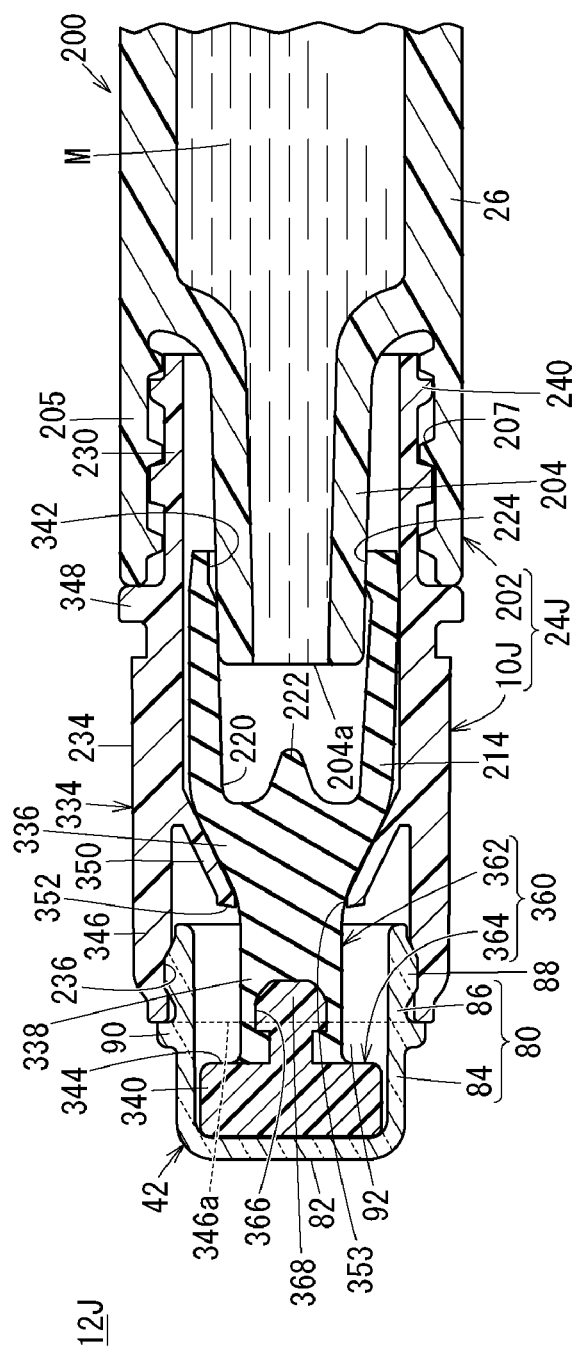
FIG. 37B is a longitudinal cross-sectional view illustrating the recapped state of the cap.

Next, a prefilled syringe 12J according to the tenth embodiment of the present invention will be described. As illustrated in FIGS. 37A and 37B, a syringe assembly 24J of the prefilled syringe 12J according to the present embodiment is provided with a cap 10J. The cap 10J has a cap body 360, the same cap cover 334 as in the ninth embodiment, and the same distal end cover member 42 as in the first embodiment.

The cap body 360 includes a first member 362 as a body member and a second member 364 constituting the distal end portion of the cap body 360. The first member 362 is provided with the mounting tube portion 214, the tapered portion 336, and the small-diameter middle portion 338. The first member 362 is made of a material that substantially contains no colorant. Examples of the material include isoprene rubber, butyl rubber, silicone rubber, and a thermoplastic elastomer that contain no colorant.

The second member 364 is provided with a connecting portion 368 fitted into a hole portion 366 formed in the distal end surface of the small-diameter middle portion 338 and the large-diameter distal end portion 340 disposed at the distal end of the connecting portion 368. The second member 364 is made of a material containing a colorant. Preferably, the colorant uses a color that a user can recognize with relative ease, such as red. The colorant may be of any color insofar as the color is different from the color of the first member 362. Preferably, the second member 364 is harder than the first member 362. Examples of the material include hard plastic such as colorant-containing polypropylene and polycarbonate.

As illustrated in FIGS. 37A and 37B, in the present embodiment, the outer peripheral portion of the large-diameter distal end portion 340 as a viewing portion is invisible in the unopened state of the cap 10J and is visible in the recapped state. As a result, a user can easily and reliably discriminate between the unopened state and the recapped state of the cap 10J.

According to the present embodiment, the mounting tube portion 214, which comes into contact with the drug M, contains no colorant. Accordingly, the drug M is not adversely affected when the cap 10J is mounted on the syringe outer tube 202 filled with the drug M. In addition, it is possible to easily discriminate between the unopened state and the recapped state of the cap 10J since the large-diameter distal end portion 340, which functions as a viewing portion, is colored.

The present embodiment is not limited to the above-described configuration. For example, the tapered portion 336 and the small-diameter middle portion 338 of the cap body 360 may be disposed in the second member 364.

Eleventh Embodiment

Figure 38:
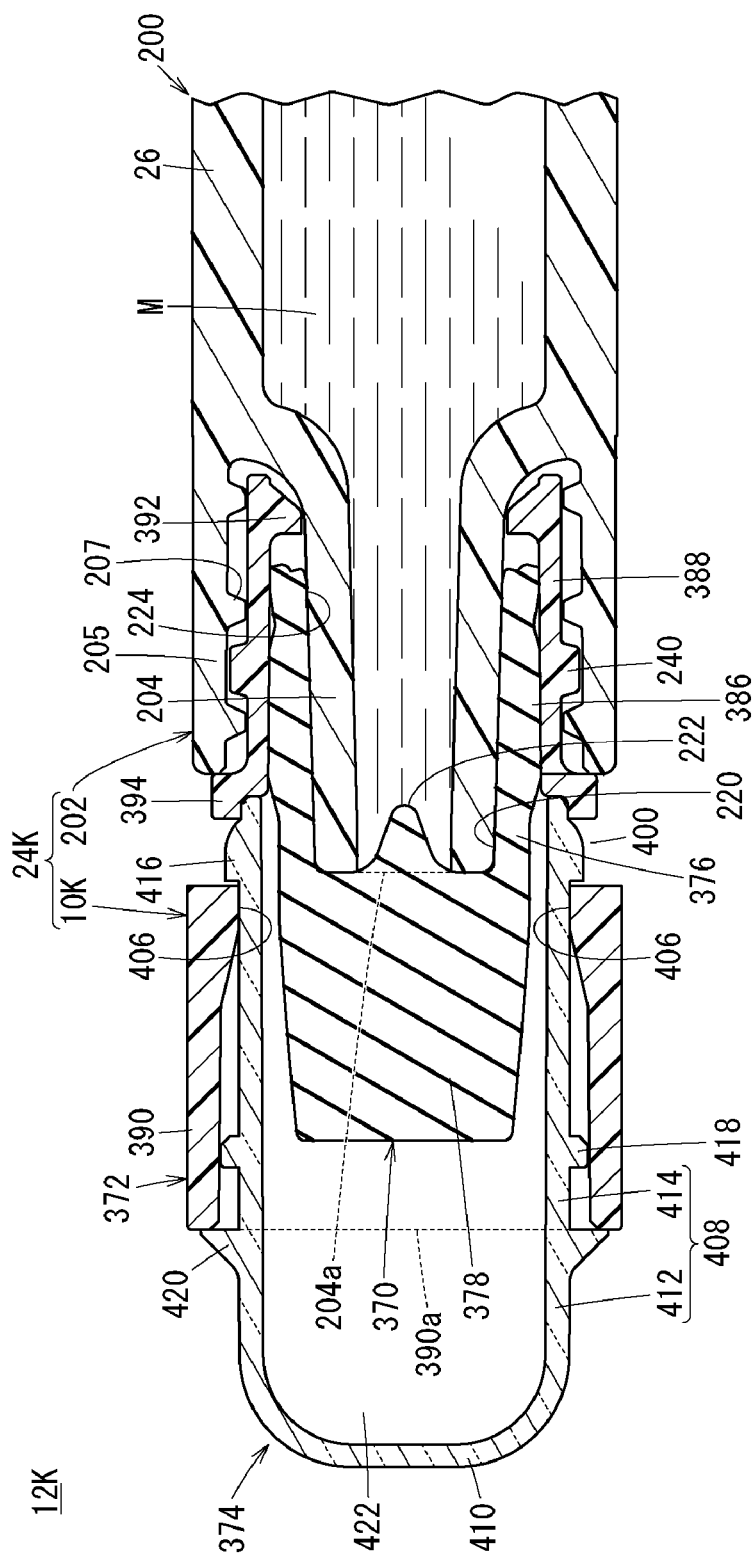
FIG. 38 is an enlarged longitudinal cross-sectional view of the distal end part of a prefilled syringe according to an eleventh embodiment of the present invention.
Figure 39:
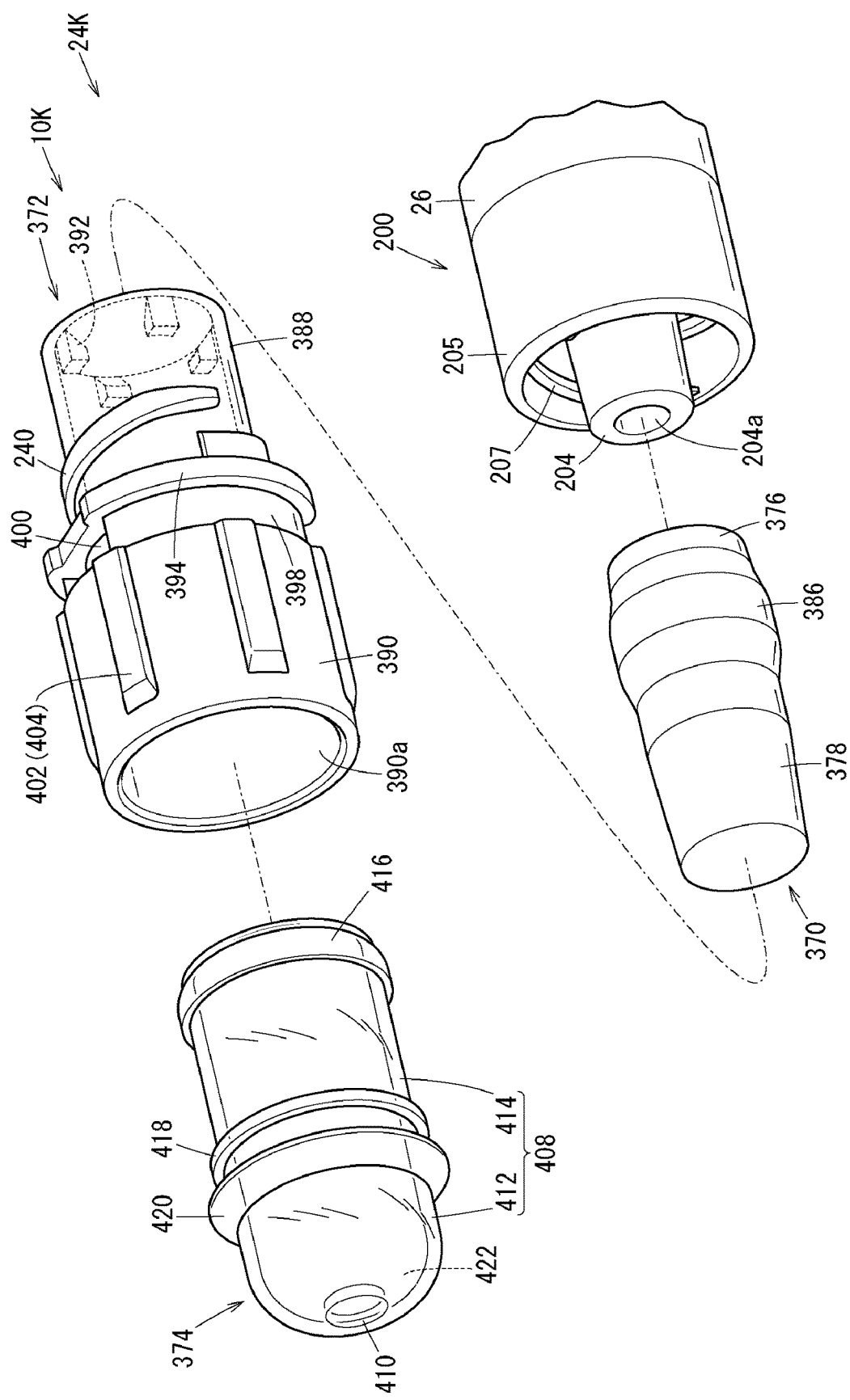
FIG. 39 is an exploded perspective view of the distal end part of the prefilled syringe illustrated in FIG. 38.

Next, a prefilled syringe 12K according to the eleventh embodiment of the present invention will be described. As illustrated in FIGS. 38 and 39, a syringe assembly 24K of the prefilled syringe 12K according to the present embodiment is provided with a cap 10K. The cap 10K has a cap body 370, a cap cover 372, and a distal end cover member 374.

The constituent material of the cap body 370 can be similar to the material of the cap body 38 described above. The cap body 370 includes a mounting tube portion 376 (mounting portion) and a distal end extending portion 378 extending in the distal end direction from the distal end of the mounting tube portion 376. The mounting tube portion 376 has the sealing portion 220 and the raised portion 222 raised from the sealing portion 220. The sealing portion 220 is configured to seal the drug discharge port 204a in a liquid-tight manner by being positioned in the distal end portion of the mounting tube portion 376. The sealing portion 220 abuts against the distal end portion of the nozzle portion 204. Specifically, the sealing portion 220 abuts against the distal end surface of the nozzle portion 204 or the side peripheral surface of the distal end portion of the nozzle portion 204. The drug discharge port 204a is sealed as a result. It should be noted that the drug discharge port 204a is sealed in a liquid-tight manner so that the drug M does not leak to the outside of the cap body 370. Accordingly, even in a case where the sealing portion 220 abuts against only the side peripheral surface of the distal end portion of the nozzle portion 204, the sealing portion 220 seals the drug discharge port 204a in a liquid-tight manner.

The abutting projecting portion 224 (abutting portion) similar to that of the fourth embodiment and configured to abut against the distal end portion of the nozzle portion 204 is disposed in the proximal end portion of the inner peripheral surface of the mounting tube portion 376. In the mounting state (unopened state) where the cap body 370 is mounted on the nozzle portion 204, the abutting projecting portion 224 is in contact with the outer peripheral surface of the nozzle portion 204 in a compressively deformed state.

An annular bulging portion 386 is disposed on the outer peripheral surface of the mounting tube portion 376. The bulging portion 386 is the part where the outer diameter of the cap body 370 is maximized. The bulging portion 386 is compressively deformed by being sandwiched between the nozzle portion 204 and a cylindrical connecting portion 388 in the mounting state of the cap body 370.

The distal end extending portion 378 functions as a viewing portion. The distal end extending portion 378 is configured to have a columnar shape. The distal end extending portion 378 may be colored in red or any other color that a user can recognize with relative ease. As for coloring of the distal end extending portion 378, the outer surface of the distal end extending portion 378 may be painted or pre-colored rubber or a pre-colored synthetic resin may constitute the cap body 370.

The cap cover 372 is configured to have a cylindrical shape and is made of a resin material having no transparency (substantially opaque resin material). Alternatively, the cap cover 372 may be made of a transparent material. The cap cover 372 has the cylindrical connecting portion 388 positioned in the proximal end portion of the cap cover 372 and detachable from the syringe side by screwing, a cylindrical main body 390 extending in the distal end direction from the distal end of the cylindrical connecting portion 388, and an opening 390a disposed at the distal end of the cylindrical main body 390 so that the cap body 370 is exposed from the cap cover 372.

A plurality of engaging claw portions 392 (engaging portions, engaging projections) extending radially inward are disposed in the proximal end portion of the inner peripheral surface of the cylindrical connecting portion 388. The plurality of engaging claw portions 392 are disposed at intervals along the circumferential direction of the cylindrical connecting portion 388. Specifically, the plurality of engaging claw portions 392 are disposed at equal intervals along the circumferential direction of the cylindrical connecting portion 388. The inner diameter of the hole that is formed by the protruding ends (inner end portions) of the plurality of engaging claw portions 392 is smaller than the outer diameter of the proximal end portion of the mounting tube portion 376 of the cap body 370. In other words, the surface of each engaging claw portion 392 that is oriented in the distal end direction is a flat surface extending in a direction orthogonal to the axis of the cap cover 372 and is configured to come into contact with the proximal end surface of the cap body 370. In addition, the engaging claw portion 392 has an inclined surface inclined inward in the distal end direction on the proximal end side of the engaging claw portion 392. As a result, the cap body 370 is capable of easily climbing over the engaging claw portion 392 when the cap body 370 is inserted into the cap cover 372 from the proximal end of the cap cover 372.

An insertion restricting portion 394 configured to abut against the distal end of the syringe side connecting portion 205 is disposed at the proximal end of the cylindrical main body 390. The length of insertion of the cylindrical connecting portion 388 into the space between the syringe side connecting portion 205 and the nozzle portion 204 is restricted by the insertion restricting portion 394 abutting against the distal end of the syringe side connecting portion 205. The cylindrical connecting portion 388 is a cylinder member disposed concentrically with the cap cover 372, and the male screw portion 240 configured to be screwed into the female screw portion 207 is formed on the outer peripheral surface of the cylindrical connecting portion 388.

The cylindrical main body 390 is formed so as to have a size that allows a user to easily grasp the cylindrical main body 390 with his or her fingers. An annular recess 398 is formed in the proximal end portion of the outer peripheral surface of the cylindrical main body 390. Two through holes 400 are formed in the bottom surface of the annular recess 398. The two through holes 400 face each other.

A non-slip portion 402 functioning as a non-slip portion for a user's fingers is formed on the side of the outer peripheral surface of the cylindrical main body 390 that is distal of the annular recess 398. The non-slip portion 402 is formed by a plurality of axially extending ribs 404 being disposed at equal intervals in the circumferential direction. In the present embodiment, six ribs 404 are disposed in the circumferential direction of the cylindrical main body 390. The moldability (injection molding precision) of the cap cover 372 is improved by the number of the ribs 404 being six as described above.

A locking projecting portion 406 for locking the distal end cover member 374 protrudes radially inward distal of the annular recess 398 on the inner peripheral surface of the cylindrical main body 390. Two locking projecting portions 406 are disposed so as to face each other.

The distal end cover member 374 is formed in a substantially U-shape in longitudinal cross portion. The distal end cover member 374 covers the cap body 370 together with the cap cover 372 such that a user operating the cap 10K cannot touch the cap body 370. In other words, the distal end cover member 374 has a contact blocking function. In addition, the distal end cover member 374 functions as a detachment blocking portion blocking the cap body 370 from being detached from the opening 390a of the cap cover 372.

The distal end cover member 374 is mounted so as to be rotatable with respect to the cap cover 372. The distal end cover member 374 has an annular portion 408 and a distal end wall 410 disposed in the distal end portion of the annular portion 408. The annular portion 408 has a proximal end portion fitted in the cylindrical main body 390 of the cap cover 372 so as to protrude distally from the opening 390a of the cap cover 372.

The annular portion 408 includes an annular peripheral wall portion 412 on the distal end side and a tubular engagement extending portion 414 extending in the proximal direction from the annular peripheral wall portion 412. The inner diameter of the annular portion 408 is constant from the distal end of the annular portion 408 to the proximal end of the annular portion 408 and is larger than the outer diameter of the distal end extending portion 378.

The outer diameter of the tubular engagement extending portion 414 is smaller than the inner diameter of the cylindrical main body 390. In other words, a gap is formed between the outer peripheral surface of the tubular engagement extending portion 414 and the inner peripheral surface of the cylindrical main body 390. The proximal end of the engagement extending portion 414 is in contact with the distal end of the cylindrical connecting portion 388.

An annular locking claw 416, which comes into contact with the locking projecting portion 406 of the cap cover 372, is disposed at the part of the outer peripheral surface of the tubular engagement extending portion 414 that corresponds to the annular recess 398 of the cap cover 372. The outer diameter of the locking claw 416 is larger than the separation interval of the locking projecting portion 406.

An annular support projection 418 coming into contact with the inner peripheral surface of the cylindrical main body 390 and an annular positioning projection 420 coming into contact with the distal end surface of the cap cover 372 are disposed on the side of the outer peripheral surface of the tubular engagement extending portion 414 that is distal of the locking projecting portion 406. The support projection 418 suppresses rattling of the distal end cover member 374 with respect to the cap cover 372. The positioning projection 420 has an inclined surface inclined outward in the proximal direction distal of the positioning projection 420. As a result, it is possible to inhibit the positioning projection 420 from being caught by the edge of an opening of an insertion tube during insertion into, for example, the insertion tube for transporting the syringe assembly 24K. In other words, the positioning projection 420 is formed in a triangular shape in transverse cross portion.

The distal end cover member 374 is integrally molded with a transparent resin material. In a case where a transparent resin material constitutes the cap cover 372, the transparency of the distal end cover member 374 is set higher than the transparency of the cap cover 372. As a result, a user can view the inside of the distal end cover member 374 more clearly than the inside of the cap cover 372 from the outside of the cap 10K. The distal end cover member 374 may be colored although the distal end cover member 374 is colorless in the present embodiment.

In the prefilled syringe 12K, the cap body 370 is positioned at the first position, where the distal end extending portion 378 is proximal of the opening 390a of the cylindrical main body 390, in the unopened state of the cap 10K. Specifically, the distal end of the cap body 370 is positioned more proximally than the opening 390a of the cylindrical main body 390 and in the tubular engagement extending portion 414 of the distal end cover member 374. As a result, the outer peripheral portion of the distal end extending portion 378, which is a viewing portion, is hidden in the substantially opaque cylindrical main body 390 and cannot be viewed from the outside. In addition, the mounting tube portion 376 as a mounting portion is in a state of being mounted on the nozzle portion 204, and the sealing portion 220 of the mounting tube portion 376 seals the drug discharge port 204a of the nozzle portion 204.

Figure 40A:
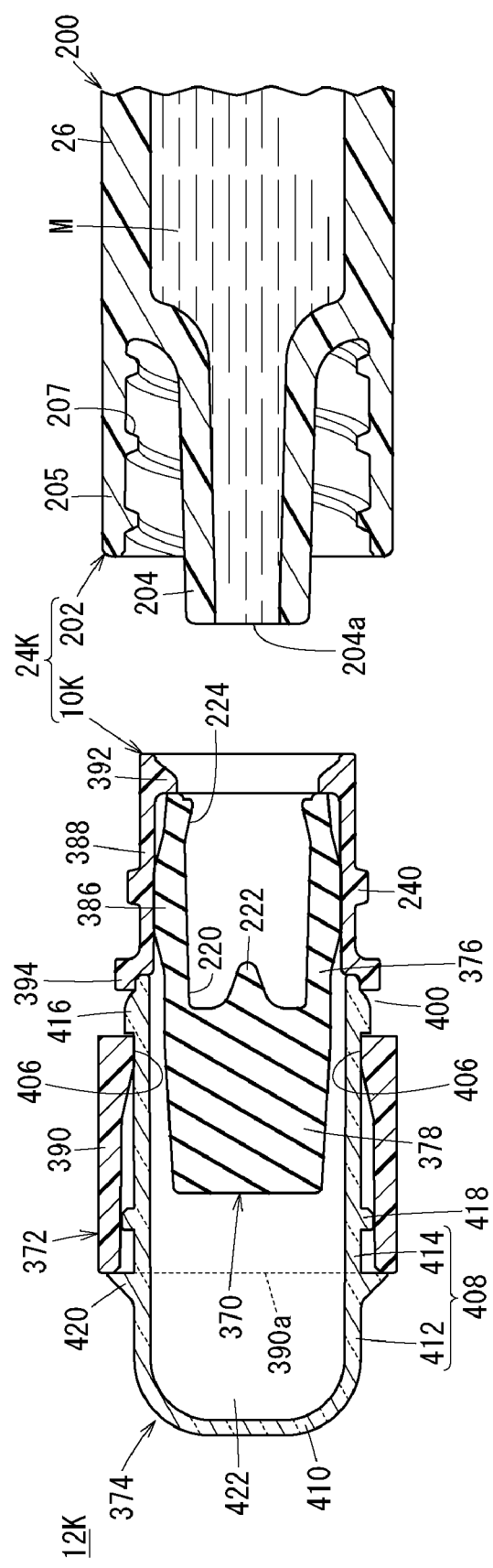
FIG. 40A is a longitudinal cross-sectional view illustrating the opened state of the cap illustrated in FIG. 39.

In a case where the cap 10K is opened from the syringe body 200, the cap cover 372 is pulled out from the syringe outer tube 202 with the screwing between the male screw portion 240 and the female screw portion 207 released. Then, the engaging claw portion 392 of the cylindrical connecting portion 388 comes into contact with the proximal end surface of the cap body 370 as illustrated in FIG. 40A. Then, the cap body 370 is pressed in the distal end direction by the cylindrical connecting portion 388 and the mounting tube portion 376 is detached from the nozzle portion 204. The cap 10K is opened as a result.

Figure 40B:
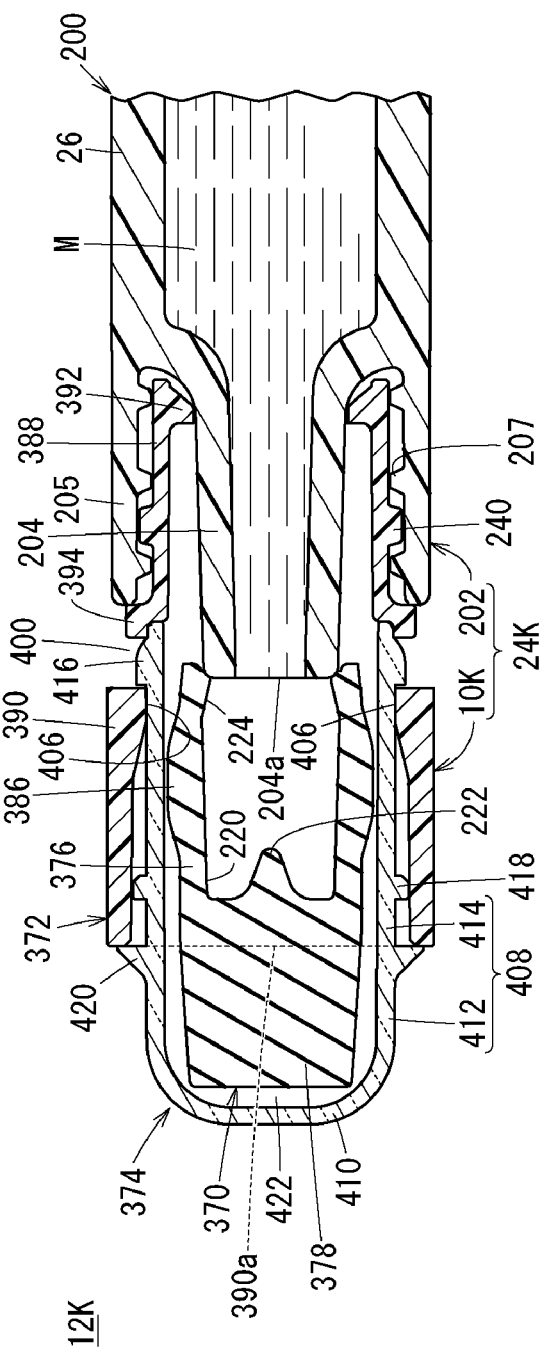
FIG. 40B is a longitudinal cross-sectional view illustrating the recapped state of the cap.

In a case where the syringe outer tube 202 is recapped with the cap 10K after opening, the distal end portion of the nozzle portion 204 of the syringe outer tube 202 is inserted into the cylindrical connecting portion 388 from the opening of the cylindrical connecting portion 388 that is on the proximal end side. Then, the distal end portion of the nozzle portion 204 comes into contact with the abutting projecting portion 224 of the cap body 370 as illustrated in FIG. 40B.

Once the cap cover 372 and the syringe outer tube 202 are subsequently brought close to each other, abutting between the abutting projecting portion 224 of the cap body 370 and the distal end portion of the nozzle portion 204 causes the cap body 370 at the first position to be pressed by the nozzle portion 204 and displaced in the distal end direction with respect to the cap cover 372. Then, the distal end extending portion 378 protrudes distally from the opening 390a on the distal end side of the cap cover 372.

Subsequently, the syringe outer tube 202 is recapped (remounted) with the cap 10K after opening by the male screw portion 240 of the cylindrical connecting portion 388 being screwed into the female screw portion 207 of the syringe side connecting portion 205. At this time, the cap body 370 is positioned at the second position, where the distal end extending portion 378 is received in a receiving space 422 formed by the annular peripheral wall portion 412 and the distal end wall 410. Accordingly, the outer peripheral portion of the distal end extending portion 378, which is a viewing portion, can be viewed from the outside via the transparent distal end cover member 374.

Figure 41A:
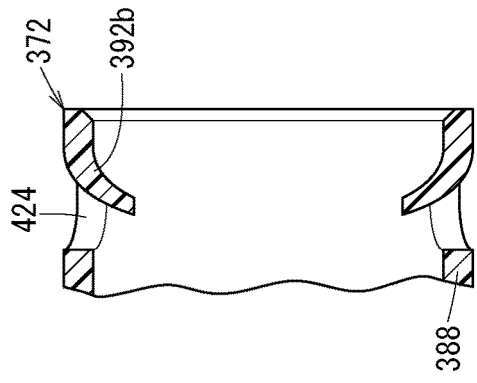
FIG. 41A is a cross-sectional view illustrating an engaging claw portion according to a first modification example of FIG. 38.

The prefilled syringe 12K is not limited to the above-described configuration. The cap 10K may have an engaging claw portion 392a illustrated in FIG. 41A in place of the engaging claw portion 392. The engaging claw portion 392a extends so as to be linearly inclined from the cylindrical main body 390 toward the distal end direction. The engaging claw portion 392a is elastically deformed radially outward by the cap body 370 inserted from the proximal end of the cap cover 372, and thus the cap body 370 can be easily inserted into the cap cover 372 from the proximal end of the cap cover 372.

Figure 41B:
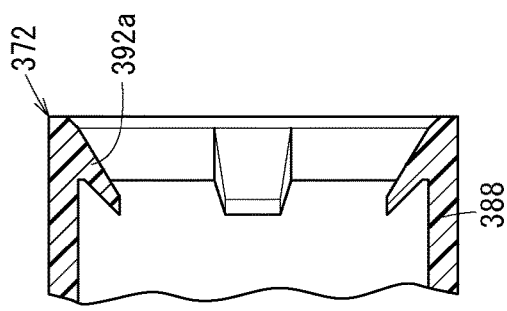
FIG. 41B is a cross-sectional view illustrating an engaging claw portion according to a second modification example of FIG. 38.

The cap 10K may have an engaging claw portion 392b illustrated in FIG. 41B in place of the engaging claw portion 392. The engaging claw portion 392b extends in a curved shape from the cylindrical main body 390 toward the distal end direction. The engaging claw portion 392b is curved so as to be convex on the outer surface side of the cap cover 372. A hole 424 is formed in the mounting tube portion 376 such that the engaging claw portion 392b is configured to be elastically deformed radially outward.

Figure 41C:
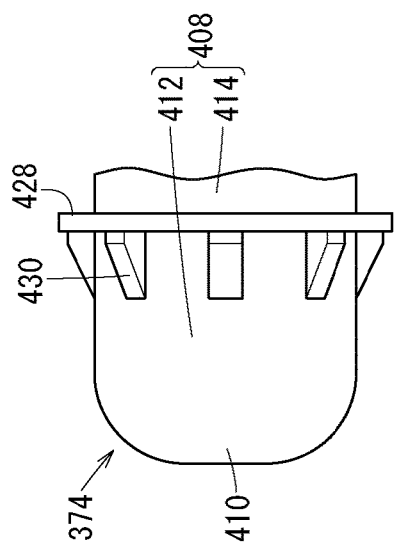
FIG. 41C is a cross-sectional view illustrating a distal end cover member according to the first modification example of FIG. 38.

An annular rib 426 may be disposed on the outer peripheral surface of the annular peripheral wall portion 412 of the distal end cover member 374 as illustrated in FIG. 41C. The annular rib 426 is disposed distal of the positioning projection 420 with a gap. The annular rib 426 is similar in shape to the positioning projection 420. The annular rib 426 has an inclined surface inclined outward in the proximal direction on the distal end side of the annular rib 426. As a result, it is possible to inhibit the annular rib 426 from being caught by the edge of an opening of an insertion tube during insertion into, for example, the insertion tube for transporting the syringe assembly 24K.

Figure 41D:
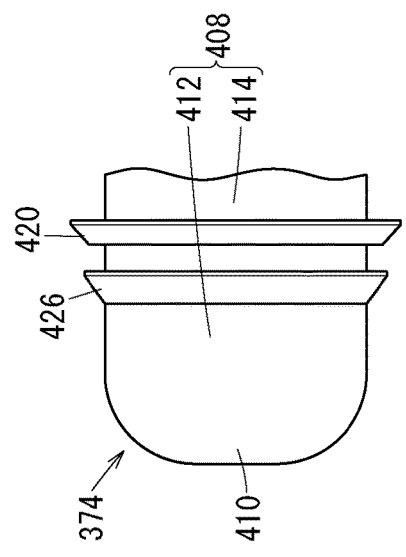
FIG. 41D is a cross-sectional view illustrating a distal end cover member according to the second modification example of FIG. 38.

The distal end cover member 374 may have a positioning projection body 428 and a plurality of inclined ribs 430 disposed at the distal end of the positioning projection body 428 as illustrated in FIG. 41D. The positioning projection body 428 is formed in a rectangular shape in transverse cross portion. The plurality of inclined ribs 430 are disposed on the distal end surface of the positioning projection body 428 so as to be positioned at equal intervals in the circumferential direction of the distal end cover member 374. A positioning projection similar to the positioning projection 420 is formed by the positioning projection body 428 and the plurality of inclined ribs 430. The plurality of inclined ribs 430 have inclined surfaces inclined outward in the proximal direction on the distal end sides of the plurality of inclined ribs 430. As a result, it is possible to inhibit the positioning projection including the positioning projection body 428 and the plurality of inclined ribs 430 from being caught by the edge of an opening of an insertion tube during insertion into, for example, the insertion tube for transporting the syringe assembly 24K.

The cap, the syringe assembly, and the prefilled syringe according to the present invention are not limited to the embodiments described above. It is a matter of course that various configurations can be adopted for the cap, the syringe assembly, and the prefilled syringe according to the present invention without departing from the gist of the present invention. For example, the prefilled syringe may have no pusher. In this case, a pressing member pressing the gasket in the distal end direction is separately mounted for the prefilled syringe. In addition, the abutting projecting portion may be omitted from the cap body in the cap, the syringe assembly, or the prefilled syringe. In this case, the proximal end of the mounting tube portion functions as an abutting portion configured to abut against the distal end portion of the nozzle by the distal end outer diameter of the nozzle of the syringe outer tube being allowed to exceed the inner diameter of the opening of the proximal end side of the mounting tube portion.

The cap body may be configured such that the viewing portion does not include the distal end of the cap body and the distal end of the cap body protrudes to the side distal of the opening of the cap cover at the first position. In this case, the viewing portion of the cap body is disposed so as to be positioned in the cylindrical main body of the cap cover when the cap body is at the first position and protrude from the opening of the cap cover when the cap body is at the second position.

Examples of the viewing portion include a viewing portion formed by an outer peripheral surface slightly proximal of the distal end of the cap body being colored in red or the like and a viewing portion formed of a colored member fitted so as to cover an outer peripheral portion slightly proximal of the distal end of the distal end protruding portion of the cap body. Even in the configurations, the outer peripheral portion of the viewing portion changes in appearance as the cap body is displaced. Accordingly, a user can easily and reliably discriminate between the unopened state and the recapped state of the cap.

Further, in the embodiments provided with the distal end cover member that has the contact blocking function, the cap cover may be configured to be transparent and the distal end cover member may be configured to be substantially opaque. In this case, the viewing portion (distal end protruding portion) of the cap body is visible at the first position and invisible at the second position. Even in the configurations, a change in the appearance of the outer peripheral portion of the viewing portion (distal end protruding portion) becomes clear.

In an alternative configuration, a transparent resin material may constitute both the cap cover and the distal end cover member and the visibility of the inside of the cap cover and the visibility of the inside of the distal end cover member may differ from each other. In an example of the configuration, the outer peripheral surface of one of the cap cover and the distal end cover member is provided with multiple irregularities and the outer peripheral surface of the other is smooth such that the inside of one is less visible than the inside of the other or the transparency of the cap cover and the transparency of the distal end cover member differ from each other. Even in the configuration, the outer peripheral portion of the viewing portion (distal end protruding portion) changes in appearance as the cap body is displaced. Accordingly, a user can easily and reliably discriminate between the unopened state and the recapped state of the cap.

A hole may be formed in the distal end wall of the distal end cover member and the hole may have a size at which a user cannot insert his or her finger. In a case where the hole is formed in the distal end wall, it is possible to mount the preassembled cap on the syringe outer tube by inserting a jig into the hole in the distal end wall and pushing the cap body into the nozzle portion.

The cap may be provided with a temporary fixing mechanism providing temporary fixing for the cap body not to move from the first position to the second position in a state in which the cap is removed from the syringe body. Examples of the temporary fixing mechanism include a temporary fixing projection disposed on the inner peripheral surface of the cap cover and engaged with a part of the cap body disposed at the first position. In this case, the force of engagement between the temporary fixing projection and the cap body is set so as to be releasable by the mounting portion (mounting tube portion) of the cap body being pressed with the nozzle portion of the syringe body. As a result, it is possible to inhibit an unintended displacement of the cap body from the first position to the second position in the unopened state and it is possible to displace the cap body from the first position to the second position when the mounting portion (mounting tube portion) of the cap removed from the syringe body is close to the nozzle portion of the syringe body with the cap body disposed at the first position.

It should be noted that the cap body in each of the embodiments is configured to move from the first position to the second position, without the mounting portion (mounting tube portion) being pressed by the nozzle portion, in a state in which the cap is removed from the syringe body. Accordingly, displacement of the cap body from the first position to the second position does not occur in a case where the cap removed from the syringe body is remounted on the syringe body with the cap body disposed at the second position. Even in this case, displacement of the cap body from the second position to the first position is restricted by the mounting portion (mounting tube portion) of the cap body disposed at the second position abutting against the nozzle portion, and thus the appearance of the outer peripheral portion of the viewing portion remains different from the appearance in the unopened state. Accordingly, a user can easily and reliably discriminate between the unopened and opened states of the cap.

What is claimed is:

1. A cap that is detachable from a syringe body that comprises: a body portion that is configured to accommodate a drug, and a nozzle portion that protrudes in a distal direction from a distal end portion of the body portion and comprises a drug discharge port at a distal end of the nozzle portion, the cap comprising:
a cap body comprising:
  a mounting portion that is configured to be mounted on the nozzle portion and that comprises a sealing portion that seals the drug discharge port in a liquid-tight manner, and
  a viewing portion that is positioned distal of the mounting portion;
a tubular cap cover that covers the cap body and comprises a cylindrical main body that comprises an opening at a distal end of the cylindrical main body;
a distal end cover member that is mounted on a distal end portion of the cap cover and comprises:
  an annular peripheral wall portion that extends in a distal direction from the opening of the cylindrical main body, and
  a distal end wall that is disposed at a distal end of the annular peripheral wall portion,
  wherein the annular peripheral wall portion and the distal end wall form a receiving space; and
an engaging portion that inhibits detachment of the cap body in a proximal end direction with respect to the cap cover by engagement with the cap body;
wherein the cap body is configured to be displaced in the cap cover along an axial direction of the cap cover from a first position at which the viewing portion is positioned in the cylindrical main body to a second position at which the viewing portion protrudes in a distal direction from the opening of the cylindrical main body into the receiving space;
wherein the sealing portion is configured to seal the nozzle portion in a liquid-tight manner in a state in which the cap body is positioned at the first position;
wherein the mounting portion is configured to be pressed in a distal direction by the nozzle portion of the syringe body so as to displace the cap body from the first position to the second position when the mounting portion of the cap removed from the syringe body is brought close to the nozzle portion of the syringe body in a state in which the cap body is disposed at the first position;
wherein at least an outer peripheral portion of the viewing portion changes in appearance by the viewing portion protruding from the opening due to displacement of the cap body from the first position to the second position; and
wherein the cylindrical main body and the distal end cover member cover the cap body such that a user operating the cap cannot touch the cap body in an abutting state in which the cap body is positioned at the second position and the mounting portion abuts against the nozzle portion of the syringe body.

2. The cap according to claim 1, wherein:
a distal end of the annular peripheral wall portion is closed by the distal end wall.

3. The cap according to claim 1, wherein:
the distal end cover member is transparent and the cylindrical main body is opaque.

4. The cap according to claim 1, wherein:
the distal end cover member comprises an engagement extending portion that extends from a proximal end of the annular peripheral wall portion into the cylindrical main body through the opening; and
the distal end cover member is mounted on the cylindrical main body by engagement of the engagement extending portion with an inner peripheral surface of the cylindrical main body.

5. The cap according to claim 4, wherein:
the distal end cover member comprises a positioning projection that protrudes from an outer peripheral surface of a proximal end portion of the annular peripheral wall portion; and
movement of the distal end cover member (in a proximal direction with respect to the cylindrical main is inhibited by the positioning projection abutting against a distal end surface of the cylindrical main body.

6. The cap according to claim 4, wherein:
the distal end cover member comprises an annular portion that comprises the annular peripheral wall portion and the engagement extending portion;
an inner diameter of the annular portion is constant from a distal end of the annular portion to a proximal end of the annular portion and is larger than an outer diameter of the viewing portion; and
at least a distal end of the viewing portion is positioned in the annular portion when the cap body is at the first position.

7. The cap according to claim 1, wherein:
the cap cover is opaque; and
an outer peripheral portion of the viewing portion is not visible when the cap body is at the first position, and the outer peripheral portion of the viewing portion is visible when the cap body is at the second position.

8. The cap according to claim 1, wherein:
the viewing portion is disposed at a distal end of the cap body.

9. A syringe assembly comprising:
a syringe body that comprises:
    a body portion that is configured to accommodate a drug, and
    a nozzle portion that protrudes in a distal direction from a distal end portion of the body portion and comprises a drug discharge port at a distal end of the nozzle portion;
a cap that is detachable from the syringe body and comprises:
    a cap body comprising:
        a mounting portion that is mounted on the nozzle portion and that comprises a sealing portion that seals the drug discharge port in a liquid-tight manner, and
        a viewing portion that is positioned distal of the mounting portion;
    a tubular cap cover that covers the cap body and comprises a cylindrical main body that comprises an opening at a distal end of the cylindrical main body,
    a distal end cover member that is mounted on a distal end portion of the cap cover and comprises:
        an annular peripheral wall portion that extends in a distal direction from the opening of the cylindrical main body, and
        a distal end wall that is disposed at a distal end of the annular peripheral wall portion,
        wherein the annular peripheral wall portion and the distal end wall form a receiving space, and
    an engaging portion that inhibits detachment of the cap body in a proximal end direction with respect to the cap cover by engagement with the cap body;
wherein the cap body is configured to be displaced in the cap cover along an axial direction of the cap cover from a first position at which the viewing portion is positioned in the cylindrical main body to a second position at which the viewing portion protrudes in a distal direction from the opening of the cylindrical main body into the receiving space;

wherein the sealing portion is configured to seal the nozzle portion in a liquid-tight manner in a state in which the cap body is positioned at the first position;

wherein the mounting portion is configured to be pressed in a distal direction by the nozzle portion of the syringe body so as to displace the cap body from the first position to the second position when the mounting portion of the cap removed from the syringe body is brought close to the nozzle portion of the syringe body in a state in which the cap body is disposed at the first position;

wherein at least an outer peripheral portion of the viewing portion changes in appearance by the viewing portion protruding from the opening due to displacement of the cap body from the first position to the second position; and wherein the cylindrical main body and the distal end cover member cover the cap body such that a user operating the cap cannot touch the cap body in an abutting state in which the cap body is positioned at the second position and the mounting portion abuts against the nozzle portion of the syringe body.

10. The syringe assembly according to claim 9, wherein:
an outer diameter of the viewing portion is larger than an outer diameter of a part of the nozzle portion at which the mounting portion is fitted.

11. The syringe assembly according to claim 9, wherein:
the nozzle portion comprises:
    a hollow needle body that comprises the drug discharge port at a distal end thereof, and
    a needle hub to which a proximal end side of the needle body is attached;
the mounting portion is a mounting tube portion that is configured to accommodate the needle body and the needle hub;
the sealing portion closes a distal end of the mounting tube portion; and
the drug discharge port is sealed in a liquid-tight manner by a distal end portion of the needle body puncturing the sealing portion, and the needle hub is fitted in the mounting tube portion when the cap body is at the first position.

12. The syringe assembly according to claim 9, wherein:
the nozzle portion is formed in a hollow shape; and
the mounting portion is fitted into the nozzle portion.

13. A prefilled syringe comprising:
the syringe assembly according to claim 9;
a drug filled in the syringe outer tube; and
a gasket that is configured to slide in the syringe outer tube in a liquid-tight manner and in an axial direction.

14. A syringe assembly comprising:
a syringe body that comprises:
    a body portion that is configured to accommodate a drug, and
    a nozzle portion that protrudes in a distal direction from a distal end portion of the body portion and comprises a drug discharge port at a distal end of the nozzle portion;

a cap that is detachable from the syringe body and comprises:
  a cap body comprising:
    a mounting portion that is mounted on the nozzle portion and that comprises a sealing portion that seals the drug discharge port in a liquid-tight manner, and
    a viewing portion that is positioned distal of the mounting portion;
  a tubular cap cover that covers the cap body and comprises a cylindrical main body that comprises an opening at a distal end of the cylindrical main body,
  a distal end cover member that is mounted on a distal end portion of the cap cover and comprises:
    an annular peripheral wall portion that extends in a distal direction from the opening of the cylindrical main body, and
    a distal end wall that is disposed at a distal end of the annular peripheral wall portion,
      wherein the annular peripheral wall portion and the distal end wall form a receiving space, and
    an engaging portion that inhibits detachment of the cap body in a proximal end direction with respect to the cap cover by engagement with the cap body;
  wherein the cap body is configured to be displaced in the cap cover along an axial direction of the cap cover from a first position at which the viewing portion is positioned in the cylindrical main body to a second position at which the viewing portion protrudes in a distal direction from the opening of the cylindrical main body into the receiving space;
  wherein the sealing portion is configured to seal the nozzle portion in a liquid-tight manner in a state in which the cap body is positioned at the first position;
  wherein the mounting portion is configured to be pressed in a distal direction by the nozzle portion of the syringe body so as to displace the cap body from the first position to the second position when the mounting portion of the cap removed from the syringe body is brought close to the nozzle portion of the syringe body in a state in which the cap body is disposed at the first position;
  wherein at least an outer peripheral portion of the viewing portion changes in appearance by the viewing portion protruding from the opening due to displacement of the cap body from the first position to the second position;
  wherein the cylindrical main body and the distal end cover member cover the cap body such that a user operating the cap cannot touch the cap body in an abutting state in which the cap body is positioned at the second position and the mounting portion abuts against the nozzle portion of the syringe body;
  wherein the syringe body comprises a cylindrical lock adapter that comprises a female screw portion on an inner peripheral surface of the lock adapter and covers an outer peripheral portion of the nozzle portion;
  wherein the mounting portion is a cylindrical mounting tube portion that is configured to accommodate the nozzle portion;
  wherein the mounting tube portion comprises:
    the sealing portion that is positioned in a distal end portion of the mounting tube portion, and
    an abutting portion that is positioned in a proximal end portion of the mounting tube portion and is configured to abut against a distal end portion of the nozzle portion;
  wherein the cap cover comprises a cylindrical connecting portion that is positioned in a proximal end portion of the cap cover and is detachable from the lock adapter by screwing;
  wherein the cylindrical connecting portion is tubular so as to be inserted between the lock adapter and the nozzle portion, and comprises a male screw portion in an outer peripheral portion of the cylindrical connecting portion, the male screw portion being configured to be screwed with the female screw portion of the lock adapter;
  wherein the mounting tube portion is inserted between the cylindrical connecting portion and the nozzle portion and the sealing portion seals the drug discharge port in a liquid-tight manner in a state in which the cap is mounted on the syringe body by screwing of the male screw portion of the cylindrical connecting portion with the female screw portion of the lock adapter and the cap body is positioned at the first position; and
  wherein the cap body is displaced from the first position to the second position and an outer peripheral portion of the viewing portion changes in appearance by the abutting portion of the cap body being pressed by the distal end portion of the nozzle portion when the male screw portion of the cylindrical connecting portion is screwed into the female screw portion of the lock adapter with the cap removed from the syringe body.

15. The syringe assembly according to claim 14, wherein:

the mounting tube portion comprises an abutting projecting portion that protrudes inward and functions as the abutting portion on an inner peripheral surface of the proximal end portion of the mounting tube portion.

16. The syringe assembly according to claim 15, wherein:

the abutting projecting portion is annularly disposed on the inner peripheral surface of the proximal end portion of the mounting tube portion.

17. The syringe assembly according to claim 16, wherein:

the mounting tube portion comprises a notch portion in which the abutting projecting portion is notched in an axial direction of the mounting tube portion;

the inner peripheral surface of the mounting tube portion is configured to form a circumferentially continuous airtight seal with an outer peripheral surface of the nozzle portion at least in a vicinity of a distal end of the abutting projecting portion when the sealing portion seals the drug discharge port in a liquid-tight manner; and the airtight seal is released and an inside of the mounting tube portion, which is distal of the abutting projecting portion, communicates with an outside via the notch portion when the sealing portion is separated by a predetermined distance from the drug discharge port and the abutting projecting portion abuts against an outer peripheral surface of the nozzle portion.

18. The syringe assembly according to claim 14, wherein:

the cap cover comprises an insertion restricting portion that is configured to abut against a distal end of the lock adapter at a proximal end of the cylindrical main body, and the insertion restricting portion restricts a length of insertion of the cylindrical connecting portion between the lock adapter and the nozzle portion by abutting against a distal end of the lock adapter.

19. A prefilled syringe comprising:
the syringe assembly according to claim 14;
a drug filled in the syringe outer tube; and
a gasket that is configured to slide in the syringe outer tube in a liquid-tight manner and in an axial direction.

\* \* \* \* \*